US012672956B2

(12) United States Patent
Schraub et al.

(10) Patent No.: US 12,672,956 B2
(45) Date of Patent: Jul. 7, 2026

(54) SYSTEM AND METHOD FOR IRRADIATING AN ARTIFICIAL LENS

(71) Applicant: Johnson & Johnson Surgical Vision, Inc., Irvine, CA (US)

(72) Inventors: Martin Schraub, Alsbach-Haehnlein (DE); Lars Dobelmann-Mara, Gross-Zimmern (DE); Simon Helmstetter, Gross-Umstadt (DE); David Moore, Weinheim (DE); Stefan Riedmueller, Frankfurt Am Main (DE); Harald Guenther, Darmstadt (DE)

(73) Assignee: AMO DEVELOPMENT, LLC, Irvine, CA (US)

(*) Notice: Subject to any disclaimer, the term of this patent is extended or adjusted under 35 U.S.C. 154(b) by 1256 days.

(21) Appl. No.: 17/606,070

(22) PCT Filed: Apr. 24, 2020

(86) PCT No.: PCT/EP2020/061507
§ 371 (c)(1),
(2) Date: Oct. 25, 2021

(87) PCT Pub. No.: WO2020/216928
PCT Pub. Date: Oct. 29, 2020

(65) Prior Publication Data
US 2022/0202566 A1 Jun. 30, 2022

(30) Foreign Application Priority Data
Apr. 26, 2019 (EP) .................................... 19171461

(51) Int. Cl.
*A61F 2/16* (2006.01)
*A61F 9/008* (2006.01)
*G02B 21/00* (2006.01)

(52) U.S. Cl.
CPC ........ *A61F 2/1613* (2013.01); *A61F 9/00829* (2013.01); *A61F 9/00834* (2013.01);
(Continued)

(58) Field of Classification Search
CPC ................ A61F 2/1613; A61F 9/00829; A61F 9/00834; A61F 2002/1699;
(Continued)

(56) References Cited

U.S. PATENT DOCUMENTS 3,351,482 A 11/1967 Roderich et al.
3,420,835 A 1/1969 Wirth et al.
(Continued)

FOREIGN PATENT DOCUMENTS

CN 101738657 A 6/2010
CN 102438549 A 5/2012
(Continued)

OTHER PUBLICATIONS

Translation of JP2015195921A (Year: 2015).*
(Continued)

*Primary Examiner* — Niketa Patel
*Assistant Examiner* — Attiya Sayyada Hussaini

(57) ABSTRACT

The present invention generally relates to a system for two-photon or multi-photon irradiating an artificial lens, preferably an intraocular lens preferably arranged within an eye of a patient and a method for locally adjusting a polarizability and/or a refractive index of an artificial lens preferably an intraocular lens preferably arranged within an eye of a patient. The method relates in particular to fabrication of optical profiles by adjusting polarizability through two- or multi-photon processes in a non-destructive manner.

19 Claims, 16 Drawing Sheets

(52) U.S. Cl.
CPC .. *G02B 21/0012* (2013.01); *A61F 2002/1699* (2015.04); *A61F 2240/001* (2013.01); *A61F 2250/0058* (2013.01)

(58) Field of Classification Search
CPC ........ A61F 2240/001; A61F 2250/0058; A61F 2/16; A61F 2/1627; A61F 9/0084; A61F 2009/0087; A61F 2009/00878; A61F 2009/00897; G02B 21/0012
See application file for complete search history.

(56) References Cited

U.S. PATENT DOCUMENTS

| | | | |
|---|---|---|---|
| 4,103,256 | A | 7/1978 | Hammond et al. |
| 4,230,850 | A | 10/1980 | Briet et al. |
| 4,349,619 | A | 9/1982 | Kamoshida et al. |
| 4,785,004 | A | 11/1988 | Von et al. |
| 5,077,335 | A | 12/1991 | Schwabe et al. |
| 5,290,892 | A | 3/1994 | Namdaran et al. |
| 5,331,073 | A | 7/1994 | Weinschenk, III et al. |
| 5,585,385 | A | 12/1996 | Natsugari et al. |
| 5,693,095 | A | 12/1997 | Freeman et al. |
| 5,968,952 | A | 10/1999 | Venet et al. |
| 6,143,766 | A | 11/2000 | Kaltenbronn et al. |
| 6,201,087 | B1 | 3/2001 | Herr et al. |
| 6,331,562 | B1 | 12/2001 | Bhagwat et al. |
| 6,887,269 | B1 | 5/2005 | Hampp et al. |
| 7,247,646 | B2 | 7/2007 | McKie et al. |
| 7,399,767 | B2 | 7/2008 | Zhang et al. |
| 7,642,364 | B2 | 1/2010 | Liu et al. |
| 8,109,999 | B2 * | 2/2012 | Hampp ................. A61F 2/1613 623/6.56 |
| 8,247,511 | B2 | 8/2012 | Mentak |
| 8,329,849 | B2 | 12/2012 | Iji et al. |
| 8,366,963 | B2 | 2/2013 | Goto et al. |
| 8,409,177 | B1 * | 4/2013 | Lai .......................... A61F 9/008 606/4 |
| 8,506,558 | B2 * | 8/2013 | Gertner ................ A61N 5/1017 378/65 |
| 8,592,007 | B2 | 11/2013 | Goetz et al. |
| 9,315,496 | B2 | 4/2016 | Zhang et al. |
| 9,580,653 | B2 | 2/2017 | Archetti et al. |
| 9,777,216 | B2 | 10/2017 | Klasen-Memmer et al. |
| 9,823,492 | B2 | 11/2017 | De et al. |
| 10,351,771 | B2 | 7/2019 | Goebel et al. |
| 10,383,721 | B2 | 8/2019 | Marcos Celestino et al. |
| 10,386,653 | B2 | 8/2019 | Beaton et al. |
| 10,414,743 | B2 | 9/2019 | Taugerbeck et al. |
| 10,457,658 | B2 | 10/2019 | Dobelmann-Mara et al. |
| 10,723,713 | B2 | 7/2020 | Dobelmann-Mara et al. |
| 10,864,114 | B2 * | 12/2020 | Schuele .............. A61F 9/00827 |
| 10,875,833 | B2 | 12/2020 | Kumar et al. |
| 11,359,031 | B2 | 6/2022 | Dobelmann-Mara et al. |
| 2005/0054586 | A1 | 3/2005 | Bartels et al. |
| 2005/0176763 | A1 | 8/2005 | Boy et al. |
| 2006/0147840 | A1 | 7/2006 | Ishidai |
| 2007/0053831 | A1 | 3/2007 | Barrio et al. |
| 2007/0218567 | A1 | 9/2007 | Tanaka et al. |
| 2008/0004610 | A1 | 1/2008 | Miller et al. |
| 2009/0143858 | A1 | 6/2009 | Knox et al. |
| 2010/0114076 | A1 | 5/2010 | Reinstein et al. |
| 2010/0160482 | A1 | 6/2010 | Nachbaur |
| 2010/0227273 | A1 | 9/2010 | Hatakeyama et al. |
| 2010/0228345 | A1 * | 9/2010 | Bille .................. B23K 26/0624 623/6.23 |
| 2010/0324165 | A1 | 12/2010 | Ritter et al. |
| 2011/0021522 | A1 | 1/2011 | Wells et al. |
| 2011/0028667 | A1 | 2/2011 | Ritter et al. |
| 2011/0092612 | A1 | 4/2011 | Miki et al. |
| 2011/0215334 | A1 | 9/2011 | Quinn et al. |
| 2011/0245919 | A1 | 10/2011 | Pettit |
| 2013/0033975 | A1 | 2/2013 | Gindre et al. |
| 2013/0114010 | A1 | 5/2013 | Goetz et al. |
| 2014/0058367 | A1 | 2/2014 | Dantus |
| 2014/0066537 | A1 * | 3/2014 | Jerome ................... C08L 83/08 526/268 |
| 2015/0274885 | A1 | 10/2015 | Joy et al. |
| 2016/0081852 | A1 * | 3/2016 | Peyman .............. A61F 9/00827 604/20 |
| 2016/0089270 | A1 | 3/2016 | Fu |
| 2016/0331868 | A1 * | 11/2016 | Grubbs ..................... A61F 9/00 |
| 2017/0306121 | A1 | 10/2017 | Brust et al. |
| 2018/0162817 | A1 | 6/2018 | Dobelmann-Mara et al. |
| 2018/0214310 | A1 * | 8/2018 | Dick .................. A61F 9/00838 |
| 2018/0243082 | A1 | 8/2018 | Zheleznyak et al. |
| 2018/0271646 | A1 | 9/2018 | Marcos Celestino et al. |
| 2019/0001024 | A1 | 1/2019 | Grubbs et al. |
| 2019/0389827 | A1 | 12/2019 | Dobelmann-Mara et al. |
| 2019/0389829 | A1 | 12/2019 | Dobelmann-Mara et al. |
| 2020/0002304 | A1 | 1/2020 | Dobelmann-Mara et al. |
| 2020/0002363 | A1 | 1/2020 | Dobelmann-Mara et al. |
| 2020/0038549 | A1 | 2/2020 | Stoy et al. |
| 2020/0046558 | A1 | 2/2020 | Fu et al. |
| 2020/0055833 | A1 | 2/2020 | Schraub et al. |
| 2020/0062739 | A1 | 2/2020 | Dobelmann-Mara et al. |
| 2020/0231559 | A1 | 7/2020 | Dobelmann-Mara et al. |
| 2020/0262805 | A1 | 8/2020 | Dobelmann Mara |
| 2020/0332041 | A1 | 10/2020 | Dobelmann-Mara et al. |
| 2021/0016496 | A1 * | 1/2021 | Chen ..................... B29C 64/129 |
| 2021/0363122 | A1 | 11/2021 | Dobelmann-Mara et al. |
| 2023/0084690 | A1 | 3/2023 | Gerstenecker |
| 2023/0203214 | A1 | 6/2023 | Riedmueller et al. |
| 2024/0117092 | A1 | 4/2024 | Dobelmann-Mara et al. |
| 2024/0142665 | A1 | 5/2024 | Dobelmann-Mara et al. |

FOREIGN PATENT DOCUMENTS

| | | | | |
|---|---|---|---|---|
| CN | 102532015 | B | 10/2013 | |
| CN | 104656272 | A | 5/2015 | |
| CN | 106810559 | A | 6/2017 | |
| CN | 105753837 | B | 4/2018 | |
| CN | 106810560 | B | 3/2019 | |
| CN | 111040202 | A | 4/2020 | |
| CN | 111378138 | A | 7/2020 | |
| CN | 111378159 | A | 7/2020 | |
| CN | 111378160 | A | 7/2020 | |
| CN | 111378163 | A | 7/2020 | |
| CN | 111378165 | A | 7/2020 | |
| CN | 111378168 | A | 7/2020 | |
| DE | 10147238 | A1 | 4/2003 | |
| EP | 0155177 | A2 | 9/1985 | |
| EP | 0354179 | B1 | 8/1994 | |
| EP | 1342770 | B1 | 5/2006 | |
| EP | 1926454 | B1 | 3/2010 | |
| EP | 1958945 | B1 | 11/2014 | |
| EP | 1683792 | B9 | 10/2016 | |
| EP | 2698369 | B1 | 2/2017 | |
| EP | 3133065 | A1 | 2/2017 | |
| EP | 3363791 | A1 | 8/2018 | |
| FR | 2118191 | A1 | 7/1972 | |
| GB | 1212174 | A | 11/1970 | |
| JP | S52122371 | A | 10/1977 | |
| JP | S5735850 | A | 2/1982 | |
| JP | S5735850 | U | 2/1982 | |
| JP | H03275681 | A | 12/1991 | |
| JP | H05263072 | A | 10/1993 | |
| JP | H063761 | A | 1/1994 | |
| JP | H108301849 | A | 11/1996 | |
| JP | H08337583 | A | 12/1996 | |
| JP | 2876129 | B2 | 3/1999 | |
| JP | H11514635 | A | 12/1999 | |
| JP | 3275681 | B2 | 4/2002 | |
| JP | 2004203751 | A | 7/2004 | |
| JP | 2007505835 | A | 3/2007 | |
| JP | 2007510674 | A | 4/2007 | |
| JP | 2011505932 | A | 3/2011 | |
| JP | 2012506878 | A | 3/2012 | |
| JP | 2012124297 | A | 6/2012 | |
| JP | 5263072 | B2 | 8/2013 | |
| JP | 2015195921 | A * | 11/2015 | ......... A61F 9/00825 |
| JP | 2017511169 | A | 4/2017 | |
| JP | 2018529659 | A | 10/2018 | |
| PL | 108383 | U1 | 3/1999 | |

(56) References Cited

FOREIGN PATENT DOCUMENTS

| | | | | |
|---|---|---|---|---|
| TW | I308658 | B | 4/2009 | |
| WO | 9924420 | A1 | 5/1999 | |
| WO | 0008026 | A2 | 2/2000 | |
| WO | 0118079 | A1 | 3/2001 | |
| WO | 0197217 | A2 | 12/2001 | |
| WO | WO-03092566 | A1 * | 11/2003 | ............. A61F 9/008 |
| WO | 2005028472 | A1 | 3/2005 | |
| WO | 2005065689 | A1 | 7/2005 | |
| WO | 2006078834 | A1 | 7/2006 | |
| WO | 2007001407 | A2 | 1/2007 | |
| WO | 2007033831 | A1 | 3/2007 | |
| WO | 2007066755 | A1 | 6/2007 | |
| WO | 2007082178 | A2 | 7/2007 | |
| WO | 2007132948 | A1 | 11/2007 | |
| WO | 2007136125 | A1 | 11/2007 | |
| WO | 2008013950 | A2 | 1/2008 | |
| WO | 2008094476 | A1 | 8/2008 | |
| WO | 2008096673 | A1 | 8/2008 | |
| WO | 2009032754 | A2 | 3/2009 | |
| WO | 2009074520 | A2 | 6/2009 | |
| WO | 2009074521 | A1 | 6/2009 | |
| WO | 2009156182 | A2 | 12/2009 | |
| WO | 2010049044 | A1 | 5/2010 | |
| WO | 2010049269 | A1 | 5/2010 | |
| WO | 2010049270 | A1 | 5/2010 | |
| WO | 2010086484 | A1 | 8/2010 | |
| WO | 2011057942 | A1 | 5/2011 | |
| WO | 2011087831 | A1 | 7/2011 | |
| WO | 2011098224 | A1 | 8/2011 | |
| WO | 2011117195 | A1 | 9/2011 | |
| WO | 2012034719 | A1 | 3/2012 | |
| WO | 2012097858 | A1 | 7/2012 | |
| WO | 2012150550 | A1 | 11/2012 | |
| WO | 2012167124 | A1 | 12/2012 | |
| WO | 2013130689 | A1 | 9/2013 | |
| WO | 2014059350 | A1 | 4/2014 | |
| WO | 2014090362 | A1 | 6/2014 | |
| WO | 2015003095 | A1 | 1/2015 | |
| WO | 2016146583 | A1 | 9/2016 | |
| WO | 2016200401 | A1 | 12/2016 | |
| WO | 2017025115 | A1 | 2/2017 | |
| WO | 17032442 | A1 | 3/2017 | |
| WO | 17032443 | A1 | 3/2017 | |
| WO | 2017032444 | A1 | 3/2017 | |
| WO | 17221068 | A1 | 12/2017 | |
| WO | 18149850 | A1 | 8/2018 | |
| WO | 18149852 | A1 | 8/2018 | |
| WO | 18149853 | A1 | 8/2018 | |
| WO | 18149855 | A1 | 8/2018 | |
| WO | 18149856 | A1 | 8/2018 | |
| WO | 18149857 | A1 | 8/2018 | |
| WO | 2018171688 | A1 | 9/2018 | |
| WO | 2019097232 | A1 | 5/2019 | |

OTHER PUBLICATIONS

Translation of WO03092566A1 (Year: 2003).*

Busch A.P., et al., "Two-Photon-Absorption Triggered Release of 5-Fluorouracil from Isomer-Pure Polymer Bound Syn-Head-to-Head Dimers for Novel Intraocular Lenses," International Journal of Drug Delivery, 2015, vol. 7, pp. 174-190.

Helmstetter S., et al., "High-refractive Quinolinone-based Polymers for Ophthalmic Devices," Journal of Polymer Research, 2016, vol. 23 (12), 14 pages.

Johnston P., et al., "Topochemical Photo-reversible Polymerization of a Bioinspired Monomer and its Recovery and Repolymerization After Photo-depolymerization," Chemical Science, 2012, vol. 3 (7), pp. 2301-2306.

Lohse B., et al., "N1-Alkylated Pyrimidine Films as a New Potential Optical Data Storage Medium," Chemistry of Materials, 2006, vol. 18 (20), pp. 4808-4816.

Lohse B., et al., "Photodimerization in Pyrimidine-substituted Dipeptides," Journal of Peptide Science, 2005, vol. 11 (8), pp. 499-505.

Lohse B., et al., "UV-photodimerization in Uracil-substituted Dendrimers for High Density Data Storage," Journal of Polimer Science, 2007, vol. 45 (19), pp. 4401-4412.

Matharu A.S., et al., "Photochromic Polymers for Optical Data Storage: Azobenzenes and Photodimers," In N. S. Allen, Photochemistry and Photophysics of Polymeric Materials, 2010, pp. 209-234.

Patel M.P., et al., "Polymerization Shrinkage of Methacrylate Esters," Biomaterials, 1987, vol. 8 (1), pp. 53-56.

Ramanujam P.S., et al., "Photochromic Processes for High Density Optical Storage," SPIE Proceedings, 2003, vol. 5069, pp. 57-63.

Setlow R.B., "Cyclobutane-type Pyrimidine Dimers in Polynucleotides," Science, 1996, vol. 153 (3734), pp. 379-386.

Theis A., "Synthesis and Kinetic Studies on the Photochemical Behavior of Polymeric Mesoions from Novel Methacrylic Monomers and of Mesoionic Copolymers with Liquid Crystalline Properties," Macromolecules, 2003, vol. 36 (20), pp. 7552-7559.

Martin S., et al., "Smart Polymers Containing Substituted Coumarin Side Groups Enable Photo-Induced uning 29 ffocallength of Intraocular Lenses," Ophthalmic Technologies XX1, 2011, vol. 7885, pp. 8225-6705.

Matos M.J., et al., "Insight into the Interactions between Novel Coumarin Derivatives and Human A3 Adenosine Receptors," chemMedChem, 2014, vol. 9, pp. 2245-22532.

Miyata A., et al., "Clinical and Experimental Observations of Glistening in Acrylic Intraocular Lenses," Japanese Journal of Ophthalmology, 2001, vol. 45(6), pp. 564-569.

Miyata A., et al., "Equilibrium Water Content and Glistenings in Acrylic Intraocular Lenses," Journal of Cataract and Refractive Surgery, 2004, vol. 30(8), pp. 1768-1772.

Moffett R.B., et al., "Azacoumarins," Journal of Organic Chemistry, 1970, vol. 35 (11), pp. 3596-3600.

Nasu S., Preparation of Lamellar Inorganic-Organic Hybrids from Tetraethoxysilane and a Coumarin Derivative Containing a Ttriethoxysilylgroup and Photodimerization of the Interlayer Coumaringroups,“ Journal of Materials Chemistry," 2010, vol. 20, pp. 6688-6695.

Parenti M.D., et al., "Three-Dimensional Quantitative Structure-Activity Relationship Analysis of a set of Plasmodium Falciparum Dihydrofolate Reductase Inhibitors using a Pharmacophore Generation Approach," Journal of Medicinal Chemistry, 2004, vol. 47(17), pp. 4258-4267.

Qin et al., Polymer International, 1999, vol. 48, pp. 491-494.

Rampazzo E., et al., "Surface Modification of Silica Nanoparticles: a New Strategy for the Realization of Self-organized Fluorescence Chemosensors," Journal of Materials Chemistry, 2005, vol. 15 (27-28), pp. 2687-2696.

Sangwan N.K., et al., "4-Alkyl-3-phenyl-2H-1-benzopyran-2-ones and Related Compounds as Potential Pesticides," Indian Journal of Chemistry, 1990, vol. 298, pp. 294-296.

Sato Y., et al., "Studies on New-adrenergic Blocking Agents. I. Syntheses and Pharmacology of Coumarin Derivatives," Chemical and Pharmaceutical Bulletin, 1972, vol. 20 (5), pp. 905-917.

Schmidt G.M.J., "Photodimerization in the Solid State," Pure and Applied Chemistry, 1971, vol. 27, pp. 647-678.

Schraub M., et al., "Smart Polymers Containing Substituted Coumarin Side Groups Enable Photo-induced Tuning of Focal Length of Intraocular Lenses," Ophthalmic Technologies, 2011, vol. 7885, pp. 1-11.

Schraub M., et al., "Photoinduced Refractive Index Changes of 3-phenyl-coumarin Containing Polymers for Ophthalmic Applications," European Polymer Journal, 2014, vol. 51, pp. 21-27.

Schwartz D.M., et al., "Light-adjustable Lens: Development of in Vitro Nomograms," Transactions of the American Ophthalmological Society, Dec. 2004, vol. 102, pp. 67-74.

Skowronski L., et al., "Optical Properties of Coumarins Containing Copolymers," Optical Materials, Sep. 2015, vol. 47, pp. 18-23.

Smith L.E., et al., "Synthesis and Properties of Functional Poly(vinylpyrrolidinone) Hydrogels for Drug Delivery ," Polymers for Biomedical Applications, 2008, vol. 977, pp. 196-203.

Sohn E., et al., "Tuning Surface Properties of Poly(Methyl Methacrylate) Film Using Poly(Perfluoromethyl Methacrylate)s With Short

(56) References Cited

OTHER PUBLICATIONS

Perfluorinated Side Chains," Langmuir: the ACS journal of surfaces and colloids, 2016, vol. 32 (38), pp. 9748-9756.
Suratwala T., et al., "Photostability of Silylated Coumarin Dyes in Polyceram Hosts," Journal of Sol-Gel Science and Technology, 1997, vol. 8(1), pp. 973-978.
Tang E., et al., "A Convenient Solid-Phase Synthesis of Coumarins by TMSOTf-Catalyzed Intramolecular Selene-I 18 rylation ofTethered Alkenes," Synlett, 2012, vol. 23(6), pp. 907-912.
Trager J., et al., "Polymers for in vivo Tuning of Refractive Properties in Intraocular Lenses," Macromolecular Bioscience, 2008, vol. 8, pp. 177-183.
Trecourt F., et al., "Improved Synthesis of 2,3-disubstituted Pyridines by Metallation of 2-chloropyridine: a Convenient Route to Fused Polyheterocycles," Journal of the Chemical Society, Perkin Transactions, 1990, vol. 1 (9), pp. 2409-2415.
Trivedi R.H., et al.," Post Cataract-interocular Lens (IOL) Surgery Opacification," Eye, 2002, vol. 16(3), pp. 217-241.
Truong T., et al., "General Method for Functionalized Polyaryl Synthesis via Aryne Intermediates," Journal of the American Chemical Society, 2014, vol. 136(24), pp. 8568-8576.
Vina D., et al., "8-Substituted 3-Arylcoumarins as Potent and Selective MAO-B Inhibitors: Synthesis, Pharmacological Evaluation, and Docking Studies," ChemMedChem, 2012, vol. 7(3), pp. 464-470.
Waldmann H., et al., "Reagent-Controlled Domino Synthesis of Skeletally-Diverse Compound Collections," Chemical Communications, 2008, vol. 10, pp. 1211-1213.
Wang D, et al., "Strategic Approach to 8-Azacoumarins, " Organic Letters, 2017, vol. 19 (5), pp. 984-987.
Wang J., et al., "Palladium-Catalyzed Regioselective Cross-Coupling Reactions of 3-Bromo-4-tosyloxyquinolin-2(1H)-one with Arylboronic Acids. A Facile and Convenient Route to 3,4-Disubstituted Quinolin-2(1H)-ones," Advanced Synthesis & Catalysis, 2007, vol. 349, pp. 1943-1948.
Wolfbeis O.S, et al., "Darstellung Pyronokondensierter 2-Pyridone, Cumarine and 2-Chinolone mit Hilfe der Kappe-Mayer-Variante der von Pechmann-Reaktion," Monatshefte fur Chemie, 1982, vol. 113, pp. 365-370.
Wu J., et al., "Synthesis of 3,4-Disubstituted Quinolin-2(1H)-ones via Palladium-Catalyzed Regioselective Cross-Coupling Reactions of 3-Bromo-4-trifloxyquinolin-2(1H)-one with Arylboronic Acids," Chemistry Letters, 2005, vol. 34 (4), pp. 550-551.
Wu X., et al., "A General Palladium-Catalyzed Carbonylative Synthesis of Chromenones from Salicylic 20 Idehydes and Benzyl Chlorides," Chemistry : A European Journal, 2013, vol. 19(37), pp. 12245-12248.
You L., et al., "Discovery of Novel Osthole Derivatives as Potential Anti-Breast Cancer Ttreatment," Bioorganic & Medicinal Chemistry Letters, 2010, vol. 20, pp. 7426-7428.
Zhang J., et al., "Enantioselective Phosphine-Catalyzed Allylic Alkylations of Mix-Indene with MBH Carbonates", Organic Letters, 2017, vol. 19(22), pp. 6080-6083.
Arnoldi A., et al., "Analogues of Phytoalexins. Synthesis of Some 3-Phenylcoumarins and Their Fungicidal Activity," Journal of Agricultural and Food Chemistry, 1986, vol. 34(2), pp. 185-188.
Asif., "Overview of Diverse Pharmacological Activities of Substituted Coumarins" Compounds with Therapeutic 33 Potentials, American Journal of Current Organic Chemistry, 2015, vol. 1, 16 pages.
Beaulieu P.L., et al., "Discovery of the First Thumb Pocket 1 NS5B Polymerase Inhibitor (BILB 1941) with Demonstrated Antiviral Activity in Patients Chronically Infected with Genotype 1 Hepatitis C Virus (HCV)," Journal of Medicinal Chemistry, 2012, vol. 55(17), pp. 7650-7666.
Behm H., et al., "NOTE Crystal and Molecular Structure of a Photo Dimer of 1 ,2-dihydro 3-phenylnaphthalene, C32H28,"Journal of Crystallographic and Spectroscopic Research, 1988, vol. 18(4), pp. 471-475.
Billeret D., et al., "Convenient Synthesis of 5-Azacoumarins," Journal of Heterocyclic Chemistry, 1993, vol. 30, pp. 671-674.
Bonnetaud D, et al., "Synthesis of Formyl-3 Hydroxy-2 Pyridine and 2H-Pyrano[2,3-b] Pyridines One-2 (1)," Journal Heterocycl. Chemistry, Feb. 1972, vol. 9 (1), pp. 165-166.
Bozukova D., et al., "Polymers in Modem Ophthalmic Implants -Historical Background and Recent Advances," Materials Science and Engineering R, 2010, vol. 69(6), pp. 63-83.
Bratcher M.S., et al., "Synthesis of Bifunctional Photorefreactive Polymers with Net Gain: Design Strategy Amenable to Combinatorial Optimization," Journal of the American Chemical Society, 1998, vol. 120, pp. 9680-9681.
Brufola G., et al, "Efficient One-Pot Synthesis of 7-Azacoumarins by Knoevenagel Reaction Using Water as Reaction Medium," Heterocycles, 1997, vol. 45 (9), pp. 1715-1721.
Buquet A., et al., "Photoreactivite de Systemes Hexatrieniques Heterocycliques. Aryl-2 et 3 Benzo[b]thiophene," Tetrahedron, 1981, vol. 37, pp. 75-81.
Carrer A., et al., "Synthesis of 3,4-Disubstituted Quinolin-2-(1H)-Ones via Palladium-Catalyzed Decarboxylative Arylation Reactions," Advanced Synthesis & Catalysis, 2013, vol. 355, pp. 2044-2054.
Chen K., et al., "Synthesis of Novel Polymer/Urea Peptoid Conjugates Using RAFT Polymerization," Maromolecules, 2010, vol. 43(3), pp. 1341-1348.
Cheng J., et al., "Discovery and Structure-Activity Relationship of Coumarin Derivatives as TNF-α Inhibitors," Bioorganic & Medicinal Chemistry Letters, 2004, vol. 14, pp. 2411-2415.
Cowie J.M.G., "Polymers: Chemistry & Physics of Modern Materials," 2nd Edition, Blackie, Glasgow, 1991, 10 pages.
Database Registry, STN International CAS Registry No. 1105244-13-0, Mar. 13, 2010.
Database Registry, STN International CAS Registry No. 1211903-13-0, Mar. 19, 2010.
Database Registry, STN International CAS Registry No. 1211936-26-3, Mar. 19, 2010.
Database Registry, STN International CAS Registry No. 1212764-88-9, Mar. 21, 2010.
Database Registry, STN International CAS Registry No. 1212785-02-8, Mar. 21, 2010.
Database Registry, STN International CAS Registry No. 376382-75-1, Dec. 18, 2001, CAS Registry No. 376380-44-8, Dec. 18, 2001, CAS Registry No. 376378-98-2, Dec. 18, 2001.
David L.O., et al., "Photochemical Dimerization Reactions of N-Acylindoles," Tetrahedron Letters, 1993, vol. 34(7), pp. 1087-1090.
Degorce S.L., et al., "Investigation of { E )-3-[4-{2-0xo-3-aryl-chromen-4-yl)oxyphenyl[acrylic Acids as ral Selective Estrogen Receptor Down-Regulators," Journal of Medicinal Chemistry, 2015, vol. 58(8), pp. 3522-3533.
Desai S.M., et al., "Synthesis of 3-Substituted-aminopropoxy-2-hydroxycoumarin Derivatives as Possible B-Blockers," Journal of the Indian Chemical Society, Jun. 1989, vol. 66 (6), pp. 415-417.
Duguet E., et al., "New Cyclodisilazane Monomers," Journal of Organometallic Chemistry, 1993, vol. 458(1-2), pp. 9-12.
Fang J., et al., "Synthesis and Photodimerization in Self-assembled Monolayers of 7-(8-trimethoxysilyloctyloxy) Coumarin," Journal Materials Chemistry, 2001, vol. 11, pp. 2992-2995.
Federal Register, vol. 76 (27), Feb. 9, 2011, pp. 7166.
Fiilipenko., et al., "Effect of Intermolecular Interactions on the Formation of Mesophases in 3-aryl 7 Substituted Coumarins, and the Crystal Structure of 3-(4?-butyl)- and (4?-heptylphenyl)-7-propoxycoumarins," Bulletin of the Cademy of Sciences of the USSR, 1989, vol. 38(10), pp. 2073-2079.
Garazd M.M., et al., "Modified Coumarins. I. Synthesis of 5-phenyl-7h-furo[2, 3-g]chromen-7-ones and 9-phenyl-7h-furo-[2, 3-f]chromen-7-ones, " Chemistry of Natural Compounds, 2000, vol. 36 (5), pp. 478-484.
Garazd M.M., et al., "Modified Coumarins. 29. Synthesis of Structural Analogs of Natural 6-arylfuro[3,2-g]chromen-7-ones, " Chemistry of Natural Compounds, 2009, vol. 45 (2), pp. 158-163.
Garazd M.M., et al., "Modified Coumarins. 8. Synthesis of Substituted 5-(4-methoxyphenyl)-7h-furo[3,2-g]chromen-7-ones," Chemistry of Natural Compounds, 2002, vol. 38 (6), pp. 539-548.

(56) References Cited

OTHER PUBLICATIONS

Gordeeva N.A., et al., "Photochemical Reactions of 7-Aminocoumarins Methyl-7-Diethylaminocoumarin with Monosubstituted Benzenes," Chemistry of 27 Heterocyclic Compounds, 1990, pp. 976-980.
Ikeda M., et al., "Effect of Microcrystalline Cellulose on the Stability of Oxazolam in Solid State," Journal of Pharmaceutical Science and Technology, 1987, vol. 47 (4), pp. 204-210.
IUPAC, Glossary of Basic terms in polymer Science, Pure and Applied Chemistry, 1996, vol. 68, pp. 2291.
Jafarpour F., et al., "Palladium-Catalyzed Decarboxylative Cross-Coupling Reactions: A Route for 26 Regioselective Functionalization of Coumarins," The Journal of Organic Chemistry, 2013, vol. 78(7), pp. 2957-2964.
Jenkins A.D., "Glossary of basic Terms in Polymer Science," Pure Applied Chermistry, 1996, vol. 68(12), pp. 2287-2311.
Kano S., et al., "A Facile Synthesis of 4-Phenylcarbostyrils and 4-Phenylisocarbostyril Involving Photocyclization of Benzo [b]thiophene-2-carboxanilidines and 2-Benzoylamino-3-chlorobenzo[b]thiophene," Heterocycles, 1979, vol. 12 (4), pp. 489-492.
Kapoor., et al., "Synthesis of Coumarins," Labdev, 1966, vol. 4(1), pp. 27-29.
Keijzer F., et al., "Photoacoustic Determination of the Photostability of 3-phenyl-1 ,2-dihydronaphthalene," Journal of Photochemistry and Photobiology A: Chemistry, 1990, vol. 50(3), pp. 401-406.
Kienast A., et al., "Influence of a New Surface Modification of Intraocular Lenses With Fluoroalkylsilan on the Adherence of Endophthalmitis-causing Bacteria in Vitro," Graefe's Archive for Clinical and Experimental Ophthalmology, 2006, vol. 244(9), pp. 1171-1177.
Korchia L., et al., "UV-Responsive Amphiphilic Graft Copolymers based on Coumarin and Polyoxazoline," Soft Matter, Jan. 2017, vol. 13(25), pp. 4507-4519.
Krauch C.H., et al., "Photochemische C4- und C3O-Cycloadditionen an Cumaron," Chemische Berichte, 1966, vol. 99(5), pp. 1723-1731.
Krejcoves J., et al., "The Use of Coumarin Derivatives in the Preparation of Fluorescence-labelled Poly [N-(2-hydroxypropyl)methacrylamide]," Collection of Czechoslovak Chemical Communications, 1980, vol. 45(3), pp. 727-731.
Kurosawa T., et al., "Analysis of Stereoisomeric C27-Bile Acids by High Performance Liquid Chromatography with Fluorescence Detection," Journal of Pharmaceutical and Biomedical Analysis, 1997, vol. 15(9-10), pp. 1375-1382.
Lamberts J.J.M., et al., "The Photochemistry of 1-3- and 4-phenyl-substituted 1,2 Dihydronaphthalenes," Recueil, Journal of the Royal Netherlands Chemical Society, 1984, vol. 103(4), pp. 131-135.
Lee M.S., et al., "Photodependent Release from Poly(vinyl alcohol)/ Epoxypropoxy Coumarin Hydrogels," Journal of Applied Polymer Science, 2012, vol. 124, pp. 4339-4345.
Legeais J.M., et al., "In Vivo Study of a Fluorocarbon Polymer-Coated Intraocular Lens in a Rabbit Model," Journal of Cataract and Refractive Surgery, 1998, vol. 24(3), pp. 371-379.
Li M., et al., "Evaluation of Vinylsulfamides as Sulfhydryl Selective Alkylation Reagents in Protein Modification," A Bioorganic & Medicinal Chemistry Letters, 2003, pp. 383-386.
Liao J.H., et al., "Anti-UVC Irradiation and Metal Chelation Properties of 6-Benzoyl-5,7-dihydroxy-4-phenyl-16 hromen-2-0ne: An Implication for Anti-Cataract Agent," International Journal of Molecular Sciences, 2011, vol. 12, pp. 7059-7076.
Lin W., et al., "Through-Bond Energy Transfer Cassettes With Minimal Spectral Overlap Between the Donor Emission and Acceptor Absorption: Coumarin-rhodamine Dyads With Large Pseudo-Stokes Shifts and Emission Shifts," Angewandte Chemie, 2010, vol. 49(2), pp. 375-379.
Lunazzi L., et al., "Stereomutation of Axially Chiral Aryl Coumarins," The Journal of Organic Chemistry, 2010, vol. 75 (17), pp. 5927-5933.
Inal S., et al., "Temperature-Regulated Fluorescence and Association of an Oligo(ethyleneglycol)methacrylate-Based Copolymer with a Conjugated Polyelectrolyte—The Effect of Solution Ionic Strength," The Journal of Physical Chemistry, Nov. 2013, vol. 117, pp. 14576-14587.
Inal S., et al., "Temperature-Regulated Fluorescence Characteristics of Supramolecular Assemblies Formed By a Smart Polymer and a Conjugated Polyelectrolyte," Macromolecular Chemistry and Physics, 2013, vol. 214, pp. 435-445.
Ji., et al., "Facile Synthesis of 3-Arylindenes by HMPA-Promoted Direct Arylation of Indenes with Aryl Fluorides," ACS Omega, vol. 3(8), pp. 10099-10106, 2018.
Yonezawa et al., Thermal Behavior of Head-to-head Coumarin Dimers and Their Lactone-opened Dervatives, Bulletin of the Chemical Society of Japan, vol. 57, No. 06, pp. 1608-1611, Jun. 1984.
Rao et al., "Uber Die Photocyclodimerisation Substituierter Cumarine", Chemische Berichte, vol. 106, No. 02, pp. 388-395, 1973.
Wolff et al., "Photodimerization of Coumarin Revisited: Effects of Solvent Polarity on the Triplet Reactivity and Product Pattern", Physical Chemistry Chemical Physics, vol. 06, pp. 368-376, 2004.

* cited by examiner

SYSTEM AND METHOD FOR IRRADIATING AN ARTIFICIAL LENS

FIELD OF THE INVENTION

The present invention generally relates to a system for two-photon or multi-photon irradiating an artificial lens, preferably an intraocular lens preferably arranged within an eye of a patient and a method for locally adjusting a polarizability and/or a refractive index of an artificial lens preferably an intraocular lens preferably arranged within an eye of a patient. The method relates in particular to fabrication of optical profiles by adjusting polarizability through two- or multi-photon processes in a non-destructive manner.

BACKGROUND OF THE INVENTION

Light-induced change of material properties is applied in several technical fields like micromachining, 3D-printing, nano-structuring or two-photon lithography. Different processes can hereby occur, such as photopolymerization, light-induced material degradation or photochemical crosslinking. The result of these processes is a change of the properties of the irradiated material. This can be a change of mechanical properties, solubility, transparency, refractive index or others.

In 3D-printing—usually photolithographic approaches—a femtosecond laser may be used to polymerize a specific array. This may be done by a photopolymerization reaction. To make this formulation curable, a photosensitizer may be added. This may allow for printing in μm-resolution which may not be possible by common 3D-printing techniques. Multi-beam arrays may be used in order to increase manufacturing speed.

Nano-structuring is also used in the biomedical field. In the field of eye care, structuring applications are used to modify ophthalmic polymers (like contact lenses or intraocular lenses (IOLs)) and ocular tissue (see, for example, US 2018243082 A1). When treating IOLs, usually a photosensitizer in the material is utilized, for example, by absorbing UV light. Two or more photon processes may allow for targeting voxels in the inner material without influencing the surface of the IOL. When being irradiated, the photosensitizer may absorb the light and deliver the energy to the surrounding material. In WO2017221068 A1, emitted light is provided in the form of heat to a hydrogel material. This may result in a degradation of the polymer and a change of refractive index. Another approach is the formation of non-vision decreasing crystallites in the material by femtosecond-laser irradiation. The higher molecular order of the crystallites may lead to a local increase of density in the material, resulting in a local increase of the refractive index, as shown in US 2010228345 A1.

US2009143858 describes a method for modifying the refractive index of an optical, polymeric material comprising irradiating select regions of the optical, polymeric material in a destructive manner with a focused, visible or near-IR laser having a pulse energy from 0.05 nJ to 1000 nJ resulting in the formation of refractive optical structures. Said refractive optical structures are characterized by a change in refractive index, by exhibiting little or no scattering loss, and exhibiting no significant differences in the Raman spectrum with respect to the non-irradiated optical, polymeric material used.

US2016081852 describes a method of altering the refractive properties of the eye, the method including applying a photosensitizer to interior tissue of a cornea of an eye, the photosensitizer facilitating cross-linking of the interior tissue of the cornea, irradiating the cornea so as to activate cross-linkers in the interior tissue of the cornea, and altering the cornea so as to change the refractive properties of the eye.

US2008004610 describes specific refractive index-adjustable lenses and in-procedure refractive index measurements by a refractometer. The adjustments described are in a destructive manner.

Cataract is a clouding of the lens of the eye which may impede the passage of light. Most cases of cataract are related to the aging process. However, children may be born with a cataract or develop it at an early age. Furthermore, a cataract may develop after eye injuries, inflammation, or some other eye diseases. According to studies of the World Health Organization, more than 50 million people currently suffer from cataract worldwide, which makes cataract the cause for about half of all worldwide cases of blindness. While cataracts may be surgically removed, in many countries surgical services are not available, and cataract remains the leading cause of blindness. As the average life expectancy, the number of people suffering from cataract is growing. Cataract is thus an important cause of bad vision in both developed and developing countries. Comprehensive prevention of cataract development is not known yet.

Sight may be successfully restored when treating cataract in an operation. The opaque lens is hereby removed and replaced by an artificial lens. Artificial lenses are implanted as every modern lens through a small incision and after removal of the natural lens into the remaining capsular bag or if the capsular bag is lost, into the sulcus.

A typical problem related to the implantation of an IOL is that the result obtained, as far as optimal vision is regarded, is far less than optimal in most cases. Biometric data of the eye before IOL implantation, among them curvature radii of the cornea and length of the eye-ball, cannot be determined with the desired precision. Positioning of the IOL during surgery, unpredictable effects from wound healing, and post-operative migration of the IOL occurring within weeks and months after cataract surgery are currently difficult to predict. There is a large variety of approaches and formulas used to predict the IOL power before cataract surgery, but an adequate solution has not yet been found.

Clinical trials which deal with the outcome of cataract surgeries have shown that more than 80% of patients are within 1 diopter (D) of the desired refraction. Nevertheless, many have refractive errors and some correction is therefore required in order to provide for optimized vision. It has been shown that refractive errors after cataract surgery are practically unavoidable even though the magnitude of the refraction error has been reduced. Problems may also arise if certain conditions of the eye exist, for example, if the axial length of the eye is significantly longer or shorter than average. Pediatric cases are generally prone to complications associated with refractive power prediction. Intraocular lens power errors due to production tolerances may also contribute to the total error, particularly for high-power IOLs. It is hereby to be noted that the applicable ISO 11979 standard allows tolerances of ±0.33 D in the corneal plane for an IOL above 25.00 D and even ±0.66 D for an IOL above 30.00 D.

A refractive error is defined as an error in the ability to focus light by the eye and is a frequent reason for reduced visual acuity. An eye having no refractive error when viewing a distant object is emmetropic.

An eye with a refractive error when distant objects are being viewed is said to be ametropic.

Refractive errors may be categorized as spherical and cylindrical. Spherical errors occur when the optical power of the eye is either too large or too small to focus light on the retina. Cylindrical errors occur when the curvature on the two meridians differ. People suffering from a refraction error have blurry vision.

Myopia, also called near- or short-sightedness, relates to a refractive defect of the eye in which collimated light produces an image focus in front of the retina when the eye is in a relaxed state. People with myopia see nearby objects clearly, while distant objects appear blurred. With myopia, the eyeball is too long, or the cornea is too steep, i.e. the optics is too powerful for the length of the eyeball. As a result, images are focused in the vitreous inside of the eye rather than on the retina.

Hyperopia, also known as farsightedness or long-sightedness, relates to a defect of vision caused by an imperfection in the eye. Optics which is too weak for a particular length of the eyeball may cause inability to focus on near objects. In extreme cases, a person may be unable to focus on objects at any distance. As an object moves toward the eye, the eye must increase its optical power to keep the image in focus on the retina. If the power of the cornea and lens is insufficient, as in hyperopia, the image appears blurred.

Astigmatism is an optical defect in which vision may be blurred due to the inability of the optics of the eye to focus a point object into a sharp focused image on the retina. An irregular or toric curvature of the cornea or lens may be the cause for astigmatism. There is a difference in the degree of curvature refraction of the two different meridians. In other words, the eye has different focal points in different planes. For example, the image may be clearly focused on the retina in the horizontal plane, but not in front of the retina in the vertical plane. People may the see contours of a particular orientation as blurred, but contours with orientations at right angles may be seen clearly. It may be difficult for people suffering from astigmatism to see fine details. In some cases, vertical lines (e.g. walls) may appear tilted to the patient. Astigmatic optics may often be corrected by spectacles, hard contact lenses or contact lenses that have a compensating optic.

There are about six different forms of cataract with more than twenty reasons identified that could lead to a cataract. Once cataract is diagnosed, drug treatment is therefore currently not possible. The only current treatment is the replacement of the natural lens, followed by implanting an artificial IOL. Nowadays the standard of care is a foldable IOL.

The IOL may hereby be immersed in the liquid of the eye chambers. The optically effective part of the IOL typically has a diameter between 5 mm and a maximum of 7 mm. Elastic loops or brackets are attached at the edges of the optic part of the IOL depending on the particular model. These loops, which are called the haptics, allow for centering the lens in the capsular bag and for holding the IOL in place. The overall diameter of an IOL is about 12 mm, its thickness is dependent on its refraction power and normally varies between 0.7 mm and a maximum of 2 mm. The weight of an IOL is on the order of 50 mg.

Polymers which may be used to fabricate foldable IOLs may be divided into two subgroups. The IOLs may either be made of (1) acrylic or methacrylic or (2) of silicone based polymers. Furthermore, hydrophobic and hydrophilic materials may be used for IOLs. Hydrophilic materials may utilize a water uptake of about 10-30% to become soft, while the hydrophobic materials may be designed to be soft without a water uptake. Many variations of IOL's and many IOL's with different optical profiles (like multifocal, toric, extended depth of focus) have been studied and marketed. However, it is currently difficult to determine biometric data with the required precision for IOLs to provide the promised outcome.

Examples of silicon-containing polymers that can be used as optical materials are described in WO2018149857.

Examples of acrylate-containing or methacrylate-containing polymers that can be used as optical materials are described in WO2017032442, WO2017032443, WO2017032444, WO2018149850, WO2018149852, WO2018149853, WO2018149855 and WO2018149856.

The [2+2]-cycloaddition reaction between e.g. coumarins can be conducted with light. One coumarin is photo-chemically excited and able to react with a ground state molecule in its range. According to the Jablonski diagram, the absorption of photons brings organic molecules to an excited singlet state. This can be transformed into a triplet state via intersystem crossing. In contrast to the singlet state, which can be depopulated by fluorescence, the triplet state can only depopulate by nonradiative decay. The lifetime of the triplet state in organic molecules like coumarins is therefore much longer than the singlet state. For the intermolecular [2+2]-cycloaddition reaction of coumarins, the triplet state and its population is therefore most relevant [T. Wolff et al, Phys. Chem. Chem. Phys., 2004, 6, 368-376] as its long lifetime allows for numerous collisions with other molecules and a high special mobility leading to a higher probability of a cyclodimerization reaction.

Aside from the errors due to the measurement of biometric data, exact prediction of the refraction after operation/surgery is almost impossible. This is mainly due to unpredictable effects which may occur during the healing process within the weeks or months following the cataract surgery. These effects include, for example, effects on the pseudophakic anterior chamber depth, which is the notional distance between the vertex of the cornea and the effective principal surface of the IOL. Furthermore, changes in the cornea shape may occur during the healing process. The exact value of those changes may depend on a variety of factors including originalities of the eye, the IOL type, as well as the surgeon and the instruments utilized. Uncertainties in the specifications of the IOL may also make it difficult to predict the correct refractivity.

After wound healing, the treatment, meaning adjustment of optical profiles of the IOL, may be individually applied or patients treated with IOLs may need prescription eyewear for ideal vision.

Alternatively, patients may need an adapted contact lens for ideal vision correcting vision of the natural lens.

Since there are shortcomings in preoperative IOL refractive power prediction which cannot currently be overcome, an aim of systems and methods according to the present disclosure is to provide a solution for non-invasively adjusting optical profiles of an already implanted IOL by changing the polarizability of organic molecules out of which the IOL is made. Furthermore, an aim of the systems and methods according to the present disclosure is to provide a solution for preparing and/or modifying an artificial lens (which may or may not be arranged within an eye of a patient), in particular modifying a polarizability of the artificial lens, particularly by using a two-photon (or generally multi-photon) process.

Multi-photon excitation is a non-linear phenomenon requiring high intensities in order to enable the simultaneous absorption of photons. In case of two-photon excitation, the excitation occurs at a probability proportional to the square of the intensity of the excitation light. On the other hand, excitation light collected by a microscope objective lens has a light intensity that is inversely proportional to the square of the distance from the focal plane.

N. Yonezawa et al, Bull. Chem. Soc. Jpn., 1984, 57, 1608-1611 describes that heat has been shown to induce a thermal cycloreversion reaction which impacts negatively the yield of formed cyclodimers from the photoreaction.

SUMMARY OF THE INVENTION

The present inventors have now found that the above objects may be attained either individually or in any combination by the system and processes of the present application.

The invention relates to a system for irradiating an artificial lens, the system comprising:

- one or more irradiation sources for two-photon or multi-photon irradiating a said artificial lens with an irradiation beam focused with an optic and of a first wavelength and/or a second wavelength different from the first wavelength,
- a scanner coupled to the one or more irradiation sources and configured to scan a said irradiation beam across said artificial lens, and
- an input unit coupled to the one or more irradiation sources and the scanner, wherein the input unit is configured to input data for treating said artificial lens by scanning a said irradiation beam across said artificial lens based on the input data, and
- wherein the first wavelength is between 600 nm and 800 nm for locally decreasing, based on said treating of said artificial lens, a polarizability of said artificial lens, and wherein the second wavelength is between 400 nm and 590 nm for locally increasing, based on said treating of said artificial lens, the polarizability of said artificial lens.

The invention further relates to a system for irradiating an artificial lens preferably arranged within an eye of a patient, the system comprising:

- one or more irradiation sources for two-photon or multi-photon irradiating a said artificial lens with an irradiation beam focused with an optic and of a wavelength between 600 nm and 800 nm,
- a scanner coupled to the one or more irradiation sources and configured to scan a said irradiation beam across said artificial lens, and
- an input unit coupled to the one or more irradiation sources and the scanner, wherein the input unit is configured to input data for treating said artificial lens by scanning a said irradiation beam across said artificial lens based on the input data, and
- wherein said wavelength is for locally decreasing, based on said treating of said artificial lens, a polarizability of said artificial lens.

The invention further relates to a system for irradiating an artificial lens preferably arranged within an eye of a patient, the system comprising:

- one or more irradiation sources for two-photon or multi-photon irradiating a said artificial lens with an irradiation beam focused with an optic and of a wavelength between 400 nm and 590 nm,
- a scanner coupled to the one or more irradiation sources and configured to scan a said irradiation beam across said artificial lens, and
- an input unit coupled to the one or more irradiation sources and the scanner, wherein the input unit is configured to input data for treating said artificial lens by scanning a said irradiation beam across said artificial lens based on the input data, and
- wherein said wavelength is for locally increasing, based on said treating of said artificial lens, the polarizability of said artificial lens.

FIGS. 1 and 2 show a schematic illustration of a system as described before.

FIG. 1 is a schematic illustration of a system for the irradiation of an artificial lens, e.g. a contact lens or an intraocular lens not arranged within an eye of a patient. The irradiation beam (2) emitted by the irradiation source (1) is deflected by the scanner (4) and focused by the optic (16) to perform the desired adjustments of polarizability of the artificial lens (3). The positioning system (20) determines the working position of the focal spot inside the artificial lens (3). Together with the power and the existing optical profile of the artificial lens (3), the positioning information is part of the input data (8) associated with the artificial lens (3). Lens data (10) and treatment plan data (12) are described further below. The temperature management unit (14) predicts and/or measures the temperature in the material of the artificial lens (3) before and/or during irradiation.

FIG. 2 is a schematic illustration of a system for the irradiation of an intraocular lens arranged within an eye of a patient.

FIG. 2 is a schematic illustration of a system for the irradiation of an intraocular lens arranged within an eye of a patient. The irradiation beam (2) emitted by the irradiation source (1) is deflected by the scanner (4) and focused by the optic (16) to perform the desired adjustments of polarizability of the artificial lens (3) within the eye of the patient, said optic (16) being linked to an eye interface system (18) that keeps the eye of the patient in a fixed position. The positioning system (20) determines the working position of the focal spot inside the artificial lens (3). Together with the power and the existing optical profile of the artificial lens (3), the positioning information is part of the input data (8) associated with the artificial lens (3). Lens data (10) and treatment plan data (12) are described further below. The temperature management unit (14) predicts and/or measures the temperature in the material of the artificial lens (3) before and/or during irradiation.

The invention further relates to a process for adjusting a polarizability of an artificial lens comprising a body formed of a polymeric optical material based on a two- or multi-photon absorption process, the process comprising the steps of:

- providing said lens; and
- adjusting the polarizability of said lens through irradiation of said lens by using a system according to the invention as described before or preferably described below thereupon changing the polymeric optical material with significant differences in the UV/Vis spectrum with respect to the non-irradiated polymeric optical material of the artificial lens.

The invention further relates to a method for locally adjusting a polarizability of an intraocular lens comprising a polymerized optical material arranged within an eye of a patient, the method comprising:

- exposing the intraocular lens to an irradiation beam having a wavelength between 600 nm and 800 nm to locally decrease the polarizability of the intraocular lens or exposing the intraocular lens to an irradiation beam having a wavelength between 400 nm and 590 nm to locally increase the polarizability of the intraocular lens.

The invention is furthermore related to a method for correcting vision in a patient by modifying the refractive index of an intraocular lens within the eye of said patient comprising identifying and measuring the degree of vision correction of the patient;

determining the position and type of refractive structures to be written into said intraocular lens to correct the patient's vision; and subsequently exposing said intraocular lens to two-photon or multi-photon irradiation having a wavelength between 600 nm and 800 nm to locally decrease the polarizability of the intraocular lens or exposing said intraocular lens or subsequently exposing said intraocular lens to two-photon or multi-photon irradiation having a wavelength between 400 nm and 590 nm to locally increase the polarizability of the intraocular lens.

The invention further relates to a kit of parts comprising a system as described before or preferably described below and at least one artificial lens to be suited for said system.

DETAILED DESCRIPTION OF THE INVENTION

It is to be noted that, throughout the present disclosure, any references as to an entity/component/part of the system being coupled to another entity/component/part (and potentially further entities/components/parts) may entail the one entity/component/part being directly and/or indirectly coupled to the other entity/component/part.

The lens or artificial lens within said disclosure is defined to be a contact lens or intraocular lens. Intraocular lenses according to the invention are implantable lenses that are used to replace the natural lenses of the eyes when they have become damaged.

The type of lens is not restricted and may comprise a contact lens or an intraocular lens. Most preferably, such artificial lens is an intraocular lens (IOL), which may, for example, be a posterior chamber intraocular lens or an anterior chamber intraocular lens.

The type of intraocular lens is not limited in any way. It may, for example, be a pseudo-phakic intraocular lens or a phakic intraocular lens. The former type replaces the eye's natural, crystalline lens, usually to replace a cataractous lens that has been removed. The latter type is used to supplement an existing lens and functions as a permanent corrective lens, which is implanted in the anterior or posterior chamber to correct refractive errors of the eye. The artificial lens to be treated according to the invention may, for example, comprise one or more optic and one or more haptic components, wherein the one or more optic components serve as lens and the one or more haptic components are attached to the one or more optic components and hold the one or more optic components in place in the eye. The artificial lens to be treated according to the invention may be of a one-piece design or of multi-piece design, depending on whether the one or more optic components and the one or more haptic components are formed from a single piece of material (one-piece design) or are made separately and then combined (multi-piece design).

The artificial lens, preferably the IOL, may be comprised of a polymerized optical material, whereby optical properties of said lens may be changed with the system non-invasively. The system may be used to change the polarizability and hence the refractive index, in particular based on a multi-photon process.

Preferably, the artificial lens (contact lens or IOL) is comprised of a polymerized optical material as further preferably described below, whereby optical properties of the IOL may be changed with the system non-invasively.

Particular preferably, the artificial lens (contact lens or IOL) consists of a polymerized optical material as further preferably described below. Typically, the optic of a lens is 5 mm to 7 mm in diameter and typically between 0.2 mm and 2.0 mm thick.

In the present application, input data are all kinds of data used for creating the treatment plan which is defined as the translation of the ophthalmic need into control commands for the writing process as further described in detail in the following description. During the writing process the optical pattern is written by irradiation in the artificial lens.

The term "control commands" refers to commands directly controlling the process of writing as defined before or preferably described below. A control command may control e.g. the movement of the scanner.

The term "scanner" used within the description is not part of the input unit according to the invention. The "scanner" as described herein is a component of the system according to the invention which controls the movement of the irradiation beam.

The ophthalmic need refers to the desired optical profile which has to be created in the artificial lens through the system and process according to the invention.

The optical profile is the needed change defined by the surgeon according to the patient's examination results before or after the artificial lens is implanted; for example but not limiting to a spherical full diopter change, a toric profile, an EDOF profile or a bi-, tri- or multifocal profile. Alternatively, the optical profile is the optical property adjustment of the contact lens.

The optical pattern is the necessary change of polarizability resulting in change of refractive index in every voxel of the artificial lens.

The input data as defined before are intended to include common input data, individual input data or in-process input data.

Common input data are intended to include general data used by default due to systemic reasons. Examples of such common input data are described below.

Individual input data are all data related exclusively to the ophthalmic need. Examples of such individual input data are described below.

In-process input data are data created and used during the writing process.

The term "positioning system" as used within the description determines the position of the laser focus in the eye.

The term "locating system" as part of the positioning system as used within the description determines the position of the artificial lens in relation to the system and the patient's eye.

The term "irradiation beam" outlet defines the position where the irradiation beam leaves the optic of the system according to the invention.

The term "optic" as used herein as a part of the system according to the invention includes all optical equipment necessary to control the spatial distribution of the irradiation source (focus) on the artificial lens. Critical parameters of the focus include the lateral focus size (or beam waist) and the focus length (or Rayleigh range). The optic comprises all elements along the optical beam path that determine the focus, such as beam expanders, aperture stops, shutter and in particular the focusing optics, such as a microscope objective or a single aspherical lens.

Irradiation within the focal volume results in refractive optical structures characterized by a change in polarizability/refractive index relative to the polarizability/index of refraction of the bulk of the artificial lens or alternatively the non-irradiated portion of said artificial lens. The change in polarizability/refractive index can in other words be used to form patterned desired refractive structures in the artificial lens which is described or preferably described below.

It is preferred to provide refractive structures that exhibit a change in refractive index, and exhibit little or no scattering loss in such a way that ablation, removal or destruction of the intraocular lens material is not observed in the irradiated region. The irradiated regions described before can take the form of two- or three-dimensional, area or volume filled refractive structures that can provide spherical, aspherical, toroidal, or cylindrical correction. In fact, any optical structure can be formed to yield refractive power correction in both physical directions. Moreover, the optical structures can be stacked vertically or written in separate planes in the artificial lens which is described further below to act as a single lens element.

Multi-photon excitation occurs only in the vicinity of the focal point and preferably by employing ultra-short laser pulses. The average power is limited by the sample damage threshold such threshold being part of the common input data as defined before and below.

The system as described before or preferably described below advantageously allows for post-operative and non-invasive adjustment of optical properties/profiles of an implanted IOL to remove visual impairments such as refractive errors. Furthermore, when manufacturing the artificial lens (e.g. the contact lens or e.g. prior to inserting an intraocular lens into the eye of a patient), the system advantageously allows for a gentle preparation of the artificial lens so as to in particular allow for refractive structures that can provide spherical, aspherical, toroidal, or cylindrical correction and/or maintaining flexibility of the lens once preparation of the lens is completed. The polarizability of the artificial lens is modified based on a two-photon (or generally multi-photon) process which allows adjustment of optical properties/profiles of said artificial lens or which allows adjustment of optical properties in different planes of the artificial lens. Furthermore, the modification of polarizability based on a two-photon or multi-photon process allows for improved maintaining of flexibility of the lens when treated with wavelength of 400 nm to 590 nm. Said artificial lens is preferably an IOL.

Criteria for the Selection and Optimization of System Parameters:

One ultimate purpose of this invention is to generate localized refractive-index modification of IOLs post-implantation as prescribed by the physician to improve the visual acuity of the patient. A crucial criterion for the procedure of refractive-index modification is the total treatment time required to obtain the desired result. It is generally recognized that such procedure should not take more than a few minutes in order to be recognized as viable. The systems capable of localized refractive-index modifications of the state of the art do not include an approach to obtain practical treatment times for IOL applications.

Discussion of System Tradeoffs and Limitations:

For a practical high-performing system capable of adjusting artificial lenses in general or specifically IOLs after implantation it is recognized that its subcomponents have to be treated as a system and must therefore be optimized jointly as many interdependencies and tradeoffs between the subcomponents exist. The subcomponents include the irradiation source, the optic, the scanner and treatment plan.

A key requirement of any system/parameter optimization is to stay within safe limits for the lens material in case of the treatment of an artificial lens being a contact lens, or the lens material and the eye with its components (e.g. retina) in case of the treatment of an artificial lens being an IOL. Such requirements build the basis for common input data as described before. In particular, two main damage mechanisms for radiation from an irradiation source, preferably a pulsed laser source can be distinguished: Single-pulse damage (dielectric breakdown and avalanche breakdown), and thermal damage, where the temperature of the lens material and/or the eye is heated up subsequently for repeated pulses to the same volume. For example: the average power of a pulsed irradiation source relates to the heating and therefore to the potential damage of the lens material and/or the eye. Therefore, while keeping the average power of the irradiation source below the threshold of overheating the lens material and/or eye, pulse energy and pulse repetition rate are inversely related product of pulse energy and number of pulses per second (=inverse of repetition rate) is equal to the average power.

Average power is defined as pulse energy multiplied by number of pulses per second) and is characterized by Watt (W).

Irradiance is equal to flux density) ($W/cm^2$).

Radiant exposure is equal to fluence) ($J/cm^2$).

One overall objective is to minimize the treatment time for an IOL adjustment after implantation. In theory, higher and higher pulse energies with more frequent pulses (=higher repetition rate) could be applied, however, above an average power of typically 1 Watt, overheating starts creating unsafe conditions for IOL material and retina. Therefore, in order to stay within safe operating limits, while completing a treatment of the full IOL volume in a few minutes, one can define a preferred radiant exposure. The preferred radiant exposure is $\leq 5$ $kJ/cm^2$, particular preferably $<1$ $kJ/cm^2$ and very particular preferably $<0.3$ $kJ/cm^2$. This described radiant exposure applies additionally to the processes and methods according to the invention as further described below.

For the case a treatment plan is too extensive and would exceed the limits of laser safety concerning overheating, it is possible to interrupt the treatment to allow a cool down of all by the treatment affected artificial lens material and tissues. After the cool-down the locating system can compare the treated voxel in the artificial lens with the optical pattern and the treatment can be continued.

The process of adjustment of optical properties/profiles of said artificial lens through the system and with requirements as described before will be done according to a treatment plan as described before. According to a treatment plan, profiles for e.g. toric, spheric, multifocal or EDOF (extended depth of focus) can be written into the lens. An algorithm may be utilized to write in profiles for e.g. toric, spheric, multifocal or EDOF (extended depth of focus) profiles.

By combining the information of the desired optical profile together with common and individual input data, the needed optical pattern and the control commands for irradiation source, optics and scanner of the system as described before or preferably described below can be calculated. Individual input data are for example lens data as such as the needed laser-energy for a certain refractive index change per voxel of said artificial lens material, and further patient data as the exact position and orientation of the artificial lens in the patient's eye being part of the treatment plan data.

The control commands can be updated and modified during the writing process by in-process input data such as temperature data of the patient's eye by e.g. IR-temperature measurements, in-process positioning data of the irradiation beam, the artificial lens or the eye acquired for example by OCT (optical coherence tomography) and/or refractive data acquired from Scheimpflug images.

In a further embodiment of input data, the input data comprises lens data of said artificial lens preferably of said intraocular lens and/or treatment plan data relating to a treatment plan for said treating of said artificial lens. For example, the lens data may comprise data relating to one or more of the polarizability and/or refractive index of the artificial lens as a function of the location of a respective volume or part of the artificial lens, shape, diopter, cylinder and sphere and/or its individual aberrations in said dimensions. The polarizability may therefore be increased or decreased at a particular location or volume in one or more planes of the artificial lens depending on the current polarizability (or refractive index) and the polarizability (or refractive index) to be obtained via the treatment.

Additionally or alternatively, the lens data may comprise data relating to one or more of a dimension (for example diameter and/or thickness) of the artificial lens, the lens shape, diopter, cylinder, sphere and/or its individual aberrations in said dimensions, and data relating to a material of which the artificial lens preferably the intraocular lens is comprised. Preferably, the lens data comprise data relating to one or more of a dimension (for example diameter and/or thickness) of the artificial lens or IOL or data to one or more of the polarizability and/or refractive index of the artificial lens as a function of the location of a respective volume or part of the artificial lens, the lens shape, diopter, cylinder, sphere, and/or its individual aberrations in said dimensions, and data relating to a material of which the artificial lens is comprised being part of the individual input data set.

The preferred material of which the artificial lens preferably the intraocular lens is comprised is explained below.

The treatment plan calculation may, in some examples, generate control commands resulting in one or more of treatment plan data comprising: scan strategy control command data of a scan strategy (for example a scanning pattern and/or a scanning sequence and/or a scanning speed and/or a scanning duration of the scanning pattern and/or a scanning duration of the scanning sequence and/or a pulse duration of a pulse of the irradiation beam of the first and/or second wavelength (for example, nanosecond or picosecond or femtosecond pulses) and/or an irradiation beam profile of the irradiation beam of the first and/or second wavelength and/or a radiation (photon) density and/or a radiation intensity and/or a radiation power and/or radiation wavelength) for said scanning of the irradiation beam of the first and/or second wavelength across the artificial lens, in-process input data such as temperature data of a current and/or predicted temperature of the artificial lens during said exposure, refractive index/polarizability data of a refractive index/polarizability of the artificial lens to be obtained based on said exposure, the refractive index/polarizability to be obtained in particular relating to a mapping of the refractive index/polarizability to be obtained to a specific location/coordinates of the artificial lens, rhexis dimension data of a dimension of a rhexis, and individual input data such as eye data relating to a dimension and/or a shape of the eye of the patient, positioning data relating to a position and/or orientation of the artificial lens relative to the eye, and registration data relating to an identification of the patient and/or the specific eye of the patient.

Preferably, the scan strategy control command data of a scan strategy are a scanning pattern and/or a scanning speed and/or a pulse duration of a pulse and/or radiation intensity as described further below.

The parameters of the irradiation beam(s) may then be adjusted according to the lens data and/or the treatment plan data as defined herein in order to precisely (locally) change the polarizability/refractive index of the artificial lens, where desired.

Preferably, the parameters of the irradiation beam(s) are adjusted according to the lens data and/or the treatment plan data as described before or preferably described herein.

The skilled artisan is well aware in this regard that optimum irradiation focus conditions are reached when the depth-of-field (Rayleigh range) of the irradiation beam is matched to the desired thickness of the optical structure to be written into the artificial lens.

The skilled artisan is well aware in this regard that optimum irradiation focus conditions are reached when the depth-of-field (Rayleigh range) of the irradiation beam is matched adapted to the local thickness of the artificial lens.

In a further embodiment, the lens data comprises data relating to a radiation absorption property (for example an absorption and/or light attenuation coefficient, which may be dependent from the wavelength of light) of a said artificial lens, and wherein the system is configured to adjust the first wavelength and/or the second wave-length for said artificial lens to locally change the polarizability based on a multi-photon absorption process. For example, based on the material used for the artificial lens, a particular wavelength or wavelength ranges may be input for a precise local change of the polarizability of the artificial lens.

As part of the system according to the invention as described before and further described below, the input unit is configured to input these input data as described before for treating the artificial lens which may be on a sample holder for the treatment of a contact lens or which may be in a patient's eye for the non-invasive adjustment of an intraocular lens.

Therefore, the invention further relates to a system as described before or below, wherein the input data comprises lens data of said artificial lens and/or treatment plan data relating to a treatment plan for said treating of said artificial lens.

Therefore, the invention further relates to a system as described before or below, wherein the lens data comprises data relating to a radiation absorption property of a said artificial lens, and wherein the system is configured to adjust the first wavelength and/or the second wavelength for said artificial lens to locally change the polarizability based on a multi-photon absorption process.

The one or more irradiation sources as part of the system according to the invention may comprise one or more pulsed lasers which may be utilized to generate nano-second pulses, preferably pico-second pulses and more preferably femto-second pulses. Preferably, one irradiation source is used. Particular preferably, the one or more irradiation sources comprise one or more pulsed lasers which are used to generate femto-second pulses. Particular preferably, one pulsed laser is used to generate femto-second pulses is used as irradiation for the system according to the invention or for the processes and methods according to the invention.

In one embodiment of the invention, the one or more irradiation sources comprise a laser which is tunable to emit a laser beam having the first and second wavelengths, respectively. This may be particularly advantageous as a single laser may be used to (locally) increase or decrease the polarizability/refractive index of the intraocular lens, as desired.

Different pulsed laser types are suitable for said irradiation sources within the system according to the invention. MHz laser as well as kHz laser are suitable and have their particular merits. While a MHz laser system, for example, operates at lower pulse energy, the focused laser spots can be kept at μm-scale (<1 μm to several μm) and thus be used for precise local index modifications in all three dimensions, for example, to generate diffractive structures. A preferred MHz-irradiation source is an 80 MHz laser with a pulse energy ranging from 0.1 to 10 nJ.

A kHz-laser on the other hand operates at higher pulse energy of typically 0.1 to 10 μJ and thus requires a larger spot size of, for example, 10 to 100 μm in order to not damage the lens material. A larger laser spot size, however, implies a large depth of field (=long Rayleigh range) that can be equal to or even exceed the thickness of the artificial lens material. For such long Rayleigh ranges, it might not be possible to modify the refractive index layer by layer in the IOL but only uniformly along a line around the focus. A preferred kHz-irradiation source is a laser with a repetition rate of 100 to 500 kHz.

The average power of the irradiation source as described before or preferably described before is preferably between 300 and 600 mW, particular preferably between 400 and 500 mW.

In a further embodiment of the invention, the same laser source as irradiation source is used by doubling the frequency of the feed laser or an optical power amplifier is used or another laser source is used in order to generate an irradiation beam having a wavelength out of the range given for the first and second wavelengths, respectively.

The irradiation source as part of the system according to the invention preferably comprises a tunable laser that can provide a variable wavelength in the range of approximately 680-1080 nm, such as a Ti:Sapphire laser (for example Chameleon Ultra II by Coherent, Santa Clara, CA, USA). The system may also comprise an optical parametric oscillator (for example frequency doubled Chameleon Compact OPO-Vis by Coherent, Santa Clara, CA, USA).

The irradiation source as part of the system according to the invention particularly preferably comprises a femtosecond pump laser along with an optical parametric amplifier. Said pump laser emits irradiation>10 Watt average power at 1030 nm in <350 fs pulses with a repetition rate of 0.1 to 700 kHz. The radiation of said pump laser is directed to an optical parametric amplifier, where the pump laser output is frequency-doubled and optically mixed, resulting in a final tunable output in a wavelength range of 600 nm to 800 nm. A preferred repetition rate is between 50 and 600 kHz. A particular preferred repetition rate is between 100 and 500 kHz.

The irradiation source as part of the system according to the invention particularly preferably comprises a femtosecond pump laser>10 Watt average power at 1030 nm in combination with an optical parametric amplifier, which is emitting irradiation pulses<350 fs at a repetition rate of 1 to 700 kHz. The radiation of said pump laser is directed to an optical parametric amplifier with one or multiple second-harmonic stages, resulting in a final optical output in a wavelength range of 400 nm to 590 nm. A preferred repetition rate is between 50 and 600 kHz. A particular preferred repetition rate is between 100 and 500 kHz.

The laser types as described before or preferably described before generate a collimated optical beam of a few millimeter in diameter, which is then directed to optics and scanner. The optical beam quality (measured in units of $M^2$) is ideally between 1.0 and 1.5, more ideally between 1.0 and 1.3.

Multi-photon excitation occurs only in the vicinity of the focal point and preferably by employing ultra-short laser pulses as described before. The average power is limited by the sample damage threshold such threshold being part of the common input data as defined before.

The ideal parameters for two-photon induced cyclodimerization reactions are linked to the relation of pulse duration and repetition rate from the system to the characteristic time constants of the artificial lens material able to cyclodimerize as further described or preferably described below, which in a nutshell comprise the molecular S1-state life time (~few ns), the lifetime of long lived triplet states (many ns to >μs) and the characteristic thermal diffusion time (~1 μs).

Considering the lifetime of long-lived triplet states, longer separation of pulses is an advantage. The lifetime of triplet states in the photochemically active groups (many ns to >μs) is much longer than the repetition rate in an 80 MHz system (12.5 ns). Using a kHz laser as described before or preferably described before is therefore advantageous since most triplet states are cleared before the next pulse is launched. This effect results in a significant increase in efficiency of the cyclodimerization reaction of the artificial lens material as further preferably described below. The temperature increase within the focus by linear absorption referred to by characteristic thermal diffusion time will relax within a microsecond, about 80-times slower than the separation of typical ~80 MHz pulses. Hence, the temperature increase is high. This is not the case for kHz-pulses. Here, the thermal diffusion time is 10 times faster than the separation of typical 100 kHz pulses. Therefore, irradiating at a constant laser fluence, the local temperature rise due to laser heating is more prominent at higher repetition rates.

The first wavelength of the irradiation beam within the system according to the invention is between 600 nm and 800 nm, preferably between 650 nm and 750 nm, more preferably between 670 nm and 720 nm, more preferably between 680 and 710, in order to (locally) decrease the polarizability (and hence the refractive index) of the IOL.

The second wavelength of the irradiation beam within the system according to the invention is between 400 nm and 590 nm, preferably between 500 nm and 580 nm, more preferably between 530 nm and 570 nm, in order to (locally) increase the polarizability (and hence the refractive index) of the IOL.

The polarizability may hereby be locally changed particularly precisely.

Based on (locally) changing the polarizability of the artificial lens, the refractive index of said lens may be changed (locally). Further details to this correlation are described below.

Typical laser parameters are 680 nm wavelength, 180 fs pulse duration and an average power of 500 mW as described in one of the below mentioned examples.

Optics within the system according to the invention:

The main function of the optics is to focus the irradiation beam, which is emitted from the irradiation source and controlled by the scanner, onto the artificial lens. Key considerations as described before are spot size and depth of focus in order to minimize treatment time while staying within limits given by laser safety requirements and material damage as described before as part of common input data. The most important characteristics of the optic is given by its numerical aperture (NA), along with its effective focal length (EFL) and the diameter of the irradiation beam at the entry aperture of the focusing optics. Additionally, all optical elements within the system according to the invention should be selected for diffraction- or near-diffraction-limited properties, in order to not substantially degrade the optical beam quality.

Different ophthalmic needs will require different spot sizes as the spot size determines the obtainable spatial resolution. Ideally, the spot size is between 1 and 100 μm, more ideally between 50 and 100 μm in order to minimize treatment time while also keeping the potential for material damage low.

Scanner within the system according to the invention:

The scanner to be used within the system according to the invention may comprise a Galvano-scanner, a piezo scanner, a rotational scanner or an acousto optic modulator or it may be digital such as a spatial light modulator, a digital micromirror device or stereolithography apparatus. Preferably, the scanner as part of the inventive system according to the description is selected from a Galvano-scanner, a piezo scanner, a rotational scanner, an acousto optic modulator, a spatial light modulator, a digital micromirror device or stereolithography apparatus. A preferred Galvano-scanner is a single Pivot-Point-Scanner.

Preferably, the scanner is configured to operate at a scanning speed of more than 50 mm/s. This may allow for keeping the treatment time short. As a general rule, the treatment time should not exceed several minutes and is preferably less than 10 minutes, preferably less than 5 minutes, particularly preferably less than 3 minutes per treatment session.

The treatment area may be defined as the artificial lens' volume and size. Typically, the optic of said lens is 5 mm to 7 mm in diameter and typically between 0.2 mm and 2.0 mm thick.

The optimum radiation exposure is <1 $kJ/cm^2$ and more ideally <0.3 $kJ/cm^2$ to keep the overall irradiation exposure low and treatment time short, while addressing the full volume of the artificial lens.

Particularly preferably, random scan patterns or interleaved scanning lines are used to spread out the irradiation energy of the irradiation beam.

The scanning can be performed with three modes. In the bottom-up scanning, the laser may travel from spot-to-spot with a specific dwell time on each spot ("bottom-up, spot-to-spot"). Alternatively, in the bottom-up scanning, the laser may dwell on spots that overlap with one another ("bottom-up, spot overlay"). Alternatively, the laser can travel with a fixed velocity without dwelling on any spots ("fly by, constant velocity"). FIG. 3 shows a schematic illustration (1500) of such scanning strategies as described before.

In one embodiment of a scan pattern, the IOL is scanned with the irradiation source as described before or preferably described before by shining through the pupil. The IOL, contained in the capsular bag at the time of scanning, is previously inserted through an incision in the cornea using conventional operation procedures. In this embodiment, the full volume of the IOL is scanned and the scanning is performed in a bottom-up manner (i.e. parts of the IOL which are further away from the cornea are scanned first), this way the optical profile is created in order to avoid unnecessary changes in refractive index in the light path.

As described before a key consideration when selecting the scanning program is to minimize local heating of the artificial lens and/or the eye of the patient and therefore various variables are used in the scanning program. Taking into account anatomical features such as Rhexis and pupil size as well as optical features such as numerical aperture and laser pulse characteristics, a laser program is created with a specific scanning speed and sequence. The relation between lens coordinate and eye coordinate system are, in this example, automatically taken into account. FIG. 4 shows a schematic illustration (1600) of said variables used in the scanning program as described before taken into account when irradiating the lens within the eye of a patient.

The parameters for the scanning program and/or treatment plan are preferably the first and second wavelengths, the scanning speed and sequence, the positioning (e.g. in Cartesian coordinates) of the lens relative to the eye, the scan strategy, the refractive index change which is to be obtained (optical pattern), the numerical aperture of the objective, the Rhexis, the optical diameter (in some examples approximately 6 mm) of the pupil and/or the lens, the pulse duration (shape, intensity and x-y positioning) of the laser beam, laser safety when operating the laser, and centration with respect to the positioning of the lens and the eye.

The photons generated in the laser are in one embodiment of the system according to the invention preferably guided through mirrors (e.g. as optic 1) to a e.g. a beam expander, which prepares the beam for the subsequent scanner and focusing optic. After passing through the beam expander, the photons are directed toward the scanner (e.g. Galvano-scanner or piezo scanner or rotational scanner or acousto optic modulator or digitally with a spatial light modulator or digital micromirror device or stereolithography apparatus).

After having gone through the scanner, the laser beam travels through another optic such as a divider mirror. In this embodiment, the divider mirror splits up the beam into the main imaging beam for the artificial lens irradiation and a beam for monitoring beam properties as well as for positioning feedback. After the divider mirror, the optical beam is focused onto the artificial lens by imaging group or focusing optic. In one embodiment, the imaging group comprise a microscope objective to obtain high numerical apertures (for μm-level spatial resolution) or low-NA optics to allow higher pulse energy of μJ-level.

The system as described before or preferably described before further comprises in one further embodiment of the system a microscope objective coupled to the scanner for focusing, by the microscope objective, a said irradiation beam onto said artificial lens, wherein the microscope objective has a numerical aperture of between 0.1 and 0.8, preferably between 0.2 and 0.5, and more preferably between 0.2 and 0.4. Providing a microscope objective having such numerical aperture may allow for high irradiation beam quality in particular in terms of focusing and resolution characteristics of the beam used for treating the intraocular lens.

The microscope objective comprises of a typical lens configuration to allow for e.g. correction of chromatic aberration. The microscope objective is preferably linked to an eye interface system, typically a suction system that keeps the eye of the patient in a fixed position as further described below.

In a further embodiment of an objective to be used within the system according to the invention as described before, the objective is an Olympus LUCPLFLN objective in order to focus the irradiation beam onto the artificial lens.

Therefore, the invention further relates to a system as described before further comprising a microscope objective coupled to the scanner for focusing, by the microscope objective, a said irradiation beam onto said artificial lens, wherein the microscope objective has a numerical aperture of between 0.1 and 0.8, preferably between 0.2 and 0.5, and more preferably between 0.2 and 0.4.

An alternative focusing optic/imaging group is configured with a single aspherical lens with an effective focal length preferably within 50 to 150 mm and a numerical aperture of preferably 0.025 to 0.1.

Therefore, the invention further relates to a system as described before, further comprising a focusing optic/imaging group configured with a single aspherical lens with an effective focal length preferably within 50 to 150 mm and a numerical aperture of preferably 0.025 to 0.1.

The system as described before or preferably described before further comprises in one further embodiment a positioning system for determining a position of a said focus of said irradiation beam within a said eye of a said patient, wherein the positioning system is coupled to the scanner and wherein the scanning, by the scanner, of said irradiation beam across said intraocular lens is based on the position of said focus of said irradiation beam within the eye. The positioning system may comprise a locating system such as an optical coherence tomography system, a confocal microscope or a Scheimpflug camera. The positioning system may be directly or indirectly coupled to the scanner. In some examples in which a confocal microscope is used, the confocal microscope may be directly coupled to the scanner.

The locating system as described before is used to provide topographic data of the eye to the positioning system for determination of the position of the laser focus in dependence of the eye and said intraocular lens. For confocal microscopy, a partially transparent mirror is used to allow for video imaging.

The system as described before or preferably described before is preferably configured further to determine a location and/or orientation of said intraocular lens relative to the eye and the outlet of the irradiation beam, and wherein the scanning, by the scanner, of said irradiation beam across said intraocular lens is based on the location and/or orientation of said intraocular lens relative to the eye. This may be particularly advantageous since the position of the intraocular lens may not be centered relative to the eye, which misalignment may be taken into account when treating the intraocular lens with the irradiation beam(s).

With respect to the position of the IOL, at least 2 coordinate systems may be considered relevant: coordinates-system of the eye and coordinates-system of the lens within the eye, as both may not be centered with respect to each other.

With respect to the position of the IOL, at least 2 coordinate systems may be considered relevant: x,y,z coordinates of the eye and x,y,z coordinates of the lens within the eye, as both may not be centered with respect to each other.

In one embodiment, the locating system creates individual input data. These individual input data contain for example data concerning lens position and/or orientation of the artificial lens within the eye and relative to the laser beam outlet, and/or an optical power mapping of the eye and/or the artificial lens. These data are used for the calculation of the optical pattern or a continuation of a treatment.

Additionally, it is possible that the locating system creates input data during the writing process. These in-process input data contain for example data concerning lens position and/or orientation of the artificial lens within the eye and relative to the laser beam outlet, and/or an optical power mapping of the eye and/or the artificial lens. These data are used for in-process modification of the control commands used to generate the optical pattern.

Therefore, the invention further relates to a system as described before, further comprising a positioning system for determining a position of a focus of said irradiation beam within a said eye of a said patient,
- wherein the positioning system is coupled to the scanner and wherein the scanning, by the scanner, of said irradiation beam across said artificial lens is based on the position of said focus of said irradiation beam within the eye.

Therefore, the invention further relates to a system as described before, wherein the system is configured to determine a location and/or orientation of said artificial lens relative to the eye and the outlet of the irradiation beam, and
- wherein the scanning, by the scanner, of said irradiation beam across said artificial lens is based on the location and/or orientation of said artificial lens relative to the eye.

The system as described before or preferably described before further comprises in one further embodiment a temperature management unit coupled to one or both of (i) the one or more irradiation sources and (ii) the scanner, wherein the temperature management unit is configured to determine, based on an irradiation beam property of a said irradiation beam and an artificial lens property of a said artificial lens, a temperature of a part of said artificial lens during said treating of said artificial lens by said scanning, and wherein the system is configured to control, based on said determination of the temperature, one or both of (i) the one or more irradiation sources and (ii) the scanner. This may allow for ensuring that the eye and/or the artificial lens may not be detrimentally affected based on the treatment with an irradiation beam.

Additionally, the temperature management unit is preferably configured to predict said temperature during said treating of said artificial lens, and wherein said input data comprises the predicted temperature. This may allow for taking preventative measures to ensure that the eye and/or the artificial lens may not be detrimentally affected based on the treatment with an irradiation beam.

Alternatively, the temperature management unit is an infrared camera logging the temperature of the eye and correlating the measured data with common data bearing calibration data to calculate the real temperature in the eye.

In another embodiment, the temperature dependence of refractive index is used for temperature controlling. In these examples, the system comprises a refractive power mapping device. Based on the deviation of the measured refractive power map and the progress of the writing predicted refractive power map, temperatures in the lens can be calculated in process.

In another embodiment, the temperature dependence of the emission spectrum is used for temperature controlling. In these examples, the system comprises a UV-Vis spectrometer. Based on the deviation of the measured emission peak wavelength and/or peak width, temperatures in the focal spot can be calculated in process.

Therefore, the invention further relates to a system as described before comprising a temperature management unit coupled to one or both of (i) the one or more irradiation sources and (ii) the scanner,
- wherein the temperature management unit is configured to determine, based on an irradiation beam property of a said irradiation beam and an artificial lens property of a said artificial lens, a temperature of a part of said artificial lens during said treating of said artificial lens by said scanning, and wherein the system is configured to control, based on said determination of the temperature, one or both of (i) the one or more irradiation sources and (ii) the scanner.

Therefore, the invention further relates to a system as described before, wherein the temperature management unit is configured to predict said temperature during said treating of said artificial lens, and wherein said input data comprises the predicted temperature.

The system as described before or preferably described before further comprises in one further embodiment an eye interface system configured to keep a said eye of a said patient in a fixed position. The eye interface system may comprise a suction system for fixing the position of the eye of the patient during treatment.

The patient may be "docked" to the system in a lie flat or upright position.

Therefore, the invention further relates to a system as described before comprising an eye interface system configured to keep a said eye of a said patient in a fixed position.

The system as described before or preferably described before further comprises in one further embodiment a wireless or wired receiver and/or transceiver for one or more of (i) sending control commands to the one or more irradiation sources, (ii) sending control commands to the scanner, and (iii) inputting the control command data needed for creating the optical pattern into the scanner.

The one or more irradiation sources and/or the scanner may therefore be controlled remotely. Additionally or alternatively, the data relating to one or both of the lens data and the treatment plan data may be stored externally from the system and may be provided to the system as and when desired. In some examples, it may be preferable to provide a wired receiver or transceiver at least for controlling the one or more irradiation sources and/or for controlling the scanner in order to reduce (or avoid) any delay when sending a control signal to the one or more irradiation sources and/or the scanner In another example, the receiver/transceiver sends treatment plan data and lens data to a central computing unit which calculates the optical pattern and sends this as input data back to the receiver which provides it to the system.

The system as described before or preferably described before further comprises in one further embodiment a device for locally measuring the refractive power of said artificial lens during said treating of the artificial lens. Adjustments to one or more of the irradiation source(s), the scanner and the input data may hereby be made during the treatment process.

The system as described before or preferably described before further comprises in one further embodiment a refractometer for locally measuring the refractive index of said artificial lens during said treating of the artificial lens. Adjustments to one or more of the irradiation source(s), the scanner and the input data may hereby be made during the treatment process.

Further components of the system providing the photons are optionally a cover in which all the equipment is built in, a power unit to provide the system and all sub-systems with sufficient energy, and sub-systems like a suction system and/or chiller.

In addition to the above mentioned components, controller, firmware and a graphics user interface (GUI) as well as treatment algorithms may be provided. To connect to the system, connectivity may be established via Bluetooth, Wi-Fi or other ports like RS-232.

FIG. 5 shows a further schematic illustration of a system (100) for the irradiation of an intraocular lens arranged within an eye of a patient (136). The system (100) generally relates to a laser system comprising at least one femtosecond laser source (102, 104) able to generate at least one, preferably two different wavelengths. The system (100) further comprises a focus- or Z-shifter optic (106), a scanner (110) (Galvano-scanner, a piezo scanner, a rotational scanner, an acousto optic modulator, a spatial light modulator, a digital micromirror device or stereolithography apparatus), and an optic (108) delivering the laser pulses into the predetermined region. The system (100) may be able to achieve the same level of energy delivered to the targeted regions of the polymeric material comprising photochemically active units forming the intraocular lens arranged within the eye of the patient (136). The system further comprises in FIG. 5 an eye interface (112) for fixing the eye of the patient (136). In FIG. 5, the laser system is connected to a computer controller (116), incorporating corresponding device firmware (118) and a frontend graphical user interface (GUI) (120). Algorithms (122) are used to calculate the level of energy delivered to the targeted regions of the polymeric material comprising photochemically active units forming the intraocular lens in a treatment planning system. System parameters and process treatment plan (134) are monitored via the GUI (120). Input and adjustments from the patient (136), e.g. lens data (130) and refractive index shaping plan (132) may be input via GUI (120). The laser source, subsystems and body fixation (124) may be integrated into a single module connected to electric power (126) sealed with a cover (128).

FIGS. 6 and 7 show schematic illustrations of components of a system according to the invention as described herein.

The photons generated in the irradiation source (202) are guided, in the example of FIG. 6, through mirrors (optic system 1, e.g. beam shaper (204), focus shifter/Z-shifter (206) to a scanner (208) (e.g. Galvano-scanner or piezo scanner or rotational scanner or acousto optic modulator or digitally with a spatial light modulator SLM). Attached to the scanner (208) is a microscope objective (optic system 2) and patient interface (210).

As shown in FIG. 7, a Z-shifter (302) comprises a first lens (304), a second lens (306) and a third lens (308). The irradiation beam then travels to the scanner (310), which comprises a plurality of mirrors (312), (314) and (316), which allow for changing the position in the x-y direction of the irradiation beam on the IOL. After having gone through the scanner (310), the irradiation beam travels through a divider mirror (318) for imaging, before going through the imaging group (320). The system further comprises an illumination unit (322) and a patient interface (324).

The application further describes a process for adjusting a polarizability of an artificial lens (preferably at one or more particular locations of said lens) comprising a body formed of a polymeric optical material based on a two- or multiphoton absorption process, the process comprising the steps of: providing said lens; and adjusting the polarizability of said lens by using a system as described or preferably described throughout the present disclosure thereupon changing the polymeric optical material with significant differences in the UV/Vis spectrum with respect to the non-irradiated polymeric optical material of the artificial lens. Said artificial lens is preferably a contact lens or an IOL comprising a polymerized optical material as described or preferably described below. Said process for adjusting the polarizability according to the invention as described before or preferably described below is performed in a non-destructive manner of the artificial lens material.

Ultraviolet-visible spectroscopy or ultraviolet-visible spectrophotometry (UV-Vis or UV/Vis) is known to a person skilled in the art. It refers to absorption spectroscopy or reflectance spectroscopy in part of the ultraviolet and the full, adjacent visible spectral regions. Suitable UV/Vis spectrometers are commercially available. The choice of the UV/Vis spectrometer is not critical for the comparison of the UV/Vis spectrum of the initial artificial lens and the UV/Vis spectrum of said irradiated artificial lens to be made according to the present invention. As long as both measurements are made under comparable conditions so that the results can be compared which is known to the person skilled in the art. A suitable spectrometer is the UV/Vis spectrometer Lambda 900 from Perkin Elmer.

The artificial lens may then, in some examples, subsequently be introduced into the eye of a patient. In some examples, the lens may comprise an intraocular lens, such that polarizability of the lens may be adjusted while the lens is arranged within the eye of the patient.

Within the process as described before, said adjusting of the polarizability of the artificial lens comprises decreasing the polarizability by irradiating the artificial lens with an irradiation beam having a wavelength of between 600 nm and 800 nm thereupon changing the polymeric optical material with significant differences of the UV/Vis spectrum namely loss in peak absorption in the range of 300 nm to 400 nm with respect to the non-irradiated polymeric optical material of the artificial lens.

Therefore, the invention further relates to a process as described before wherein said adjusting of the polarizability of the artificial lens comprises decreasing the polarizability by irradiating the artificial lens with an irradiation beam having a wavelength of between 600 nm and 800 nm thereupon changing the polymeric optical material with significant differences of the UV/Vis spectrum namely loss in peak absorption in the range of 300 nm to 400 nm with respect to the non-irradiated polymeric optical material of the artificial lens.

Within the process as described before, said adjusting of the polarizability of the artificial lens comprises increasing the polarizability by irradiating the artificial lens with an irradiation beam having a wavelength of between 400 nm and 590 nm thereupon changing the polymeric optical material with significant differences of the UV/Vis spectrum namely increase in peak absorption in the range of 300 nm to 400 nm with respect to the non-irradiated polymeric optical material of the artificial lens.

Therefore, the invention further relates to a process as described before wherein said adjusting of the polarizability of the artificial lens comprises increasing the polarizability by irradiating the artificial lens with an irradiation beam having a wavelength of between 400 nm and 590 nm thereupon changing the polymeric optical material with significant differences of the UV/Vis spectrum namely increase in peak absorption in the range of 300 nm to 400 nm with respect to the non-irradiated polymeric optical material of the artificial lens.

Therefore, the invention further relates to a process for adjusting a polarizability of an artificial lens (preferably at one or more particular locations of said lens) comprising a body formed of a polymeric optical material based on a two- or multi-photon absorption process, the process comprising the steps of:

providing said lens; and adjusting the polarizability of said lens by using a system comprising:

one or more irradiation sources for two-photon or multi-photon irradiating a said artificial lens with an irradiation beam focused with an optic and of a first wavelength and/or a second wavelength different from the first wavelength, a scanner coupled to the one or more irradiation sources and configured to scan a said irradiation beam across said artificial lens, and an input unit coupled to the one or more irradiation sources and the scanner, wherein the input unit is configured to input data for treating said artificial lens by scanning a said irradiation beam across said artificial lens based on the input data, and wherein the first wavelength is between 600 nm and 800 nm for locally decreasing, based on said treating of said artificial lens, a polarizability of said artificial lens thereupon changing the polymeric optical material with significant differences of the UV/Vis spectrum namely loss in peak absorption in the range of 300 nm to 400 nm with respect to the non-irradiated polymeric optical material of the artificial lens, and wherein the second wavelength is between 400 nm and 590 nm for locally increasing, based on said treating of said artificial lens, the polarizability of said artificial lens thereupon changing the polymeric optical material with significant differences of the UV/Vis spectrum namely increase in peak absorption in the range of 300 nm to 400 nm with respect to the non-irradiated polymeric optical material of the artificial lens.

The particular wavelength used for decreasing and/or increasing the polarizability of the artificial lens may depend on which particular material or composition may be used for the artificial lens. Any one or more of the polymeric optical materials described throughout the present disclosure may be used in order to prepare and/or provide the lens.

Special polymers as described below are preferably utilized which are suitable for the fabrication of artificial lenses, preferably IOLs whose optical properties may be changed (non-invasively) later on utilizing their ability to change the polarizability and hence the refractive index if a two-photon or multi-photon process is applied.

Said special polymers as described below are preferably utilized to be treated with the system according to the invention and/or are preferably used in the process according to the invention.

The two-photon or multi-photon process is created by utilizing the system as described in detail before.

The area of applicable wavelengths of the irradiation source, preferably the pulsed laser ranges as described before from 600 nm to 800 nm, preferably from 650 nm to 750 nm, particular preferably from 670 nm to 720 nm and very particular preferably from 680 to 710 nm, to decrease the polarizability and hence to decrease the refractive index of said artificial lens.

The area of applicable wavelengths of the irradiation source, preferably the pulsed laser ranges as described before from 400 nm to 590 nm, preferably from 500 nm to 580 nm, and particular preferably from 530 nm to 570 nm to increase the polarizability and hence to increase the refractive index of said artificial lens.

The polarizability may hereby be locally changed particularly precisely.

In the following, the optical material of the artificial lens to be used in the process according to the invention, preferably the polymeric optical material of the contact lens or IOL, is further and preferably described for the area of wavelengths from 600 nm to 800 nm, preferably from 650 nm to 750 nm, particular preferably from 670 nm to 720 nm and very particular preferably from 680 to 710 nm for locally decreasing the polarizability of said material.

To apply this adjustment, the polymeric optical material has a refractive index ranging from 1.45 to 1.60.

The polymeric optical material of the artificial lens (contact lens or IOL) can optionally contain an ultraviolet light blocker or a blue light absorber.

Said polymeric optical material of the artificial lens as used in the process according to the invention for said adjustment comprises a polymeric matrix comprising covalently bound photoactive units, preferably in an amount of at least 2 wt % to 100 wt %, preferably 5 wt % to 90 wt %, most preferably 7 wt % to 80 wt %.

The photoactive units within said polymeric matrix can be the same or different.

The polymeric matrix of the polymeric optical material of the artificial lens and/or IOL for said adjustment can be a matrix from homopolymers or copolymers, preferably from copolymers.

The polymeric matrix comprising a photoactive unit can be a matrix from silicon-containing polymers, acrylic polymers, methacrylic polymers or mixtures thereof.

A photoactive unit means a photochemically active unit which is photochemically active in the area of applicable wavelengths as described or preferably described before under the effect of a two-photon or multi-photon process.

The photoactive units preferably comprise a non-aromatic double bond, preferably a carbon-carbon double bond which is able to dimerize by forming a cyclobutane ring by means of a [2π+2π] cycloaddition under the effect of the two-photon or multi-photon process.

Therefore, the invention further relates to a process for adjusting a polarizability of an artificial lens (preferably at one or more particular locations of said lens) comprising a body formed of a polymeric optical material, wherein said optical material of the artificial lens comprises a polymeric matrix comprising covalently bound photoactive units comprising a non-aromatic double bond, preferably a carbon-carbon double bond which is able to dimerize by forming a cyclobutane ring by means of a [2π+2π] cycloaddition under the effect of the two-photon or multi-photon process. In this embodiment, the photoactive units within the polymeric optical material of the artificial lens to be used in the process according to the invention can be the same or different but are the sole photoactive units in said polymeric optical material and are all classified in that they comprise a non-aromatic double bond, preferably a carbon-carbon double bond which is able to dimerize by forming a cyclobutane ring by means of a [2π+2π] cycloaddition under the effect of the two-photon or multi-photon process as described before or further preferably described below.

Alternatively, the polymeric matrix comprises said photoactive units as described before or below together with already dimerized photoactive units. Therefore, the polymeric matrix may still comprise photoactive units, which are able to dimerize. The polymeric optical material (polymeric matrix) may be partially dimerized.

In said embodiment of the optical material of the artificial lens to be used in the process according to the invention, preferably the polymeric optical material of the contact lens or IOL, such material can be irradiated with either the first or the second area of wavelengths as described before to decrease or increase the polarizability and hence to decrease or increase the refractive index of said artificial lens comprising said polymeric optical material. With such polymeric optical material the polarizability of the artificial lens is thus tunable.

Therefore, the invention further relates to a process for adjusting a polarizability of an artificial lens (preferably at one or more particular locations of said lens) comprising a body formed of a polymeric optical material, wherein said optical material of the artificial lens comprises a polymeric matrix comprising covalently bound photoactive units comprising a non-aromatic double bond, preferably a carbon-carbon double bond which is able to dimerize by forming a cyclobutane ring by means of a [2π+2π] cycloaddition under the effect of the two-photon or multi-photon process together with already dimerized photoactive units. In this embodiment, the photoactive units within the polymeric optical material of the artificial lens to be used in the process according to the invention can be the same or different but are the sole photoactive units in said polymeric optical material and are all classified in that they comprise a non-aromatic double bond, preferably a carbon-carbon double bond which is able to dimerize by forming a cyclobutane ring by means of a [2π+2π] cycloaddition under the effect of the two-photon or multi-photon process as described before or further preferably described below or said photoactive units are their dimerized photoactive units.

The photoactive units within the polymeric optical material of the artificial lens to be used in the process according to the invention particularly preferably comprise a non-aromatic carbon-carbon double bond in conjugation with at least one aromatic ring system which is able to dimerize by forming a cyclobutane ring by means of a [2π+2π] cycloaddition under the effect of the two-photon or generally multi-photon process.

Preferably the non-aromatic double bond and the aromatic ring system in conjugation with the non-aromatic double bond form a fused ring system as part of the photoactive unit as explained before, preferably a bicyclic or tricyclic ring system, particularly preferably a bicyclic ring system.

Examples of such fused ring systems in conjugation with a non-aromatic carbon double bond as explained before as part of the photoactive units within the polymeric optical material of the artificial lens to be used in the process according to the invention are chromene-2-ones, chromene-2-thiones, thiocheomene-2-ones, thiochromene-2-thiones, quinolin-2-ones, quinolin-2-thiones, benzo[b]furans, benzo[b]thiophenes, benzo[b]pyrroles, indenes, 1,2-dihydronaphthalenes, 6,7-dihydro-5H-benzo[7]annulene, (Z)-5,6,7,8-tetrahydrobenzo[8]annulene.

The [2π+2π] cycloaddition can be visualized according to the following scheme 1. FIG. 8 shows a specific [2π+2π] cycloaddition reaction of poly(M-14); said representative material will be further described in examples 1 and 2. Scheme 1 further visualizes the cycloreversion. FIG. 9 shows a specific cleavage of poly(M-14)-dimer by cycloreversion which is further described in examples 3 and 5.

Scheme 1:

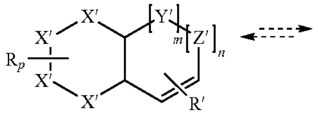

-continued

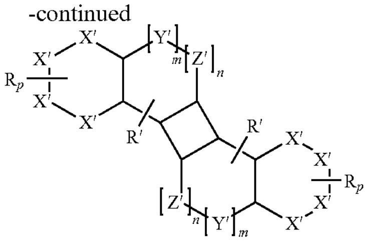

$R_p$ means the polymer/copolymer backbone covalently linked to the fused ring system via a linker;

X'-X' is independently of each other CH═CH, CR'═CH, CH═CR' or CR'═CR';

Y' is O, S, NR', $CH_2$, CHR', $C(R')_2$;

m is 1 in case Y' is O, S or NR' and m is 1, 2, 3 or 4 in case Y' is independently selected at each occurrence from $CH_2$, CHR' and $C(R')_2$;

Z' is C═O or C═S;

n is 0 or 1

R' is an organic substituent.

Examples of silicon-containing polymers that can be used as optical materials of the artificial lens to be used in the process according to the invention are described in WO2018149857.

Examples of acrylate-containing or methacrylate-containing polymers that can be used as optical materials of the artificial lens to be used in the process according to the invention are described in WO2017032442, WO2017032443, WO2017032444, WO2018149850, WO2018149852, WO2018149853, WO2018149855, WO2018149856.

All citations are incorporated by reference.

In one preferred embodiment of the invention, the polymeric optical material comprising the polymeric matrix comprising covalently bound photoactive units of the artificial lens to be used in the process according to the invention contains a polymerized monomer according to formula (1)

(1)

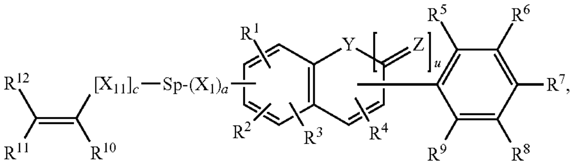

where the symbols used are as follows:

u is 0 or 1,

Y is the same or different at each instance and is O, S, $NR^0$ or $X^1$, $X^1$ is $CH_2$, $CHR^0$, $C(R^0)_2$, $[CH_2]_2$, $[CHR^0]_2$, $[C(R^0)_2]_2$, $[CH_2]_3$, $[CHR^0]_3$, $[C(R^0)_2]_3$, $[CH_2]_4$, $[CHR^0]_4$ or $[C(R^0)_2]_4$;

Z is the same or different at each instance and is O or S;

$X_1$ is O, S or $SO_2$;

a is 0 or 1;

Sp is an alkanediyl, alkenediyl or alkinediyl, which may be substituted by one or more R radicals;

$R^0$ is a straight-chain or branched alkyl group having 1 to 10 C atoms;

$R^1$, $R^2$, $R^3$ and $R^4$ are independently of each other selected from H, F, Cl, Br, I, a straight-chain or branched alkyl group having 1 to 20 C atoms, a partially or fully halogenated straight-chain or branched alkyl group having 1 to 20 C atoms, and an aryl or heteroaryl group with 5 to 40 ring atoms;

$R^5$, $R^6$, $R^7$, $R^8$ and $R^9$ are at each occurrence independently selected from the group consisting of F, a linear or branched, non-halogenated, partially or completely halogenated alkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms and a linear or branched, non-halogenated, partially or completely halogenated thioalkyl group having 1 to 20 C atoms;

$X_{11}$ is selected from the group consisting of O, S, O—$SO_2$, $SO_2$—O, C(═O), OC(═O), C(═O)O, S(C═O) and (C═O)S;

c is 0 or 1;

$R^{10}$, $R^{11}$, $R^{12}$ are independently of each other selected from H, F, a straight-chain or branched alkyl group having 1 to 20 C atoms which may be partially or fully halogenated, and an aryl group having 6 to 14 C atoms;

R is the same or different at each instance and is selected from F, OH, a straight-chain or branched alkyl group having 1 to 10 C atoms, a partially or fully halogenated straight-chain or branched alkyl group having 1 to 10 C atoms, a straight-chain or branched alkoxy group having 1 to 10 C atoms, and a partially or fully halogenated straight-chain or branched alkoxy group having 1 to 10 C atoms.

In one preferred embodiment of the invention, the polymeric optical material comprising the polymeric matrix comprising covalently bound photoactive units of the artificial lens to be used in the process according to the invention contains a polymerized monomer according to formula (2)

(2)

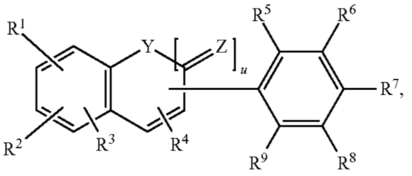

where the symbols used are as follows:

u is 0 or 1,

Y is the same or different at each instance and is O, S, $NR^0$ or $X^1$, $X^1$ is $CH_2$, $CHR^0$, $C(R^0)_2$, $[CH_2]_2$, $[CHR^0]_2$, $[C(R^0)_2]_2$, $[CH_2]_3$, $[CHR^0]_3$, $[C(R^0)_2]_3$, $[CH_2]_4$, $[CHR^0]_4$ or $[C(R^0)_2]_4$;

Z is the same or different at each instance and is O or S;

$X_1$ is O, S or $SO_2$;

a is 0 or 1;

Sp is an alkanediyl, alkenediyl or alkinediyl, which may be substituted by one or more R radicals;

$R^0$ is a straight-chain or branched alkyl group having 1 to 10 C atoms;

$R^1$, $R^2$, $R^3$ and $R^4$ are independently of each other selected from H, F, Cl, Br, I, a straight-chain or branched alkyl group having 1 to 20 C atoms, a partially or fully halogenated straight-chain or branched alkyl group having 1 to 20 C atoms, and an aryl or heteroaryl group with 5 to 40 ring atoms;

$R^5$, $R^6$, $R^7$, $R^8$ and $R^9$ are at each occurrence independently selected from the group consisting of F, a linear or branched, non-halogenated, partially or completely halogenated alkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms and a linear or branched, non-halogenated, partially or completely halogenated thioalkyl group having 1 to 20 C atoms but provided that one of $R^5$, $R^6$, $R^7$, $R^8$ or $R^9$ corresponds to formula (2-1) where * indicates the linkage to the rest of formula (2), (2-1)

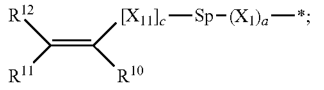

$R^{10}$, $R^{11}$, $R^{12}$ are independently of each other selected from H, F, a straight-chain or branched alkyl group having 1 to 20 C atoms which may be partially or fully halogenated, and an aryl group having 6 to 14 C atoms;

$X_{11}$ is selected from the group consisting of O, S, O—$SO_2$, $SO_2$—O, C(═O), OC(═O), C(═O)O, S(C═O) and (C═O)S;

c is 0 or 1;

R is the same or different at each instance and is selected from F, OH, a straight-chain or branched alkyl group having 1 to 10 C atoms, a partially or fully halogenated straight-chain or branched alkyl group having 1 to 10 C atoms, a straight-chain or branched alkoxy group having 1 to 10 C atoms, and a partially or fully halogenated straight-chain or branched alkoxy group having 1 to 10 C atoms.

Halogenated means preferably fluorinated, chlorinated or brominated, particularly preferably fluorinated.

A straight-chain or branched alkyl group having 1 to 10 C atoms denotes an alkyl group having 1, 2, 3, 4, 5, 6, 7, 8, 9 or 10 C atoms, for example methyl, ethyl, iso-propyl, n-propyl, iso-butyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl or n-decyl. A linear or branched alkyl group having 1 to 20 C atoms include all examples for a linear or branched alkyl group having 1 to 10 C atoms including any alkyl group having 11, 12, 13, 14, 15, 16, 17, 18, 19 and 20 C atoms such as n-undecyl, n-dodecyl, n-tridecyl, n-tetradecyl, n-pentadecyl, n-hexadecyl, n-heptadecyl, n-octadecyl, n-nonadecyl and n-eicosyl.

The term partially halogenated alkyl group denotes that at least one H atom of the alkyl group is replaced by F, Cl, Br or I. Preferably, the alkyl group is partially fluorinated meaning that at least one H atom of the alkyl group is replaced by F.

The term completely halogenated alkyl group denotes that all H atoms of the alkyl group are replaced by F, Cl, Br and/or I. Preferably, the alkyl group is completely fluorinated meaning that all H atoms of the alkyl group are replaced by F. A preferred completely fluorinated alkyl group is trifluoromethyl.

The term halogenated or preferably fluorinated corresponds additionally to other groups such as a halogenated cycloalkyl group, a halogenated alkoxy group or a halogenated thioalkyl group.

A cycloalkyl group having 3 to 6 C atoms includes cyclopropyl, cyclobutyl, cyclopentyl and cyclohexyl which may be partially or completely halogenated or fluorinated as explained before.

A linear or branched alkoxy group having 1 to 20 C atoms denotes an O-alkyl group having 1, 2, 3, 4, 5, 6, 7, 8, 9, 10, 11, 12, 13, 14, 15, 16, 17, 18, 19 or 20 C atoms, for example methoxy, ethoxy, iso-propoxy, n-propoxy, iso-butoxy, n-butoxy, tert-butoxy, n-pentyloxy, 1-, 2- or 3-methylbutyloxy, 1,1-, 1,2- or 2,2-dimethylpropoxy, 1-ethylpropoxy, n-hexyloxy, n-heptyloxy, n-octyloxy, ethylhexyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, n-nonadecyloxy and n-eicosyloxy which may be partially or completely halogenated or preferably may be partially or completely fluorinated. A preferred completely fluorinated alkoxy group is trifluoromethoxy.

A linear or branched thioalkyl group having 1 to 20 C atoms denotes a S-alkyl group having 1, 2, 3, 4, 5, 6, 7, 8, 9, 10, 11, 12, 13, 14, 15, 16, 17, 18, 19 or 20 C atoms, for example thiomethyl, 1-thioethyl, 1-thio-iso-propyl, 1-thio-n-propoyl, 1-thio-iso-butyl, 1-thio-n-butyl, 1-thio-tert-butyl, 1-thio-n-pentyl, 1-thio-1-, -2- or -3-methylbutyl, 1-thio-1,1-, -1,2- or -2,2-dimethylpropyl, 1-thio-1-ethylpropyl, 1-thio-n-hexyl, 1-thio-n-heptyl, 1-thio-n-octyl, 1-thio-ethylhexyl, 1-thio-n-nonyl, 1-thio-n-decyl, 1-thio-n-undecyl, 1-thio-n-dodecyl, 1-thio-n-tridecyl, 1-thio-n-tetradecyl, 1-thio-n-pentadecyl, 1-thio-n-hexadecyl, 1-thio-n-heptadecyl, 1-thio-n-octadecyl, 1-thio-n-nonadecyl and 1-thio-n-eicosyl which may be partially or completely halogenated or preferably may be partially or completely fluorinated. A preferred completely fluorinated thioether group is trifluoromethyl thioether.

Preferred alkyl and alkoxy radicals have 1, 2, 3, 4, 5, 6, 7, 8, 9 or 10 C atoms.

An aryl group in the context of this invention contains 6 to 40 ring atoms and a heteroaryl group in the context of this invention contains 5 to 40 ring atoms comprising at least one heteroatom. The heteroatoms are preferably selected from N, O and/or S. An aryl group or heteroaryl group is understood here to mean either a simple aromatic cycle, i.e. phenyl, or a simple heteroaromatic cycle, for example pyridinyl, pyrimidinyl, thiophenyl, etc., or a fused (anelated) aryl or heteroaryl group, for example naphthyl, anthracenyl, phenanthrenyl, quinolinyl or isoquinolinyl.

An aryl group or heteroaryl group is preferably derived from benzene, naphthalene, anthracene, phenanthrene, pyrene, benzanthracene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Aryl with 6 to 14 C atoms is preferably an aryl group selected from the group consisting of phenyl, naphthyl or anthryl, particularly preferably phenyl.

In one particularly preferred embodiment of the invention, the polymeric optical material comprising the polymeric matrix comprising covalently bound photoactive units of the artificial lens to be used in the process according to the invention contains a polymerized monomer according to formula (3), (3)

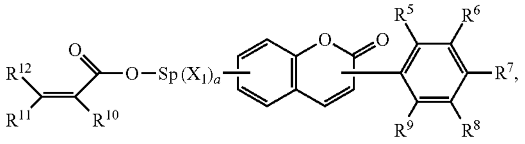

where $X_1$, a, $R^5$ to $R^9$ and $R^{10}$ to $R^{12}$ have a meaning as described before.

In one particularly preferred embodiment of the invention, the polymeric optical material comprising the polymeric matrix comprising covalently bound photoactive units of the artificial lens to be used in the process according to the invention contains a polymerized monomer according to formula (4), (4)

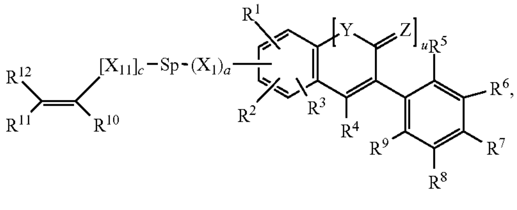

where u is 0, Y is $X^1$, $X_{11}$ is selected from the group consisting of, O—$SO_2$, $SO_2$—O, OC(═O), C(═O)O, S(C═O) and (C═O)S, c is 1, and $X^1$, $X_1$, a, Sp, $R^0$, $R^1$, $R^2$, $R^3$, $R^4$, $R^5$, $R^6$, $R^7$, $R^8$, $R^9$, $R^{10}$, $R^{11}$, $R^{12}$, and R have a meaning as described before.

In one particularly preferred embodiment of the invention, the polymeric optical material comprising the polymeric matrix comprising covalently bound photoactive units of the artificial lens to be used in the process according to the invention contains a polymerized monomer according to formula (5), (5)

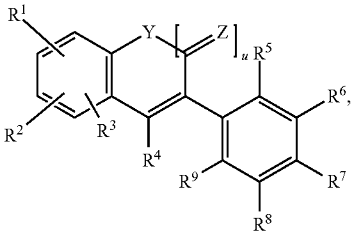

where u is 0, Y is $X^1$, $X_{11}$ is selected from the group consisting of, O—$SO_2$, $SO_2$—O, OC(═O), C(═O)O, S(C═O) and (C═O)S, c is 1, and $X^1$, $X_1$, a, Sp, $R^1$, $R^1$, $R^2$, $R^3$, $R^4$, $R^5$, $R^6$, $R^7$, $R^8$, $R^9$, $R^{10}$, $R^{11}$, $R^{12}$, and R have a meaning as described before.

$R^5$, $R^6$, $R^7$, $R^8$ und $R^9$ are preferably independently of each other selected from H, F, Cl, Br, I, a straight-chain or branched alkyl group having 1 to 20 C atoms, a straight-chain or branched alkoxy group having 1 to 20 C atoms, a partially or fully halogenated straight-chain or branched alkyl group having 1 to 20 C atoms, a partially or fully halogenated straight-chain or branched alkoxy group having 1 to 20 C atoms, and an aryl or heteroaryl group with 5 to 40 ring atoms, where at least one radical selected from $R^5$ to $R^9$ is a straight-chain or branched alkyl or alkoxy group having 1 to 20 C atoms which may be partially or fully halogenated for compounds according to formulae (1) or (3).

$R^5$, $R^6$, $R^7$, $R^8$ und $R^9$ are preferably independently of each other selected from H, F, Cl, Br, I, a straight-chain or branched alkyl group having 1 to 20 C atoms, a straight-chain or branched alkoxy group having 1 to 20 C atoms, a partially or fully halogenated straight-chain or branched alkyl group having 1 to 20 C atoms, a partially or fully halogenated straight-chain or branched alkoxy group having 1 to 20 C atoms, and an aryl or heteroaryl group with 5 to 40 ring atoms for compounds according to formulae (2), (4) or (5).

In compounds of formulae (1), (2), (3), (4) or (5), Sp is preferably unsubstituted.

In compounds of formulae (1), (2), (3), (4) or (5), $R^{11}$ and $R^{12}$ are preferably H.

In compounds of formulae (1), (2), (3), (4) or (5), $R^{10}$ is preferably H or methyl.

In compounds of formulae (1) or (2), $R^5$ is preferably H.

In compounds of formulae (1) or (2), $R^6$ is preferably H.

In compounds of formulae (1) or (2), $R^8$ is preferably H.

In compounds of formulae (1) or (2), $R^9$ is preferably a straight-chain or branched alkyl or alkoxy group having 1 to 6 C atoms, which may be partially or fully fluorinated, and $X_1$, a, $R^5$ to $R^8$ and $R^{10}$ to $R^{12}$ have a meaning as described before or preferably described before.

In compounds of formulae (1) or (2), $R^7$ is preferably a straight-chain or branched alkyl group having 2 to 8 C atoms, which may be partially or fully fluorinated, and $X_1$, a, $R^5$ to $R^6$, $R^9$ and $R^{10}$ to $R^{12}$ have a meaning as described before or preferably described before.

In compounds of formulae (2), (4) or (5), $R^1$, $R^2$, $R^3$ and $R^4$ are preferably H.

In compounds of formulae (2) or (4), $R^5$, $R^6$, $R^7$, $R^8$ and $R^9$ are preferably independently of each other selected from H, F, a straight-chain or branched alkyl group having 1 to 20 C atoms, a straight-chain or branched alkoxy group having 1 to 20 C atoms, a partially or fully halogenated straight-chain or branched alkyl group having 1 to 20 C atoms, a partially or fully halogenated straight-chain or branched alkoxy group having 1 to 20 C atoms.

In compounds of formula (4), $R^5$, $R^6$, $R^7$, $R^8$ and $R^9$ are all preferably H or one or two of $R^5$, $R^6$, $R^7$, $R^8$ and $R^9$ are F or an alkyl group having 1 to 8 C atoms, which may be partially or fully fluorinated, and the other substituents are H.

In compounds of formula (5), $R^5$, $R^6$, $R^7$, $R^8$ and $R^9$ are all preferably H beside the one substituent being of formula (2-1) as described before or preferably described before.

In a further embodiment of the invention, the polymeric optical material comprising the polymeric matrix of the artificial lens to be used in the process according to the invention contains a polymerized monomer selected from compounds (M-1) to (M-68) and (A-01) to (A-16):

(M-1)

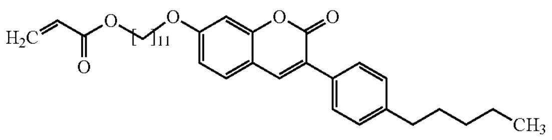

(M-2)

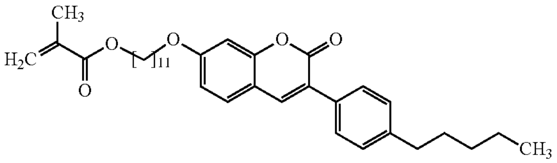

(M-3)

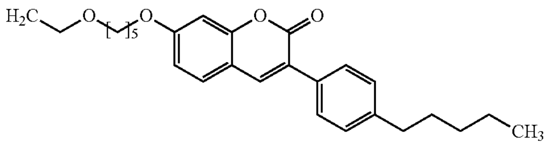

(M-4)

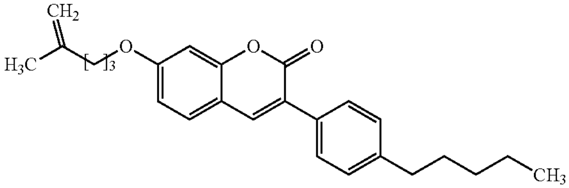

(M-5)

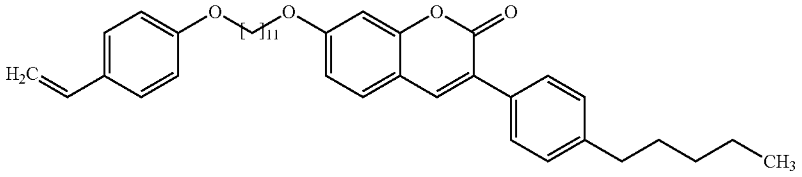

(M-6)

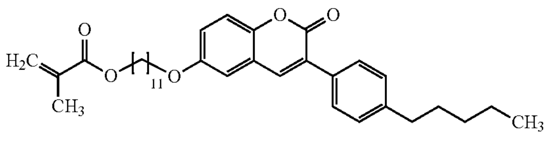

(M-7)

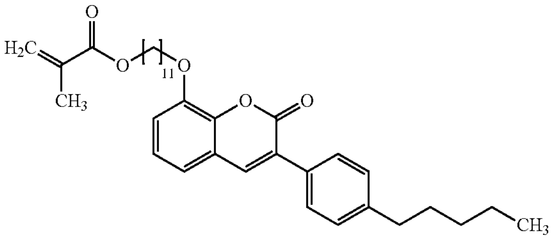

(M-8)

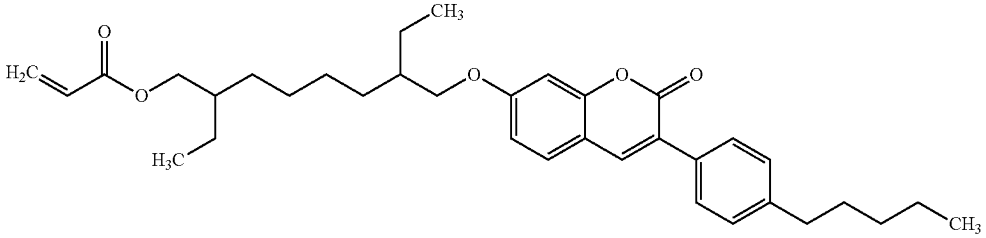

(M-9)

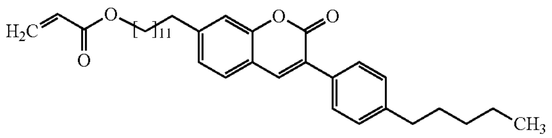

(M-10)

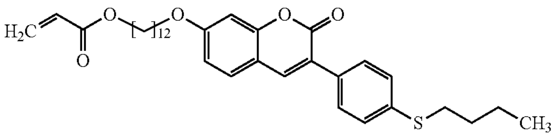

-continued
(M-11)
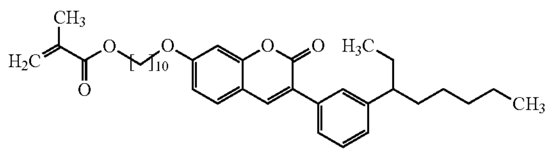
(M-12)
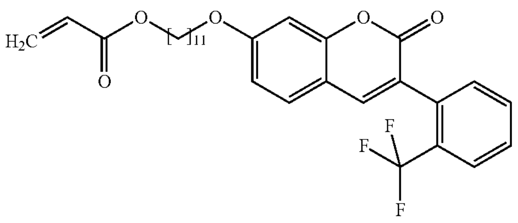
(M-13)
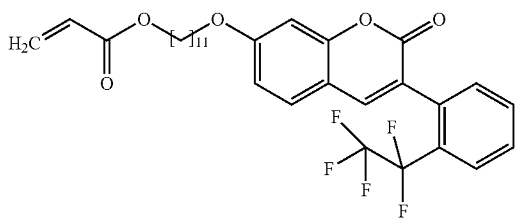
(M-14)
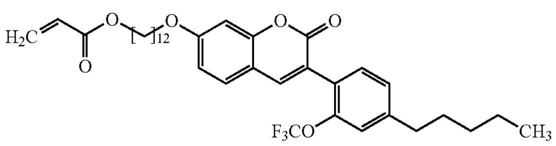
(M-15)
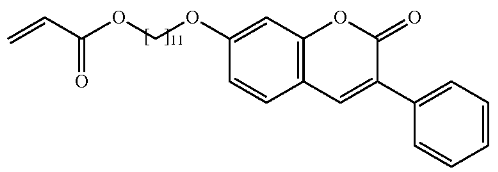
(M-16)
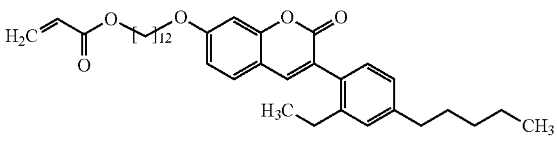
(M-17)
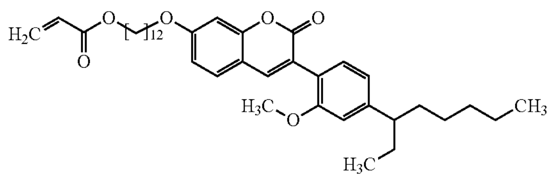
(M-18)
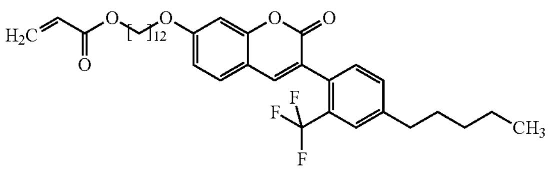
(M-19)
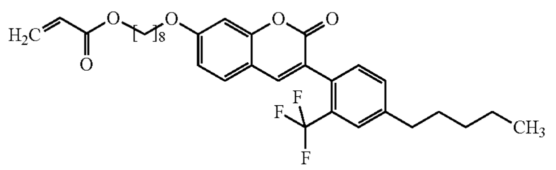
(M-20)
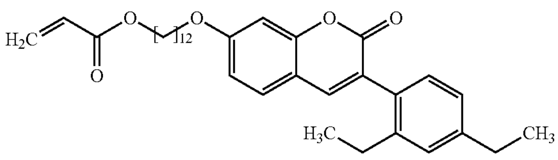
(M-21)
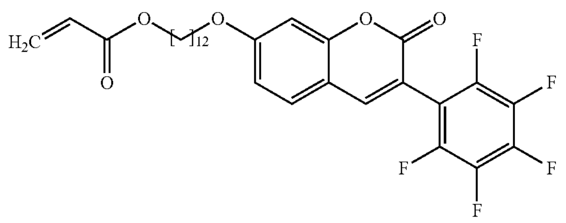
(M-22)
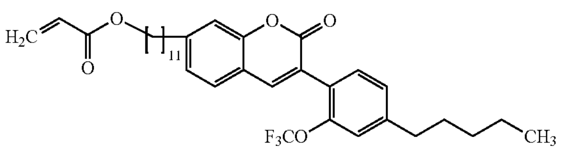
(M-23)
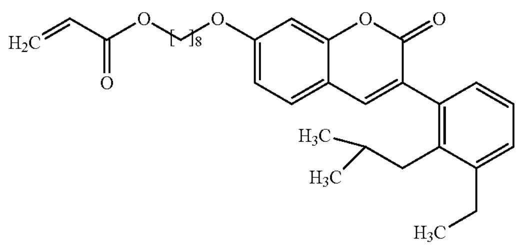
(M-24)
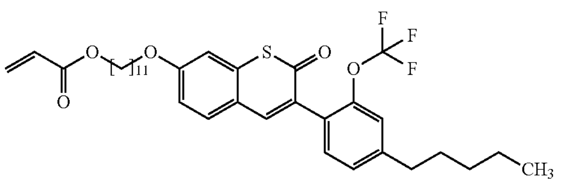

-continued
(M-25)
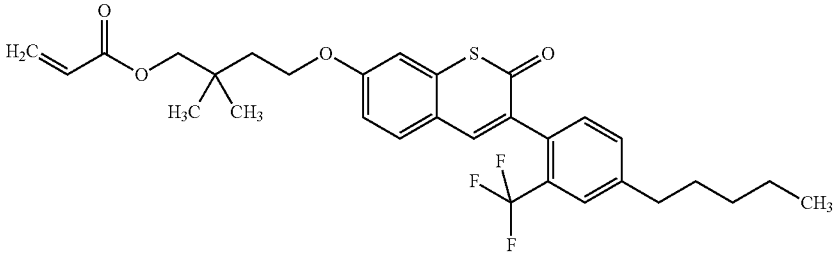
(M-26)
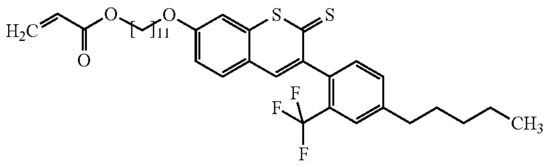
(M-27)
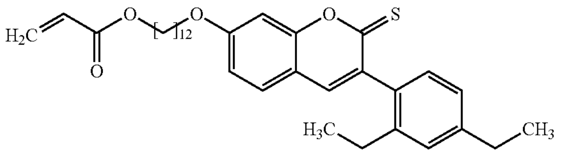
(M-28)
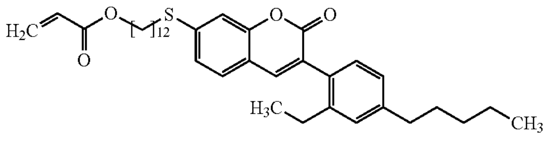
(M-29)
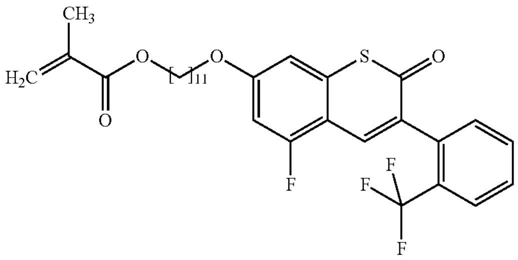
(M-30)
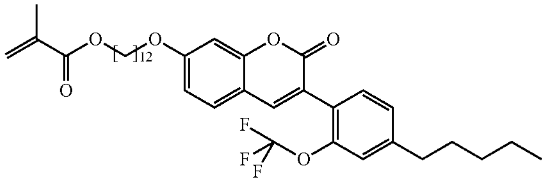
(M-31)
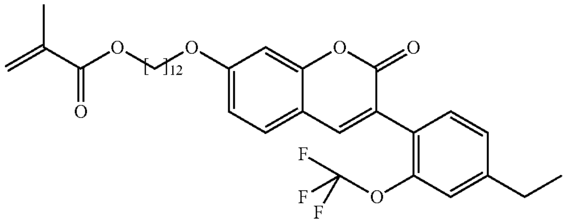
(M-32)
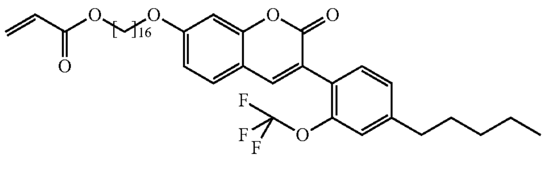
(M-33)
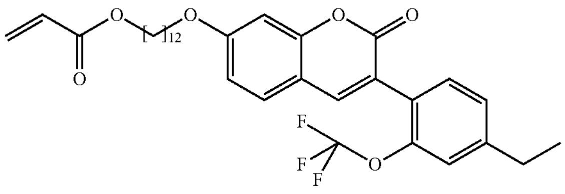
(M-34)
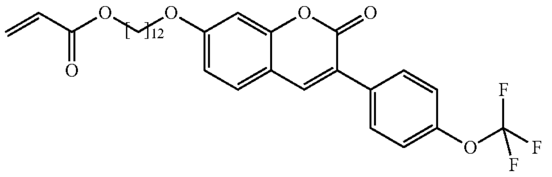
(M-35)
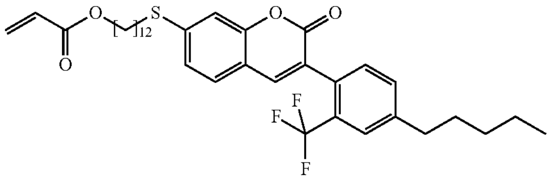
(M-36)
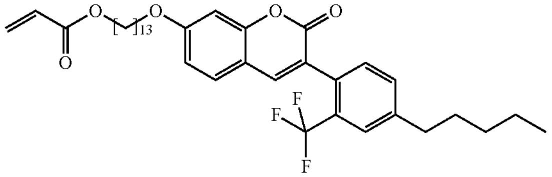
(M-37)
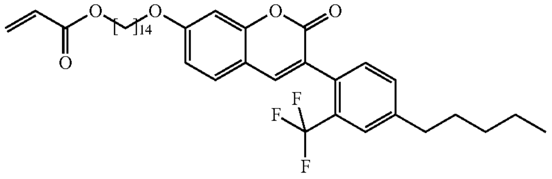

-continued
(M-38)
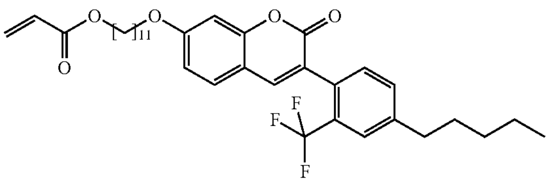
(M-39)
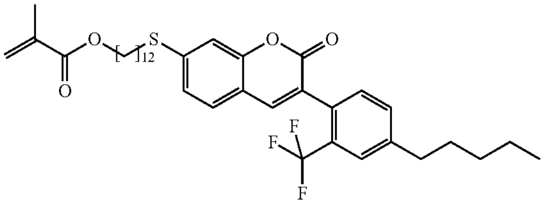
(M-40)
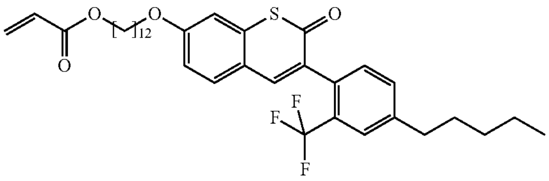
(M-41)
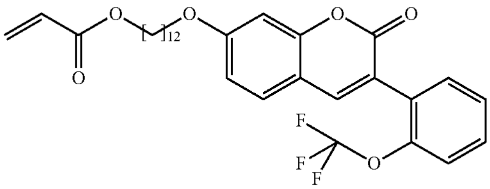
(M-42)
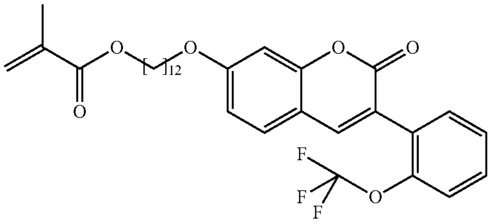
(M-43)
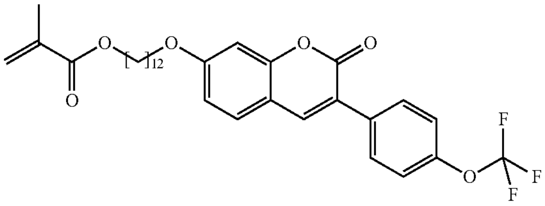
(M-44)
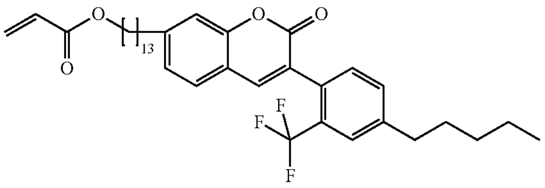
(M-45)
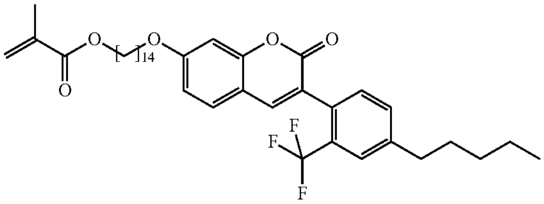
(M-46)
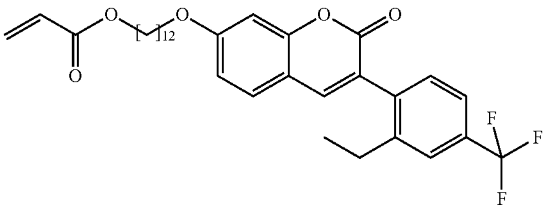
(M-47)
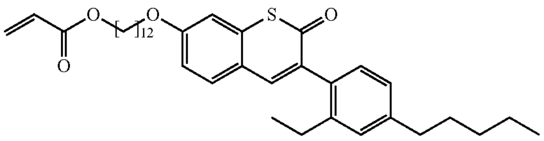
(M-48)
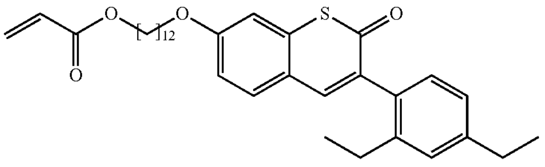
(M-49)
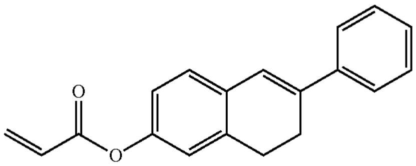
(M-50)
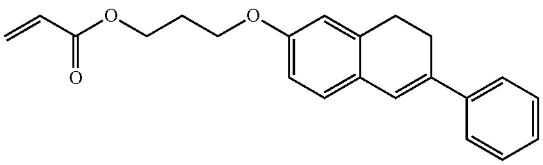
(M-51)
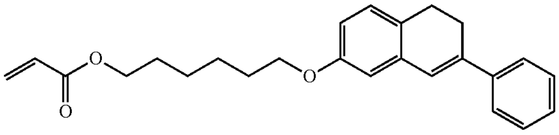

-continued
(M-52)
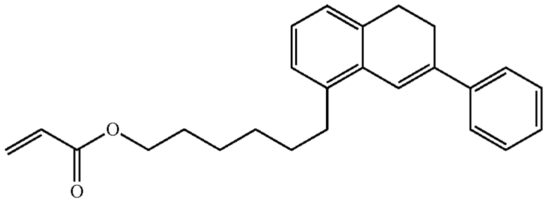
(M-53)
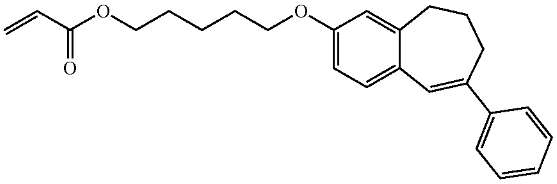
(M-54)
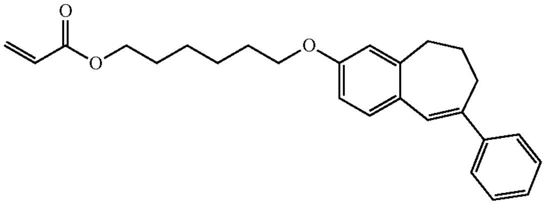
(M-55)
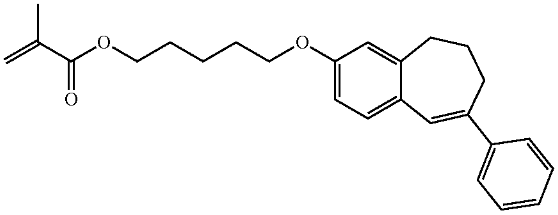
(M-56)
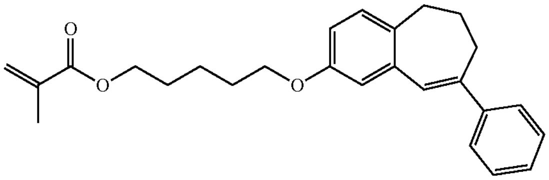
(M-57)
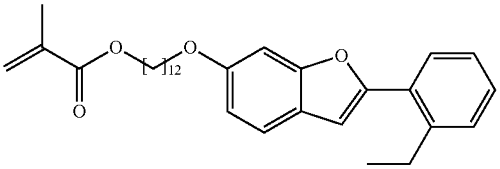
(M-58)
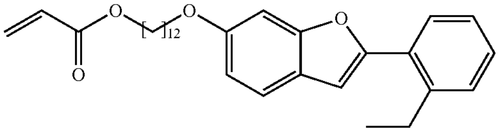
(M-59)
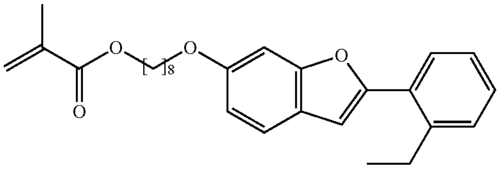
(M-60)
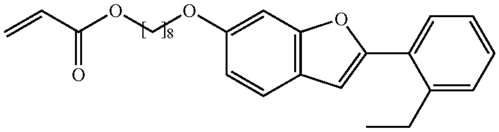
(M-61)
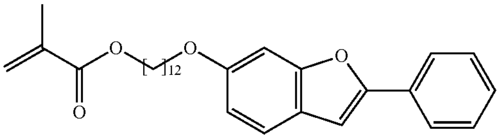
(M-62)
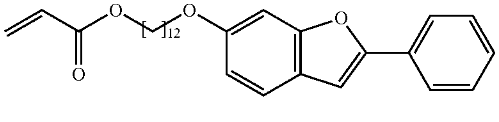
(M-63)
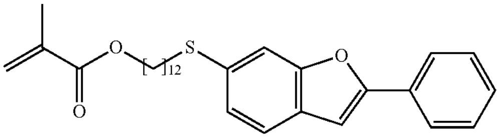
(M-64)
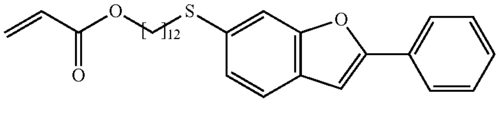
(M-65)
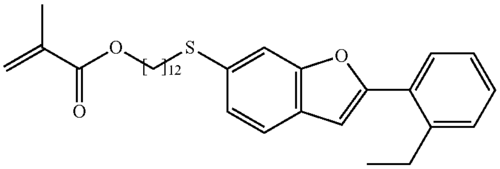

-continued
(M-66)
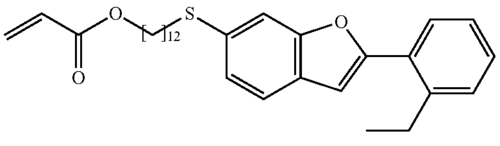
(M-67)
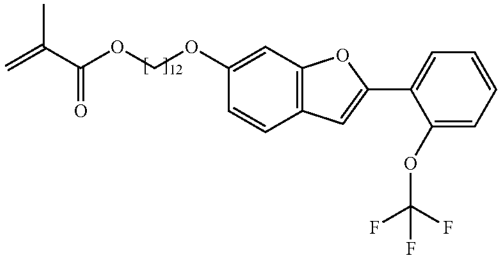
(M-68)
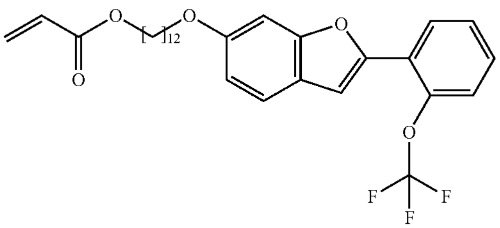
(A-1)
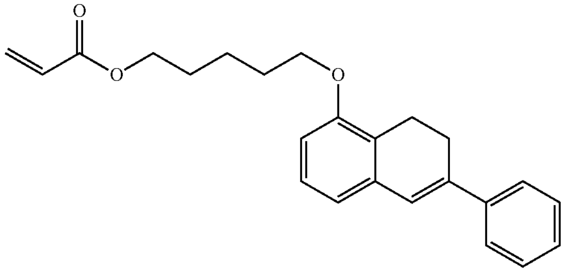
(A-2)
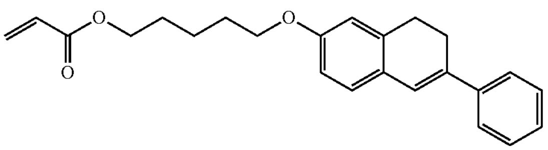
(A-3)
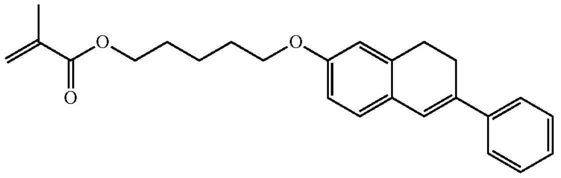
(A-4)
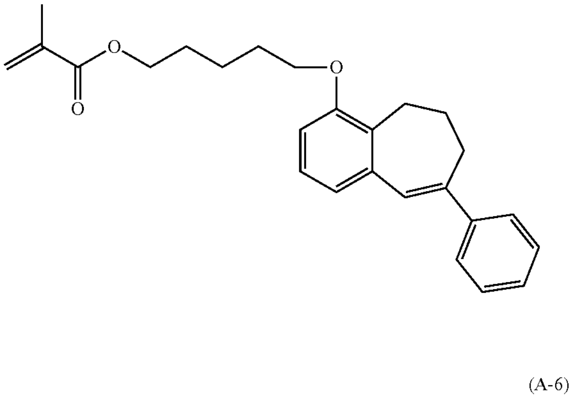
(A-5)
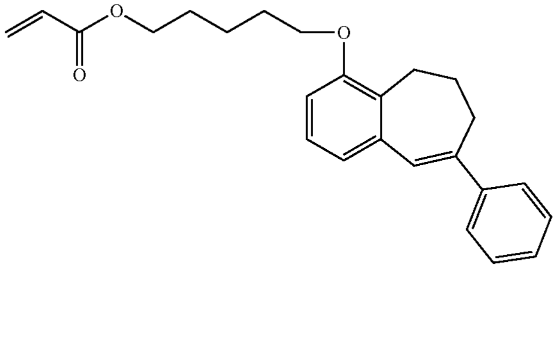
(A-6)
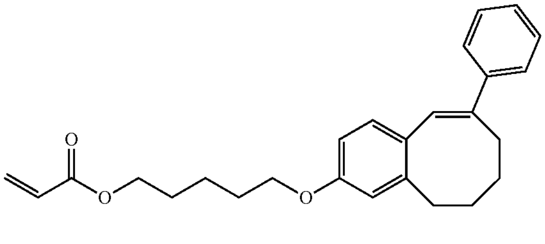
(A-7)
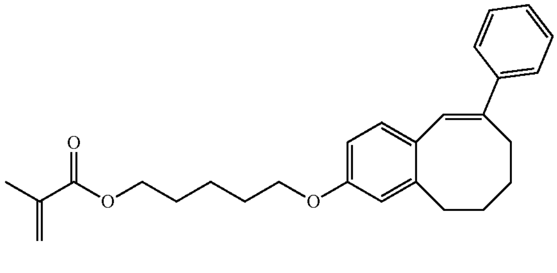

-continued
(A-8)
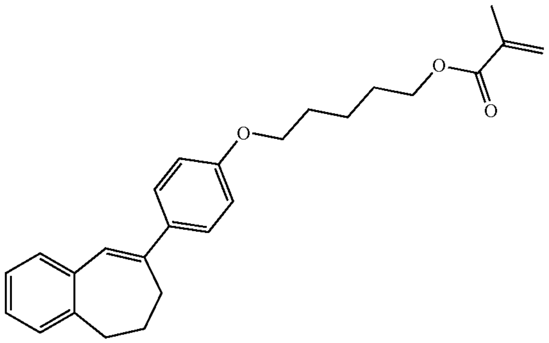
(A-9)
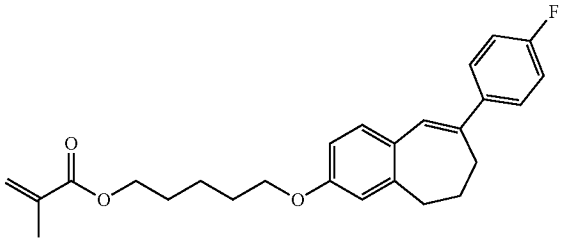
(A-10)
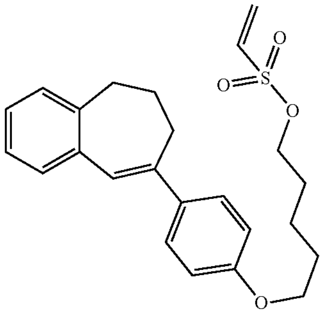
(A-11)
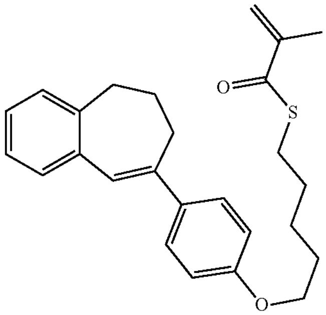
(A-12)
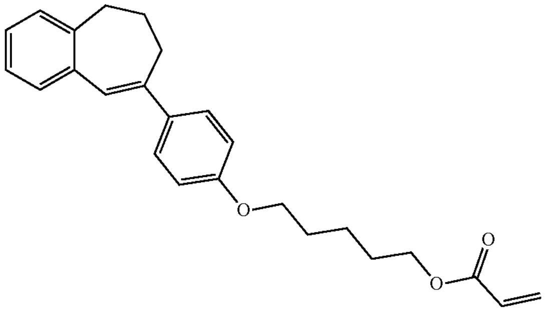
(A-13)
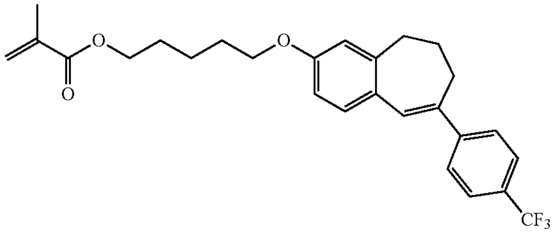
(A-14)
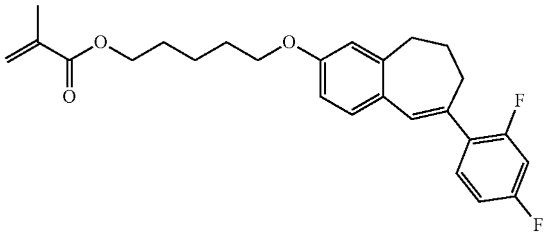
(A-15)
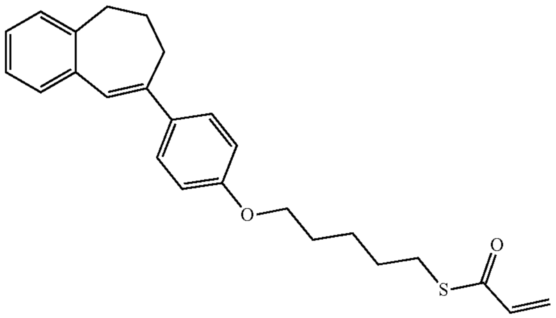
(A-16)
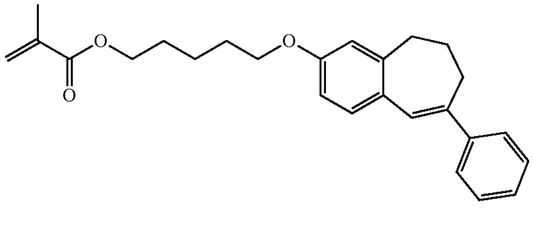
.

In a further embodiment of the invention, the polymeric optical material comprising the polymeric matrix contains a polymerized monomer selected from compounds (M-12), (M-14), (M-15), (M-18), (M-53), (M-55), (M-67), (A-01) to (A-16).

In a further very preferred embodiment of the invention, the polymeric matrix of the polymeric optical material to be used in the process according to the invention is a copolymeric matrix comprising polymerized monomers comprising photoactive units as described or preferably described before or polymerized compounds of formulae (1) to (5) as described before or polymerized compounds (M-1) to (M-68) and (A-01) to (A-16) and further polymerized monomers as known in the art.

Examples for monomers which are co-polymerized with the monomers comprising photoactive units as described or preferably described before building the polymeric optical material for the artificial lens (e.g. contact lens or IOL) may be selected from the group consisting of styrene, ethoxyethyl methacrylate (EOEMA), methyl methacrylate (MMA), methyl acrylate, n-alkyl acrylates (the n-alkyl group comprising 2-20 C-atoms), n-alkyl methacrylates (the n-alkyl group comprising 2-20 C-atoms), i-alkyl acrylates (the i-alkyl group comprising 3-20 C-atoms), i-alkyl methacrylates (the i-alkyl group comprising 3-20 C-atoms), ethoxyethoxy ethylacrylate (EEEA), 2-hydroxyethyl methacrylate (HEMA), tetrahydrofuryl methacrylate (THFMA), glycidylmethacrylate (GMA), 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate (EGPEA), heptafluorobutyl acrylate, heptafluorobutyl methacrylate, hexafluorobutyl acrylate, hexafluorobutyl methacrylate, hexafluoroisopropyl acrylate, hexafluoroisopropyle methacrylate, octafluoropentyl acrylate, octafluoropentyl methacrylate, petanfluoropropyl acrylate, pentafluoropropyl methacrylate, tetrafluoropropyl methacrylate, trifluoroethyl acrylate, trifluoroethyl methacrylate, Bisphenol A diacrylate-1 EO/Phenol (BPADA), 2-[3'-2'H-benzotriazol-2'-yl)-4'-hydroxyphenyl]ethyl methacrylate (BTPEM) or ehtyleneglycoldimethacrylate.

Preferred examples for monomers which are co-polymerized with the monomers comprising photoactive units as described or preferably described before building the polymeric optical material for the artificial lens (e.g. contact lens or IOL) are selected from methyl methacrylate, 2-hydroxyethyl methacrylate, 2-phenoxyethyl acrylate, ethoxyethoxy ethylacrylate, 8-methylnonyl methacrylate, n-butyl methacrylate, 2-ethyl hexylmethacrylate or a mixture thereof.

Suitable UV-absorber are 2-(3-(t-butyl)-4-hydroxy-5-(5-methoxy-2-benzotriazolyl)phenoxy)ethyl methacrylate, 3-(3-(t-butyl)-4-hydroxy-5-(5-methoxy-2-benzotriazolyl) phenoxy)propyl methacrylate, 3-(3-t-Butyl-5-(5-chlorobenzotriazol-2-yl)-4-hydroxyphenyl)propyl methacrylate, 3-(3-(tert-Butyl)-4-hydroxy-5-(5-methoxy-2H-benzo[d][1,2,3] triazol-2-yl)phenoxy)propylmethacrylat, 2-(2-Hydroxy-5-vinylphenyl)-2H-benzotriazol, Allyl-2-hydroxybenzophenon, 2-Allyl-6-(2H-benzotriazol-2-yl)-p-cresol, 4-Methacryloxy-2-hydroxybenzophenon, 2-(2'-Hydroxy-3'-methallyl-5'-methylphenyl)benzotriazol, 2-Hydroxy-4-methacryloyloxybenzophenon, 4-Acryloylethoxy-2-hydroxybenzophenon, 2-[3-(2H-Benzotriazol-2-yl)-4-hydroxyphenyl]ethylmethacrylat, 2-(2'-Hydroxy-5'-methacrylamidophenyl)-5-methoxybenzotriazol, 2-(2'-Hydroxy-5'-methacrylamidophenyl)-5-chlorobenzotriazol, 2-(2'-Hydroxy-5'-methacryloxypropylphenyl)benzotriazol, 2-(2'-Hydroxy-g-methacryloylpropyl-3'-tert-butyl-phenyl)-5-methoxy-2H-benzotriazol, 2-(3-(tert-Butyl)-4-hydroxy-5-(5-methoxy-2H-benzo[d][1,2,3]triazol-2-yl)phenoxy)ethyl-methacrylat, 2-[3'-tert-Butyl-2'-hydroxy-5'-(3"-methacryloyloxypropyl)phenyl]-5-chlorbenzotriazol, 2-{2'-Hydroxy-3'-tert-butyl-5'-[3'-methacryloyloxypropoxy] phenyl}-5-methoxy-2H-benzotriazol, 2-[3'tert-Butyl-5'-(3"-dimethylvinylsilylpropoxy)-2'-hydroxyphenyl]-5-methoxybenzotriazol, 2-(tert-Butyl)-6-(5-chloro-2H-benzo [d][1,2,3]triazol-2-yl)-4-vinylphenol, 2-(2H-1,2,3-benzotriazol-2-yl)-4-methyl-6-(2-methylprop-2-enyl) phenol, 2-(3-acetyl-2-aminophenoxy)ethyl methacrylat, 2-(4-benzoyl-3-hydroxyphenoxy)ethyl acrylat or a combination of this compounds.

Preferred UV-Absorber are selected from the group of 2-[3'-2'H-benzotriazol-2'-yl)-4'-hydroxyphenyl]ethyl methacrylate (BTPEM), 2-(3-(t-butyl)-4-hydroxy-5-(5-methoxy-2-benzotriazolyl)phenoxy)ethyl methacrylate, 3-(3-(t-butyl)-4-hydroxy-5-(5-methoxy-2-benzotriazolyl)phenoxy) propyl methacrylate, 3-(3-t-Butyl-5-(5-chlorobenzotriazol-2-yl)-4-hydroxyphenyl)propyl methacrylate which may be polymerized together with the monomers according to formulae (1), (2), (3), (4) or (5).

Suitable crosslinker to be used in copolymers comprising polymerized monomers of formulae (1), (2), (3), (4) or (5) building the polymeric optical material of the artificial lens (contact lens or IOL) are selected from the group of poly (ethylene glycol) diacrylate, poly(ethylene glycol) dimethacrylate, ethyleneglycoldimethacrylate (EGDMA), ethylenegly coldiacrylate, 1,3-propanedioldiacrylat, 1,6-hexanedioldiacrylate, 1,8-octanedioldiacrylate, 1,11-undecandioldiacrylate, 1,12-dodecyldiacrylate, 1,15-pentadecandioldiacrylate, 1,16-hexadecanedioldiacrylate, 1,18-octadecanedioldiacrylate, 1,3-propanedioldimethacrylate, 1,6-hexanedioldimethacrylate, 1,8-octanedioldimethacrylate, 1,11-undecandioldimethacrylate, 1,12-dodecyldimethacrylate, 1,15-pentadecanedioldimethacrylate, 1,16-hexadecanedioldimethacrylate, 1,18-octadecanedioldimethacrylate.

If the refractive index needs to be increased, another area of wavelengths may be applied to the artificial lens (contact lens or IOL) made out of one or more polymers being capable of changing the polarizability. 400-590 nm may be used, preferably 500-580 nm, most preferably 530-570 nm.

In the following, the optical material of the artificial lens to be used in the process according to the invention, preferably the polymeric optical material of the contact lens or IOL, is further and preferably described for the area of wavelengths from 400 nm to 590 nm, preferably from 500 nm to 580 nm, particular preferably from 530 nm to 570 nm for locally increasing the polarizability of said material.

To apply this adjustment, the polymeric optical material has a refractive index ranging from 1.45 to 1.60.

The polymeric optical material of the artificial lens (contact lens or IOL) for said adjustment can optionally contain an ultraviolet light blocker or a blue light absorber as described before.

Said polymeric optical material of the artificial lens as used in the process according to the invention for said adjustment comprises a polymeric matrix comprising covalently bound dimerized photoactive units, preferably in an amount of at least 2 wt % to 100 wt %, preferably 5 wt % to 90 wt %, most preferably 7 wt % to 80 wt %.

The dimerized photoactive units within said polymeric matrix can be the same or different.

The polymeric matrix of the polymeric optical material of the artificial lens and/or IOL for said adjustment can be a matrix from homopolymers or copolymers, preferably from copolymers.

Said polymeric matrix comprising said dimerized photoactive units can be a matrix from silicon-containing polymers, acrylic polymers, methacrylic polymers or mixtures thereof.

A dimerized photoactive unit means a photochemically active unit which is photochemically active in the area of 400 nm to 590 nm wavelengths as described or preferably described before under the effect of a two-photon or multi-photon process.

The polymeric matrix of the polymeric optical material of the lens and/or IOL for said adjustment comprises dimerized photoactive units which are able to separate under the effect of the two-photon or generally multi-photon process.

Therefore, the invention further relates to a process for adjusting a polarizability of an artificial lens (preferably at one or more particular locations of said lens) comprising a body formed of a polymeric optical material, wherein said polymeric optical material of the artificial lens comprises a polymeric matrix comprising covalently bound dimerized photoactive units as sole photoactive units which are able to separate under the effect of the two-photon or generally multi-photon process.

Preferably, dimerized photoactive units comprise a cyclobutane ring which will be cleaved under the effect of the two-photon or generally multiphoton process.

Alternatively, dimerized photoactive units are particularly preferred comprising a cyclobutane ring which is able to be cleaved under the effect of the two-photon or generally multi-photon process.

Therefore, the invention further relates to a process for adjusting a polarizability of an artificial lens (preferably at one or more particular locations of said lens) comprising a body formed of a polymeric optical material, wherein said polymeric optical material of the artificial lens comprises a polymeric matrix comprising covalently bound dimerized photoactive units comprising a cyclobutane ring as sole photoactive units which are able to cleave under the effect of the two-photon or generally multi-photon process.

The cleavage of said dimerized photoactive units comprising a cyclobutane ring is visualized in scheme 1 as described before.

In one preferred embodiment of the invention, the polymeric optical material comprising the polymeric matrix comprising dimerized photoactive units of the artificial lens to be used in the process according to the invention is derived from a polymerized monomer according to formulae (1), (2), (3), (4) or (5) as described before or preferably described before.

In a further embodiment of the invention, the polymeric optical material comprising the polymeric matrix comprising dimerized photoactive units of the artificial lens to be used in the process according to the invention is derived from a polymerized monomer selected from compounds (M-1) to (M-68) and (A-01) to (A-16) as described before.

In a further very preferred embodiment of the invention, the polymeric matrix of the polymeric optical material to be used in the process according to the invention is a copolymeric matrix comprising polymerized monomers comprising dimerized photoactive units as described or preferably described before or is derived from polymerized compounds of formulae (1) to (5) as described before or is derived from polymerized compounds (M-1) to (M-68) and (A-01) to (A-16) and further polymerized monomers as known in the art.

Examples for monomers, UV absorber and crosslinkers are described before and apply accordingly for this polymeric optical material comprising dimerized photoactive units as described before or preferably described before.

While manufacturing the artificial lens to be used in the process according to the invention, said polymeric matrix comprising partially or fully dimerized photoactive units may be formed via one photon-absorption or two-photon or generally multi-photon absorption of photoactive units able to dimerize by forming a cyclobutane ring by means of a [2π+2π] cycloaddition as described before or preferably described before.

If the process according to the invention is applied in the eye, then two-photon (or, generally, multi-photon) absorption may be used.

To produce the artificial lens comprising a polymeric optical material comprising a polymeric matrix comprising partially or fully dimerized photoactive units to be used in the process according to the invention, two-photon (or, generally, multi-photon) absorption or 1-photon absorption via any irradiation means such as a UV lamp with special wavelength filter, a UV LED with one of the wavelengths specified above or a laser with a wavelength as specified above may be used.

To produce the artificial lens comprising a polymeric optical material comprising a polymeric matrix comprising partially or fully dimerized photoactive units to be used in the process according to the invention, 1-photon absorption via any irradiation means such as a UV lamp with special wavelength filter, a UV LED with one of the wavelengths specified above or a laser with a wavelength as specified above is preferably used.

For the manufacture of the artificial lens comprising a polymeric optical material comprising a polymeric matrix comprising partially or fully dimerized photoactive units to be used in the process according to the invention, the same irradiation source may be used as described for the system according to the invention as described before by doubling the frequency of the feed laser or an optical power amplifier may be used or another irradiation source may be used. Preferably, another irradiation source is used for the manufacture of said artificial lens.

The invention relates further to a process for adjusting a polarizability of an artificial lens comprising a body formed of a polymeric optical material based on a two- or multi-photon absorption process, the process comprising the steps of:

providing said artificial lens; and adjusting the polarizability of said lens through irradiation of said lens by using a system as described before or preferably described before, wherein the provided artificial lens comprises a polymeric matrix comprising covalently bound photoactive units comprising a non-aromatic double bond which is able to dimerize by forming a cyclobutane ring by means of a [2π+2π] cycloaddition as described before or preferably described before, and wherein said provided artificial lens is irradiated with the irradiation beam of the first wavelength, said irradiation causes the dimerization of said photoactive units thereby decreasing the polarizability of said artificial lens and thereby modifying the provided artificial lens in that the modified artificial lens comprises a polymeric matrix comprising partially or fully dimerized photoactive units derived from said [2π+2π] cycloaddition and optionally irradiating said modified artificial lens with an irradiation beam of the second wavelength for locally increasing the polarizability of said modified artificial lens by partially cleaving said dimerized photoactive units.

The invention relates further to a process for adjusting a polarizability of an artificial lens comprising a body formed of a polymeric optical material based on a two- or multi-photon absorption process, the process comprising the steps of:

providing said artificial lens; and adjusting the polarizability of said lens through irradiation of said lens by using a system as described before or preferably described before, wherein the provided artificial lens comprises a polymeric matrix comprising covalently bound dimerized photoactive units as sole photoactive units which are able to separate under the effect of the two-photon or generally multi-photon process as described before or preferably described before, and wherein the provided artificial lens is irradiated with the irradiation beam of the second wavelength, said irradiation causes the separation of said dimerized photoactive units thereby increasing the polarizability of said artificial lens and thereby modifying the provided artificial lens in that the modified artificial lens comprises a polymeric matrix comprising photoactive units able to dimerize again and optionally irradiating said modified artificial lens with an irradiation beam of the first wavelength for locally decreasing the polarizability of said modified artificial lens by partially dimerizing said photoactive units.

The invention relates further to a process for adjusting a polarizability of an artificial lens comprising a body formed of a polymeric optical material based on a two- or multi-photon absorption process, the process comprising the steps of:

providing said artificial lens; and adjusting the polarizability of said lens through irradiation of said lens by using a system as described before or preferably described before, wherein the provided artificial lens comprises a polymeric matrix comprising covalently bound photoactive units comprising a non-aromatic double bond which is able to dimerize by forming a cyclobutane ring by means of a [2π+2π] cycloaddition under the effect of the two-photon or multi-photon process together with already dimerized photoactive units as described before or preferably described before, and wherein the provided artificial lens is irradiated with the irradiation beam of the first wavelength said irradiation causes the dimerization of said photoactive units thereby decreasing the polarizability of said artificial lens and thereby modifying the provided artificial lens in that the modified artificial lens comprises a polymeric matrix comprising more dimerized photoactive units derived from said [2π+2π] cycloaddition, or wherein the provided artificial lens is irradiated with the irradiation beam of the second wavelength, said irradiation causes the separation of said dimerized photoactive units thereby increasing the polarizability of said artificial lens and thereby modifying the provided artificial lens in that the modified artificial lens comprises a polymeric matrix comprising more photoactive units able to dimerize by forming a cyclobutane ring by means of a [2π+2π] cycloaddition.

The invention further relates to a method for locally adjusting a polarizability of an intraocular lens comprising a polymeric optical material as described before or preferably described before arranged within an eye of a patient, the method comprising:

exposing the intraocular lens to an irradiation beam having a wavelength between 600 nm and 800 nm to locally decrease the polarizability of the intraocular lens or exposing the intraocular lens to an irradiation beam having a wavelength between 400 nm and 590 nm to locally increase the polarizability of the intraocular lens, preferably using the system and/or the process as described before.

The invention further relates to a method for locally adjusting a polarizability of an intraocular lens comprising a polymeric optical material as described before or preferably described before arranged within an eye of a patient, the method comprising:

exposing the intraocular lens to a first irradiation beam having a first wavelength between 600 nm and 800 nm to locally decrease the polarizability of the intraocular lens; and exposing the intraocular lens to a second irradiation beam having a second wavelength between 400 nm and 590 nm to locally increase the polarizability of the intraocular lens, thereby preferably using the system and/or the process as described before.

The invention further relates to a method for locally adjusting a polarizability of an intraocular lens comprising a polymeric optical material as described before or preferably described before arranged within an eye of a patient, wherein said exposing of the intraocular lens comprises scanning a said irradiation beam across the intraocular lens based on input data relating to lens data of the intraocular lens, in particular relating to the polymeric optical material, and/or treatment plan data relating to a treatment plan for treating the intraocular lens based on said exposing the intraocular lens to said irradiation beam.

The invention further relates to a method for locally adjusting a polarizability of an intraocular lens comprising a polymeric optical material as described before or preferably described before arranged within an eye of a patient, wherein the lens data comprises data relating to one or more of a dimension (for example diameter and/or thickness) of the intraocular lens, a material, in particular the polymeric optical material, of which the intraocular lens is comprised as described before or preferably described before, the refractive index of the intraocular lens, and a mapping of the refractive index to a specific location/coordinates of the intraocular lens.

The invention further relates to a method for locally adjusting a polarizability of an intraocular lens comprising a polymeric optical material as described before or preferably described before arranged within an eye of a patient, wherein the treatment plan data comprises one or more of:

scan strategy control command data of a scan strategy (for example a scanning pattern and/or a scanning sequence and/or a scanning speed and/or a scanning duration of the scanning pattern and/or a scanning duration of the scanning sequence and/or a pulse duration of a pulse of the irradiation beam of the first and/or second wavelength and/or an irradiation beam profile of a said irradiation beam and/or a radiation (photon) density and/or a radiation intensity and/or a radiation power and/or radiation wavelength) for said scanning of a said irradiation beam across the intraocular lens, temperature data of a current and/or predicted temperature of the intraocular lens during said exposure, refractive index data of a refractive index of the intraocular lens to be obtained based on said exposure, the refractive index to be obtained in particular relating to a mapping of the refractive index to be obtained to a specific location/coordinates of the intraocular lens, rhexis dimension data of a dimension of a rhexis, eye data relating to a dimension and/or a shape of the eye of the patient, positioning data relating to a position and/or orientation of the intraocular lens relative to the eye, and registration data relating to an identification of the patient and/or the specific eye of the patient.

The invention further relates to a method for locally adjusting a polarizability of an intraocular lens comprising a polymeric optical material as described before or preferably described before arranged within an eye of a patient, wherein said exposing of the intraocular lens to a said irradiation beam comprises exposing a first volume of the intraocular lens prior to exposing a second volume of the intraocular lens, wherein the first volume is further away from the cornea of the eye of the patient than the second volume.

The invention further relates to a method for locally adjusting a polarizability of an intraocular lens comprising a polymeric optical material as described before or preferably described before arranged within an eye of a patient, wherein the (first) wavelength is between 650 nm and 750 nm, preferably between 670 nm and 720 nm, more preferably between 680 nm and 710 nm.

The invention further relates to a method for locally adjusting a polarizability of an intraocular lens comprising a polymeric optical material as described before or preferably described before arranged within an eye of a patient, wherein the (second) wavelength is between 500 nm and 580 nm, preferably between 530 nm and 570 nm.

In the above-stated clauses, an initial step of the methods may be to provide a said intraocular lens.

In examples, in which said exposing of the intraocular lens to a said irradiation beam comprises exposing a first volume and/or plane and/or location of the intraocular lens prior to exposing a second volume and/or plane and/or location of the intraocular lens, wherein the first volume and/or plane and/or location is further away from the cornea of the eye of the patient than the second volume and/or plane and/or location, volumes and/or planes and/or locations irradiated at later time points in the irradiation sequence may be closer to the cornea than volumes and/or planes and/or locations irradiated at earlier time points. A said volume may hereby relate to one or more planes of the intraocular lens.

Said lens data and treatment plan data are preferably described before and are part of the system to be preferably used for the method for locally adjusting a polarizability of an intraocular lens comprising a polymeric optical material as described before or preferably described before arranged within an eye of a patient as described before.

The invention is furthermore related to a method for correcting vision in a patient by modifying the refractive index of an intraocular lens comprising a polymeric optical material as described before or preferably described before within the eye of said patient comprising identifying and measuring the degree of vision correction of the patient;

determining the position and type of refractive structures to be written into said intraocular lens to correct the patient's vision; and subsequently exposing said intraocular lens to two-photon or multi-photon irradiation having a wavelength between 600 nm and 800 nm to locally decrease the polarizability of the intraocular lens and/or subsequently exposing said intraocular lens to two-photon or multi-photon irradiation having a wavelength between 400 nm and 590 nm to locally increase the polarizability of the intraocular lens, preferably by using the system and/or the process as described before for exposing said intraocular lens to said irradiation.

As outlined above, the change of polarizability results in a change of refractive index, as will be described in more detail in the following.

The speed of light in vacuum $c_0$ is a fundamental constant and describes the speed of an electromagnetic wave in vacuum. From the solutions of Maxwell's equations, the speed of light in vacuum can be related to the electric constant $\varepsilon_0$ and the magnetic constant $\mu_0$. They are also fundamental constants.

$$c_0^2\varepsilon_0\mu_0 = 1 \text{ or } c_0 = \frac{1}{\sqrt{\varepsilon_0\mu_0}}$$

The speed of light when passing through a transparent medium $c_m$, is less than it is in vacuum. The electric constant needs to be substituted by the permittivity $\varepsilon$ and the magnetic constant by the permeability $\mu$.

$$c_m = \frac{1}{\sqrt{\varepsilon\mu}} = \frac{1}{\sqrt{\varepsilon_0\mu_0\varepsilon_r\mu_r}} = \frac{1}{\sqrt{\varepsilon_r\mu_r}}c_o$$

The relative permittivity $\varepsilon_r$ (also called dielectric constant) is a dimensionless, material dependent quantity that gives the permittivity relative to the electric constant. The relative permittivity of vacuum is therefore $\varepsilon_r=1$ which can also be seen by comparing the two above equations. The actual permittivity is then calculated by multiplying the relative permittivity by $\varepsilon_0$ $$\varepsilon=\varepsilon_0\varepsilon_r=(1+\chi_e)\varepsilon_0$$

where $\chi_e$ is the electric susceptibility of the material, a value closely related to $\varepsilon_r$ and defined as $$\chi_e=\varepsilon_r-1$$

The relative permittivity describes how the electric field strength is lowered if the material, also referred to as a dielectric, is placed in an electric field. Relative permittivity is determined by the ability of a material to be polarized in response to the field, and thereby reduce the total electric field within the material. The relative permittivity of most materials is between 1 and 100, however dielectrics with $\varepsilon_r$ of up to 10000 are known. To give a few examples the relative permittivities of polystyrene, cellulose and water are 2.5, 4.5 and 81, respectively. The relative permittivity of air can be regarded as 1 to a good approximation. In general, the relative permittivity is not a constant, as it can vary with the frequency of the field applied, humidity, temperature, and other parameters. In a nonlinear medium, the permittivity can depend on the strength of the electric field. Therefore, the outdated term "dielectric constant" for $\varepsilon_r$ is ambiguous and should not be used anymore.

For a magnetic field the values $\mu_0$, $\mu_r$ and $\mu$ are defined analogous to the corresponding values of the electric field. The permeability is $$\mu=\mu_0\mu_r$$

and the magnetic susceptibility is $$\chi_m = \mu_r - 1$$

By definition, the relative permeability of vacuum is $\mu_r = 1$. The relative permittivity varies with magnetic field strength and is generally a function of frequency. The relative permeability of a substance can also have negative values. One distinguishes diamagnetic substances ($\mu_r < 1$), paramagnetic substances ($\mu_r > 1$) and ferromagnetic substances ($\mu_r >> 1$). Most organic substances like polymers are diamagnetic and their relative permeability is very close to 1.

The refractive index n is a material constant that characterizes the refractive properties of that medium. As already introduced before, the refractive index is the ratio of the speed of light in vacuum to the speed of light in a given medium. Vacuum consequently has a refractive index of 1. The refractive index of water is 1.333. The refractive index of commercially available glassware ranges from 1.4 to 1.9. The refractive indices of most organic polymers are between 1.4 and 1.6, with specially modified high refractive index polymers having an index of refraction of more than 1.7. The refractive index is generally dependent on the frequency of light, a phenomenon called dispersion. Since the refractive index of dry air ($n_{air} \approx 1{,}0003$) is only slightly different from 1, measurements can be made relative to air to a good approximation. In technical optics the refractive index $n^0$ is used. It is defined as $$n^0 = \frac{c_{air}}{c_m}$$

One can obtain the relation $$n = \frac{\sqrt{\varepsilon_0 \mu_0 \varepsilon_r \mu_r}}{\sqrt{\varepsilon_0 \mu_0}} = \sqrt{\varepsilon_r \mu_r}$$

Since $\mu_r \approx 1$ for organic polymers at frequencies in the visible part of the electromagnetic spectrum, the equation may be further simplified to $$n \approx \sqrt{\varepsilon_r}$$

This means that the refractive index of a polymer/copolymer is changed when its relative permittivity $\varepsilon_r$ is varied. To understand how relative permittivity and thereby the refractive index of a polymer/copolymer can be modified, one has to take a closer look on what happens when light waves interact with matter. If an electric field, in this case the electric component of a light wave, $\vec{E}$, acts on a medium it induces a dipole moment $\vec{p}$. Polarity $\vec{P}$ is defined as electric dipole density per unit volume.

$$\vec{P} = \frac{d\vec{p}}{dV}$$

The norm of the vector $\vec{P}$ is the area density $\sigma_p$ of the polarity charge.

$$|\vec{P}| = \sigma_p$$

The polarity vector $\vec{P}$ and the outside electric field vector $\vec{E}$ point in the same direction. The lines of electric flux of the electric field induced by the polarity charges $\overrightarrow{E_{pol}}$ run from the positive to the negative surface charges of the dielectric. Hence, the electric flux lines inside the dielectric run into the opposite direction as those of the exterior electric field $\vec{E}$. The polarity $\vec{P}$ within the electric field is given by $$\vec{P} = (\varepsilon_r - 1)\varepsilon_0 \vec{E} = \chi_e \varepsilon_0 \vec{E}$$

The electric susceptibility was defined earlier. Two types of polarity need to be distinguished: displacement polarity and orientational polarity. Displacement polarity is caused by the displacement of electric charges in neutral atoms or molecules relative to each other. It is the relative tendency of a charge distribution, like the electron cloud of an atom or molecule, to be distorted from its normal shape by an external electric field, i.e. the electric field induces electric dipole moments. Orientational polarity is caused by orienting permanent dipoles along the electric field lines. Those dipoles have been present in the medium even before the electric field was applied. In the visible spectral range, only orientational polarity of the electron shall be taken into account. The frequencies of visible light are relatively high in the range of about $10^{14}$ Hz to $10^{15}$ Hz. Therefore, factors contributing to the overall polarity caused by displacement of the atoms and orientation of permanent dipoles are so small that they can be neglected. Only the electrons are able to "follow" the quickly oscillating electric field. For the displacement polarity the equation $$\vec{P} = x\alpha\vec{E}$$

provides a relation between the number of particles per unit volume x and the polarity. The constant of proportionality $\alpha$ in this equation is called electric polarizability. Polarizability is a molecular parameter. Quantum particles are not rigidly connected to each other, they are rather bound to their resting position by forces that are, to a first approximation, elastic. Therefore, Newton's law F=−k x can be applied. An external electric field $\vec{E}$ exerts a force Q·E upon such a charge Q. This force deflects the charge by a distance x=F/k=Q E/k. This displacement causes an induced dipole moment $$\vec{p} = Qx = \frac{Q^2}{k}\vec{E} = \alpha\vec{E}$$

By comparison it can easily be seen that $\alpha$ must be proportional to $\varepsilon_r$.

$$\alpha \propto (\varepsilon_r - 1)\varepsilon_0$$

This means that altering the polarizability of molecules comprising a given medium causes a change in refractive index of that medium.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

No doubt many other effective alternatives will occur to the skilled person. It will be understood that the invention is not limited to the described embodiments and encompasses modifications apparent to those skilled in the art and lying within the scope of the claims appended hereto.

EXAMPLES

The invention is illustrated in detail by the examples which follow, without any intention of restricting it thereby.

The following examples are also encompassed by the present disclosure and may fully or partly be incorporated into embodiments and the general disclosure of the invention.

The manipulation of the UV/Vis spectrum in the single-photon experiment is performed by putting the cuvette containing the dissolved sample on the sample holder followed by irradiation of the cuvette. The changes in the UV/Vis spectrum are monitored over time by UV/Vis measurements e.g. by using a UV/Vis spectrometer Lambda 900 (by Perkin Elmer).

The manipulation of the refractive index in the single-photon experiments as described below is performed by putting the sample on the sample holder and irradiation of the sample preferably for 30 seconds. The resulting refractive index change is monitored over time by refractive index measurements. The change of refractive index is measured with a multi-wavelength refractometer (ATR-L from Schmidt&Haensch).

The single-photon experiments show the ability of the described polymeric optical materials for the artificial lens to be used in the process according to the invention to locally change the initial polarizability through irradiation with the specific first and second wavelengths to initiate e.g. [2π+2π] cycloaddition or cycloreversion as described before or below.

Alternatively, the artificial lens may be treated based on a multi-photon (for example two-photon) process as described further below in examples 14 to 19.

EXAMPLES

Example 1: Preparation of Poly(M-14)

1 g of M-14 is first dissolved in 10 mL chloroform. The solution is then degassed and 1.33 mg AIBN is added. The mixture is then stirred at 60° C. for 14 h. The polymer is subsequently precipitated in 250 mL methanol. The yielded polymer poly(M-14) is then dried.

Example 2

In a second example, a solution of 75.4 mg of poly(M-14) in 10 mL THF is prepared. It is diluted by a factor of 500. The diluted solution is filled in a quartz-glass cuvette (32/GL14/S/Q/10by STARNA with a path length of 10 mm). A UV/Vis-spectrum is taken by using a UV/Vis spectrometer Lambda 900 (by Perkin Elmer). The sample is alternatingly irradiated at 340 nm and a UV/Vis-spectrum is taken. The result is depicted in FIG. 12 showing absorption as a function of wavelength for said single-photon process.

There are three isosbestic points in FIG. 12. This indicates a controlled conversion. The shown photochemical reaction of said conversion is a [2π+2π] cycloaddition, as shown in FIG. 8 resulting in a crosslinked polymer. The dimerization of the photoactive unit is indicated by the declining signal at 332 nm. The signal intensity in the range from 260 nm to 275 nm is increasing.

The reaction mixture is dried and analyzed by NMR.

$^1$H NMR (500 MHz, $CDCl_3$) δ 7.45, 7.17, 7.08-7.03, 7.01-6.96, 6.84, 6.75, 6.61, 6.52, 4.96, 4.72, 4.06, 3.95-3.87, 2.58, 2.54-2.47, 2.36, 1.76, 1.71-1.56, 1.49-1.44, 1.37-1.24, 1.14, 0.93-0.84.

The singlets at 4.72 and 4.96 ppm in said $^1$H NMR spectrum are assigned to the cyclobutane ring formed via said photochemical [2π+2π] cycloaddition reaction. The two signals are attributed to the formation of a mixture of photodimers composed of the syn and anti, respectively head-to-head and head-to-tail arrangements. The NMR signals and conclusions are in agreement with the literature [Rao et al., Chem. Ber., 1973, 106 (2), 388].

Example 3

In a third example, the irradiated poly(M-14) as prepared according to example 2 is used. A UV/Vis-spectrum is taken. The sample is irradiated at 275 nm and UV/Vis-spectra are taken alternatingly. The result is depicted in FIG. 13 showing absorption as a function of wavelength for said single-photon process.

Said experiment shows the ability of the representative polymeric optical material to cleave dimerized photoactive units.

The amount of the cyclobutane moiety within crosslinked poly(M-14) decreases. The mechanism for said cleavage is shown in FIG. 9. The back-conversion is indicated by the increasing signal at 332 nm.

The reaction mixture is dried and analyzed by NMR.

$^1$H NMR (500 MHz, $CDCl_3$) δ 7.67, 7.40, 7.20-7.14, 6.86, 4.11-4.00, 2.69-2.62, 2.36, 1.87-1.78, 1.65, 1.53-1.41, 1.40-1.26, 1.14, 0.91.

As can be seen further, the singlets at 4.74 and 4.98 ppm as evidenced in the $^1$H NMR spectrum of example 2, previously assigned to the cyclobutane ring formed via photo induced photochemical [2π+2π] cycloaddition reaction in are disappeared documenting the cleavage as shown in FIG. 9.

Example 4

In a fourth example, a polymeric optical material having a copolymeric matrix is prepared.

A molten mixture of 2.00 g M-14, 10.36 mg 2-[3-(2H-benzotriazol-2-yl)-4-hydroxyphenyl]ethyl methacrylate, 220.00 mg poly(ethylene glycol) diacrylate (average Mn 250), 247.60 mg n-butyl methacrylate is first degassed. Subsequently, 25.57 mg 1,1'-(3,3,5-trimethylcyclo-hexylidene)bis[2-(1,1-dimethylethyl)peroxide is added. The mixture is filtered into a sheet-mold of 1 mm thickness. Polymerization occurs thermally at conditions a person who is skilled in the art would consider as appropriate. After the polymerization process is finished, the polymer is demolded and a polymer-sheet of 1 mm thickness is yielded.

Example 5

In a fifth example, a cylindrical blank of the polymeric optical material as prepared according to example 4 is punched out of the sheet. A multi-wavelength refractometer with a heating stage is used for determination of the refractive index. Before the measurement, the blank is heated in the device to 80° C. to release stress from the material. Measurement of refractive index occurs, in this example, at 546 nm and 35° C. The blank is irradiated at 340 nm in an apparatus as shown in FIG. 10 outside the refractometer. The sample is transferred back to the refractometer, heated up to 80° C. and the refractive index is measured at 546 nm and 35° C.

FIG. 14 shows the change of refractive index for said single-photon process as a function of applied energy.

With increasing energy application, the refractive index of the irradiated polymeric optical material decreases. This is caused by the crosslinking reaction shown in FIG. 8. The cycloaddition reaction as shown in FIG. 8 yields a less polarizable photoactive unit (cyclobutane ring), which leads to a decrease of refractive index.

The sample irradiated at 340 nm is further used in the procedure as described herein but with an irradiation wavelength of 275 nm.

The effect shown in FIG. 15 is caused by cleavage or back conversion of the cyclobutane moieties (see FIG. 9). This leads to a higher polarizability and increases refractive index. FIG. 15 shows the change of refractive index for said single-photon process as a function of applied energy.

FIG. 10 shows the system (400) relating to the irradiation setup as described before using an LED system for a single-photon experiment. The system (400) comprises the irradiation source (402), a beam collimator (404) and a sample holder (408) on which the sample (406) is mounted. The irradiation source (402) is in this example 5 Mounted LED M340L4—340 nm, 53 mW by Thorlabs.

Examples 6 to 10 are analogously performed to Examples 1 to 5 as outlined above.

Example 6: Preparation of Poly(M-18)

1 g of M-18 is dissolved in 10 mL chloroform. The solution is degassed and 1.33 mg AIBN is added. The mixture is stirred at 60° C. for 14 h. The polymer is precipitated in 250 mL methanol. The yielded polymer poly(M-18) is dried.

Example 7

In the seventh example, a solution of 12.67 mg poly(M-18) in 25 mL THF is prepared. It is diluted by a factor of 20. The diluted solution is filled in a quartz-glass cuvette. A UV/Vis-spectrum is taken. The sample is alternatingly irradiated at 340 nm and a UV/Vis-spectrum is taken. The result is shown in FIG. 16. FIG. 16 shows absorption as a function of wavelength for said single-photon process.

Example 8

In the eighth example, the irradiated sample of poly(M-18) according to example 7 is used. A UV/Vis-spectrum is taken. The sample is further irradiated at 275 nm and UV/Vis-spectra are taken alternatingly. The result is shown in FIG. 17. FIG. 17 shows absorption as a function of wavelength for said single-photon process.

Example 9

In a ninth example, a second polymeric optical material having a copolymeric matrix is prepared.

A molten mixture of 2.00 g M-18, 9.08 mg 2-[3-(2H-Benzotriazol-2-yl)-4-hydroxyphenyl]ethyl methacrylate, 65.8 mg ethylene glycol diacrylate, 211.7 mg 2-hydroxyethyl methacrylate and 173.92 mg 2-methacrylic acid octadecyl ester is degassed. Subsequently, 26.42 mg 1,1'-(3,3,5-trimethylcyclo-hexylidene)bis[2-(1,1-dimethylethyl) peroxide are added. The mixture is filtered in a sheet-mold of 1 mm thickness. Polymerization occurs thermally at conditions a person who is skilled in the art would consider as appropriate. After the polymerization process is finished, the polymer is unmolded, and a polymer-sheet of 1 mm thickness is yielded.

Example 10

In a tenth example, a cylindric blank of the ophthalmic material as prepared according to example 9 is punched out of the sheet. A multi-wavelength refractometer with a heating stage is used for determination of the refractive index. Before measurement, the sample is heated in the device to 80° C. to release stress from the material. Measurement of refractive index occurs at 546 nm and 35° C. Alternatingly the sample is irradiated at 340 nm, the sample is transferred back to the refractometer, heated up to 80° C. and the refractive index is measured at 546 nm and 35° C. The result is shown in FIG. 18. Therefore, FIG. 18 shows the change of refractive index for said single-photon process as a function of applied energy.

The sample irradiated at 340 nm is further used in the procedure as described herein but with an irradiation wavelength of 275 nm. The effect shown in FIG. 19 is caused by cleavage or back conversion of the cyclobutane moieties (see FIG. 9). FIG. 19 shows the change of refractive index for said single-photon process as a function of applied energy.

Examples 11 to 13

The following Examples 11 to 13 show the refractive index change upon irradiation in single-photon processes of polymeric optical materials having a copolymeric matrix comprising the polymerized monomers M-58, M-56 or M-15 in amounts as indicated in the following table and based on the formulation as described in Example 9:

| Example | Monomer (wt.-%) | n(546 nm; 35° C.) before | n(546 nm; 35° C.) after | Δn | Irradiation wavelength |
|---|---|---|---|---|---|
| 11 | M-58 (77) | 1.551 | 1.532 | 0.019 | 313 nm |
| 12 | M-56 (42) | 1.521 | 1.498 | 0.023 | 300 nm |
| 13 | M-15 (47) | 1.545 | 1.527 | 0.018 | 340 nm |

Examples for Irradiation with Two-Photon/Multi-Photon Absorption

Example 14

The experimental device used within example 14 is shown in FIG. 11. The system (410) for the two-photon experiment in FIG. 11 incorporates a tunable laser (412) (Ti:Sapphire laser (Chameleon Ultra II by Coherent, Santa Clara, CA, USA) as irradiation source that is configured to generate pulsed laser radiation. The irradiation beam is expanded in a beam shaper (414).

The pulsed laser radiation generated by the laser source (412) is then transmitted to a microscope objective (416) (LUCPLFLN by Olympus) to produce a focused laser radiation output.

The region of the polymeric optical material (sample 418) in which the refractive index is to be changed is targeted via a voice coil driven linear stage (422) (by PIMag®), which is used to position the sample holder (420).

The polymer samples (418) herein are flat buttons with diameters of 6.0 mm of the polymeric optical material described in the following. All polymers of said polymer samples are co-polymers containing at least a crosslinker. The main monomer used for the manufacture of the polymeric optical material comprising a co-polymeric matrix is summarized in the following table for each button material:

| Main Monomer | |
| --- | --- |
| 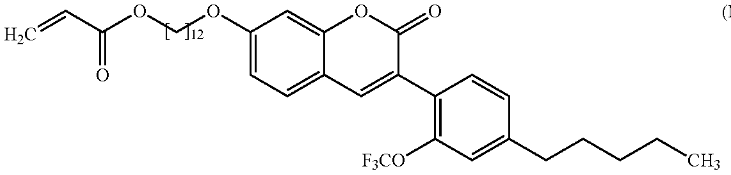 | (M-14) |
| 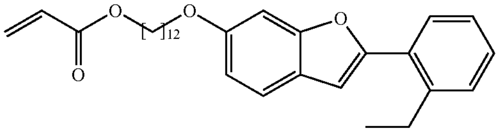 | (M-58) |
| 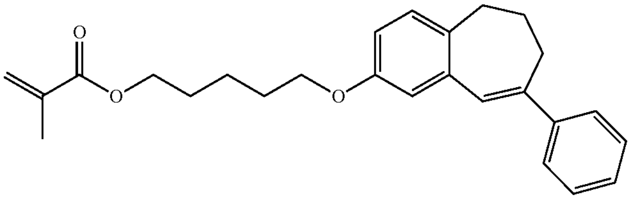 [SMILES: C=C(C)C(=O)OCCCCCOc1ccc2c(c1)C=C(c1ccccc1)CCC2] | (M-56) |
| 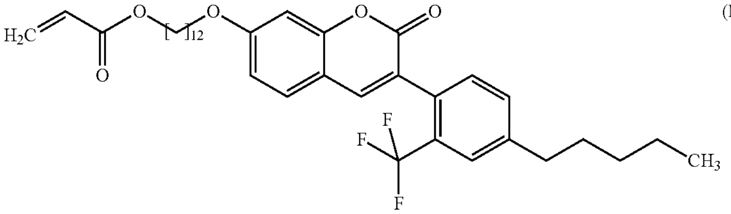 | (M-18) |
| 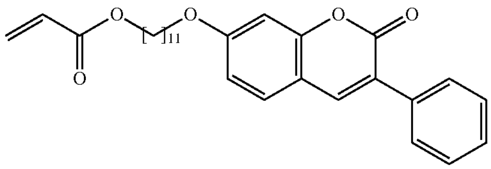 | (M-15) |

During the irradiation process, said flat buttons of polymer material as described before as polymer samples (418) are placed in a fixed position inside the sample holder (420). A coupling gel (Vidisic [Bausch& Lomb]) is applied on the button. The sample holder (420) is mounted horizontally and laser pulses are focused to said material using a high-numerical-aperture microscope objective. The refractive index shaping is created approximately nearby the surface. This mimics a "bottom-up" and "spot-to-spot" procedure.

The sample holder (420) is driven by a voice coil linear stage (422) as described before. This mimics the scanner movement.

Typical laser parameters are 680 nm wavelength, 180 fs pulse duration and an average power of 500 mW. The parameters that are varied are the scan speed and the x-spacing between the lines of a layer. The 3 parameters are adjusted to create a homogeneous solid refractive index shaping. The change of refractive index is measured with a multi-wavelength refractometer (ATR-L from Schmidt&Haensch).

The results of the two-photon laser experiments correlate with the refractive index diagram electromagnetic energy input-dependent refractive index of the one-photon experiments.

Example 15

In a fifteenth example, a solution of 288 mg poly(M-14) (example 1) in 4 mL acetonitrile is prepared. The solution is filled in a quartz-glass cuvette (32/GL14/S/Q/10by STARNA with a path length of 10 mm). The cuvette with the liquid solution of poly(M-14) is irradiated at a wavelength of 680 nm with 1 μJ pulses at 100 kHz repetition rate using an NA 0.1 microscope objective. The two-photon generated fluorescence of the solution is measured as a function of irradiation time using a pulsed irradiation source as described earlier. The fluorescence is measured at a 90-degree geometry to the irradiation beam using a fiber-coupled and diffraction grating-based spectrometer with a sensitivity from 350 to 1050 nm. The fluorescence spectra with increasing irradiation time are compiled in FIG. 20. The two-photon induced [2π+2π] cyclodimerization reaction of the photoactive units is indicated by the declining signals between 400 and 500 nm. The emission peak decreases due to the conversion to non-fluorescent dimers in poly(M-14).

The reaction mixture is dried and analyzed by NMR in d-chloroform. The singlets at 4.74 and 4.98 ppm are assigned to the cyclobutane ring formed via said two-photon induced photochemical [2π+2π] cycloaddition reaction. The NMR spectrum correlates with the NMR spectrum from example 2. Both, the single-photon and two-photon induced photochemical [2π+2π] cycloaddition reaction yield the same products.

Example 16

In a sixteenth example, the irradiated poly(M-14) as prepared according to example 14 is used as acetonitrile solution (4 mL) in a quartz-glass cuvette (32/GL14/S/Q/10by STARNA with a path length of 10 mm). The solution is irradiated at a wavelength of 532 nm with 1 μJ pulses at 100 kHz repetition rate using an NA 0.1 microscope objective. The amount of the cyclobutane moieties within the substrate decreases over time during laser irradiation attributed to two-photon induced photochemical [2π+2π] cycloreversion reaction.

The reaction mixture is dried and analyzed by NMR in d-chloroform. The singlets at 4.74 and 4.98 ppm, previously assigned to the cyclobutane ring formed via two-photon induced photochemical [2π+2π] cycloaddition reaction in experiment 14 disappear. The results of the two-photon induced photochemical [2π+2π] cycloreversion correlate with the single-photon induced photochemical [2π+2π] cycloreversion experiment from example 3.

Example 17

In a seventeenth example, a solution of 288 mg poly(M-14) from example 1 in 4 mL acetonitrile is prepared. The solution is filled in a quartz-glass cuvette (32/GL14/S/Q/10by STARNA with a path length of 10 mm). In this example, the two-photon generated fluorescence from the solution is measured as a function of irradiation wavelength using a pulsed irradiation source as described earlier. The cuvette with the liquid solution of poly(M-14) is irradiated with 1 μJ pulses at 100 kHz repetition rate using an NA 0.1 microscope objective. The fluorescence is measured at a 90-degree geometry to the irradiation beam using a fiber-coupled and diffraction grating-based spectrometer with a sensitivity from 350 to 1050 nm. The peak of the fluorescence spectra at 420-430 nm is determined for each irradiation wavelength and then plotted in FIG. 21 as a function of irradiation wavelength. As can be seen in FIG. 21, the two-photon induced fluorescence has high values around 680 nm and declines with increasing irradiation wavelength. The excitation is maximizing at approximately two times the wavelength at which one-photon excitation would have maximized (340 nm). This observation is typical for two-photon absorption processes.

Example 18

In a eighteenth example, a polymeric optical material having a copolymeric matrix is prepared. A molten mixture of 4.1 g M-14, 21 mg 2-[3-(2H-benzotriazol-2-yl)-4-hydroxyphenyl]ethyl methacrylate, 143.6 mg 1,18-octadecanediol diacrylate, 506.7 mg 2-hydroxyethylmethacrylate, is first degassed. Subsequently, 52 mg 1,1'-(3,3,5-trimethylcyclo-hexylidene)bis[2-(1,1-dimethylethyl)peroxide is added. The mixture is filtered into a sheet-mold of 1 mm thickness. Polymerization occurs thermally at conditions known in the art. After the polymerization process is finished, the polymer is demolded and a polymer-sheet of 1 mm thickness is yielded. Cylindrical blanks of said optical material are punched out of the sheet.

Example 19

In the nineteenth example, cylindrical blanks of optical material as prepared according to example 18 are used. A two-photon induced photochemical crosslinking reaction of the optical materials is shown using two different irradiation sources as described above in a setup depicted in FIG. 11. One irradiation source, labeled in FIG. 22 with “kHz” is a femtosecond laser operating at 680 nm and emitting μJ-pulses with a repetition rate of 100 kHz. The second irradiation source, labeled in FIG. 22 with “MHz” is a femtosecond laser operating at 680 nm wavelength emitting nJ-pulses with a repetition rate of 80 MHz. The cylindrical blanks are treated at an average power of 400 mW. Subsequently to the irradiation treatment, for each measurement, the optical pathlength difference throughout the sample is measured with an optical-phase-sensitive camera. The refractive index of the material in the irradiated zone is deduced from said optical pathlength difference and the sample thickness. The refractive index change (Δn) depicted in FIG. 22 is obtained by comparing irradiated and non-irradiated zones.

Subsequent data points from low to high values of radiant exposure (=applied energy) receive increasing duration of irradiation, thus showing the cumulative effect of the irradiation treatment. This cumulative effect allows to translate physician’s requirements accurately to a corresponding treatment plan.

FIG. 22 also shows the difference in overall system efficiency between the kHz and MHz irradiation sources. With all system settings identical, the kHz-system exhibits a significantly increased writing speed and thus, results in shorter and more desirable treatment times. The results show that the two-photon induced photochemical [2π+2π] cyclodimerization reaction is more efficient for the kHz-system, which is in accordance with the conclusion drawn from excited state lifetimes described above.

Example 20

In this example, cylindrical blanks of optical material as prepared according to example 18 are used. A two-photon induced photochemical crosslinking reaction of the optical materials is shown using different irradiation wavelengths. The radiation source used is a femtosecond laser tunable between 666 and 722 nm and emitting μJ-pulses with a repetition rate of 100 kHz. A setup depicted in FIG. 11 is used. For each measurement, an area of 1 mm×6 mm on the optical material is treated at an average power of 400 mW with identical overall radiant exposure. The refractive index of the material in the irradiated zone is deduced from said optical pathlength difference and the sample thickness. The refractive index change (Δn) depicted in FIG. 23 is obtained by comparing irradiated and non-irradiated zones. The data presented in FIG. 23 demonstrates that the range of 680 to 720 nm can be used efficiently to create refractive-index modifications in the optical material.

FIG. 24 shows a selected example of a refractive-index profile written into the optical material in the course of this experiment. The irradiation source is in this example operated at 710 nm with 5-μJ pulses at a repetition rate of 100 kHz. Using an optical scanner, a rectangular area of 0.6 mm×6 mm on the optical material is irradiated with spatially overlapping optical pulses. The data is collected with a phase-sensitive camera system mounted to a microscope at 10× magnification. The phase-sensitive camera records the optical phase differences with a lateral resolution of 30 μm. The recorded values are subsequently converted to refractive-index changes by considering the sample thickness. FIG. 24 shows that the refractive index of the irradiated area is reduced by around 0.011 compared to the surrounding nonirradiated material.

INDEX OF FIGURES

Figure 1:
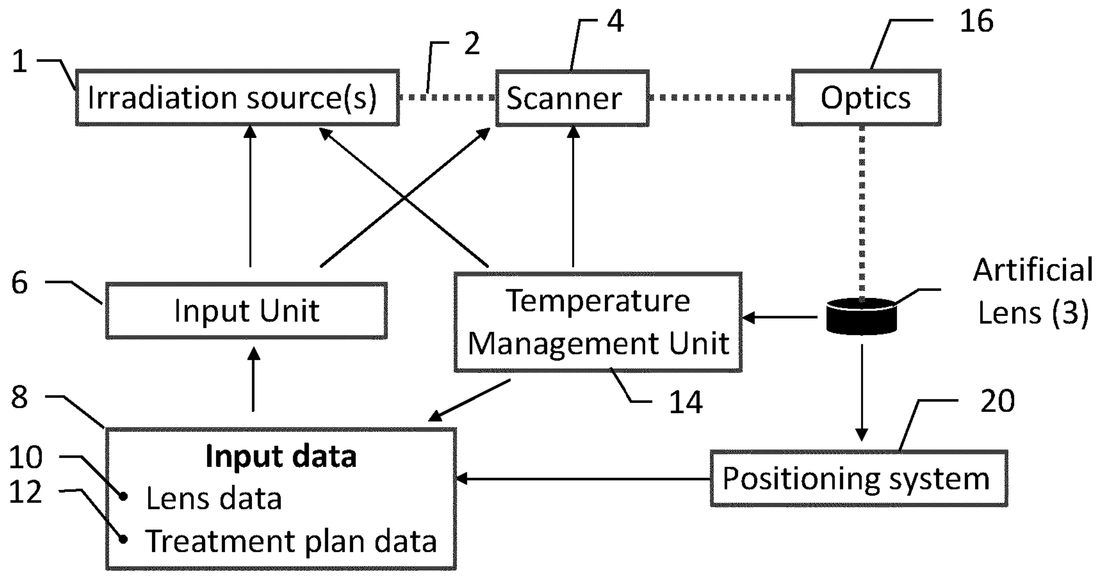
FIG. 1 is a schematic illustration of a system for the irradiation of an artificial lens, e.g. a contact lens or an intraocular lens not arranged within an eye of a patient.
Figure 2:
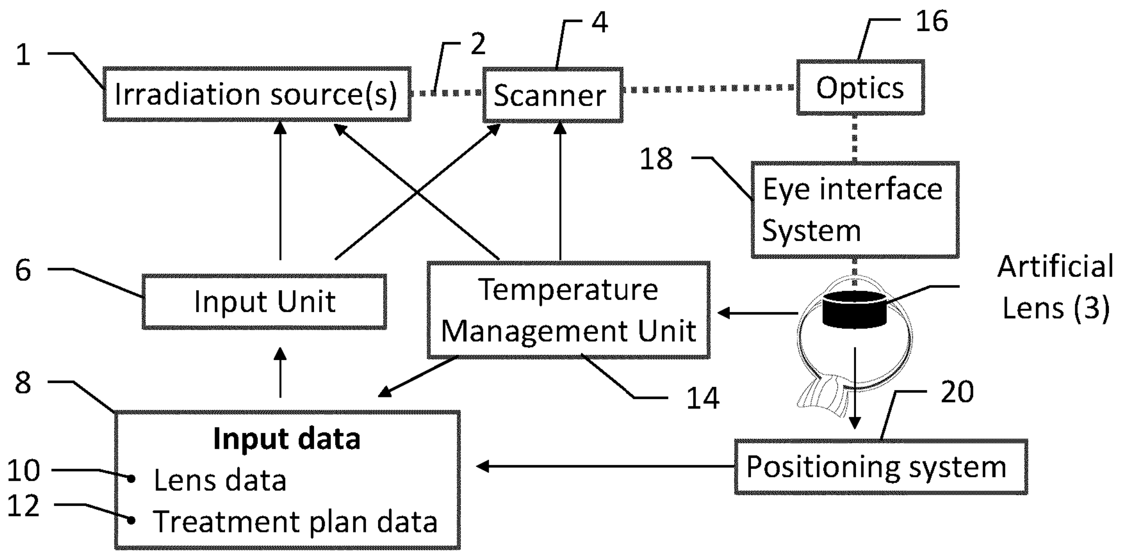
FIG. 2 is a schematic illustration of a system for the irradiation of an intraocular lens arranged within an eye of a patient.
Figure 3:
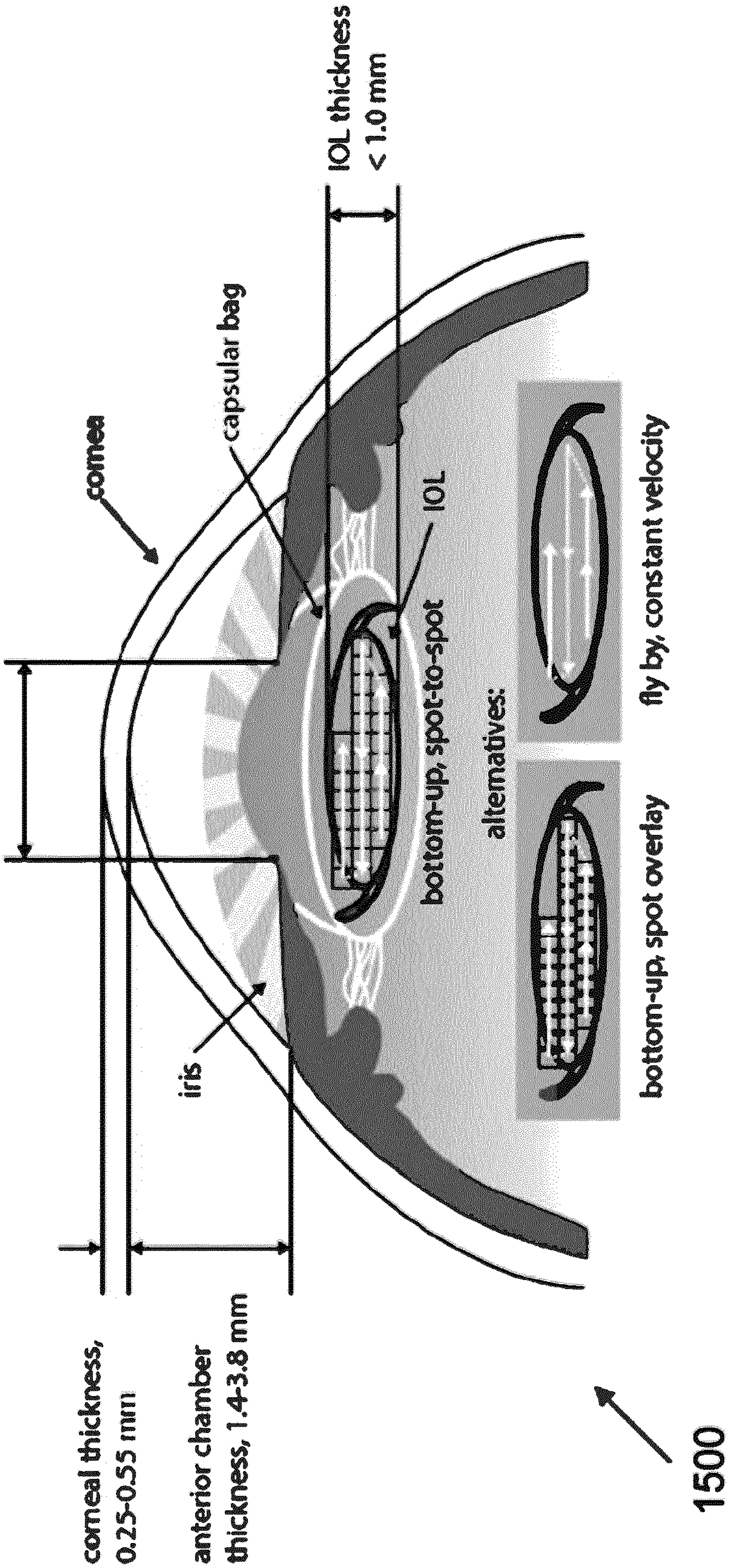
FIG. 3 shows a schematic illustration (1500) of scanning strategies.
Figure 4:
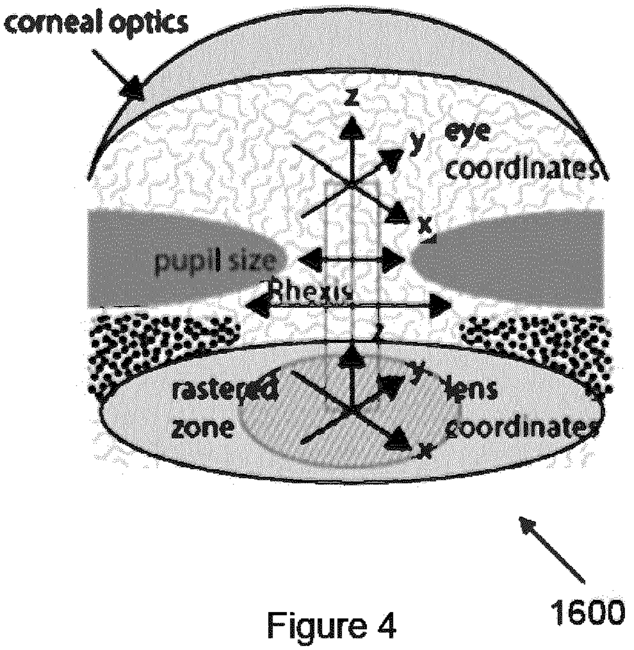
FIG. 4 shows a schematic illustration (1600) of said variables used in the scanning program taken into account when irradiating the lens within the eye of a patient.
Figure 5:
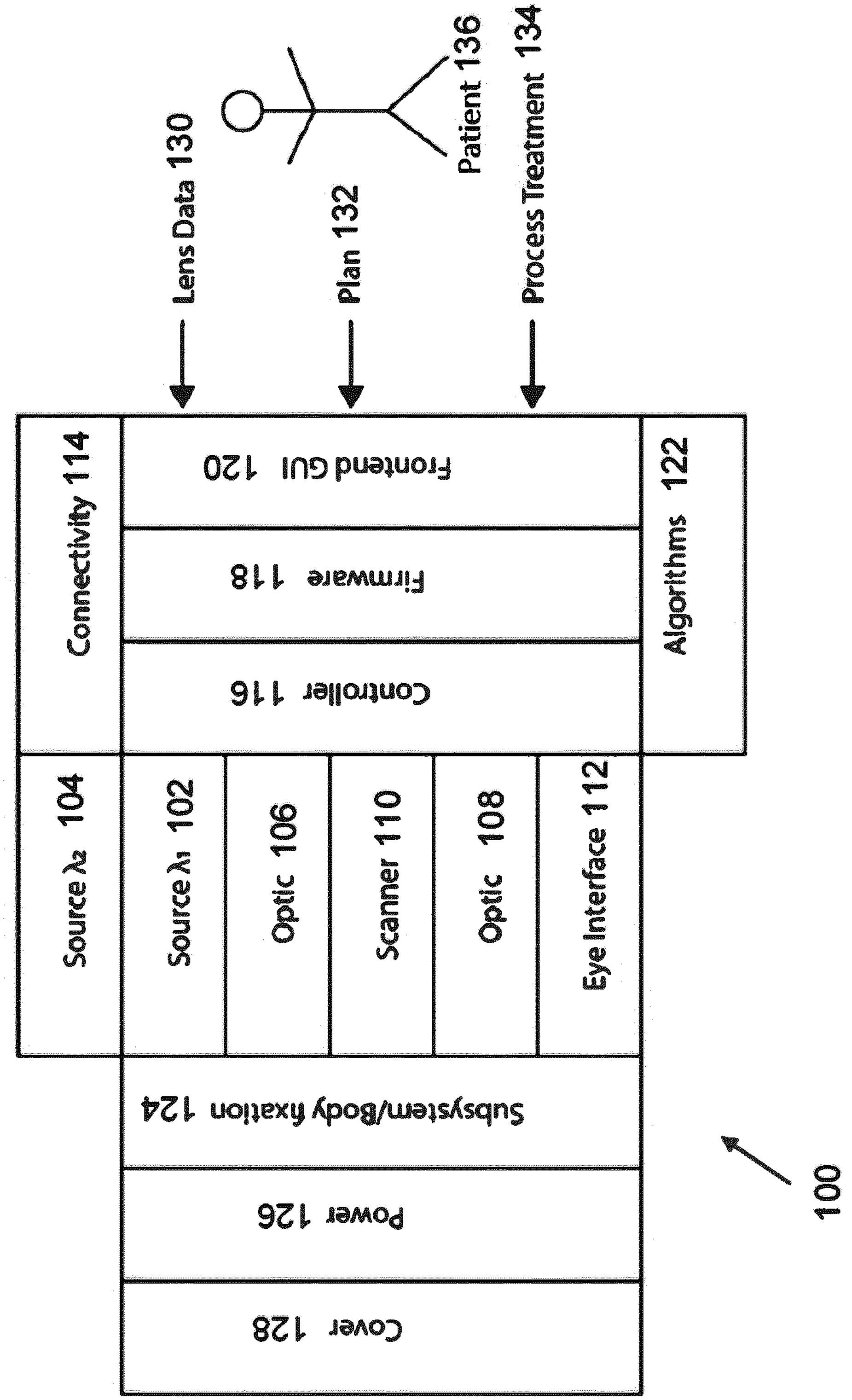
FIG. 5 shows a further schematic illustration of a system for the irradiation of an intraocular lens arranged within an eye of a patient.
Figure 6:
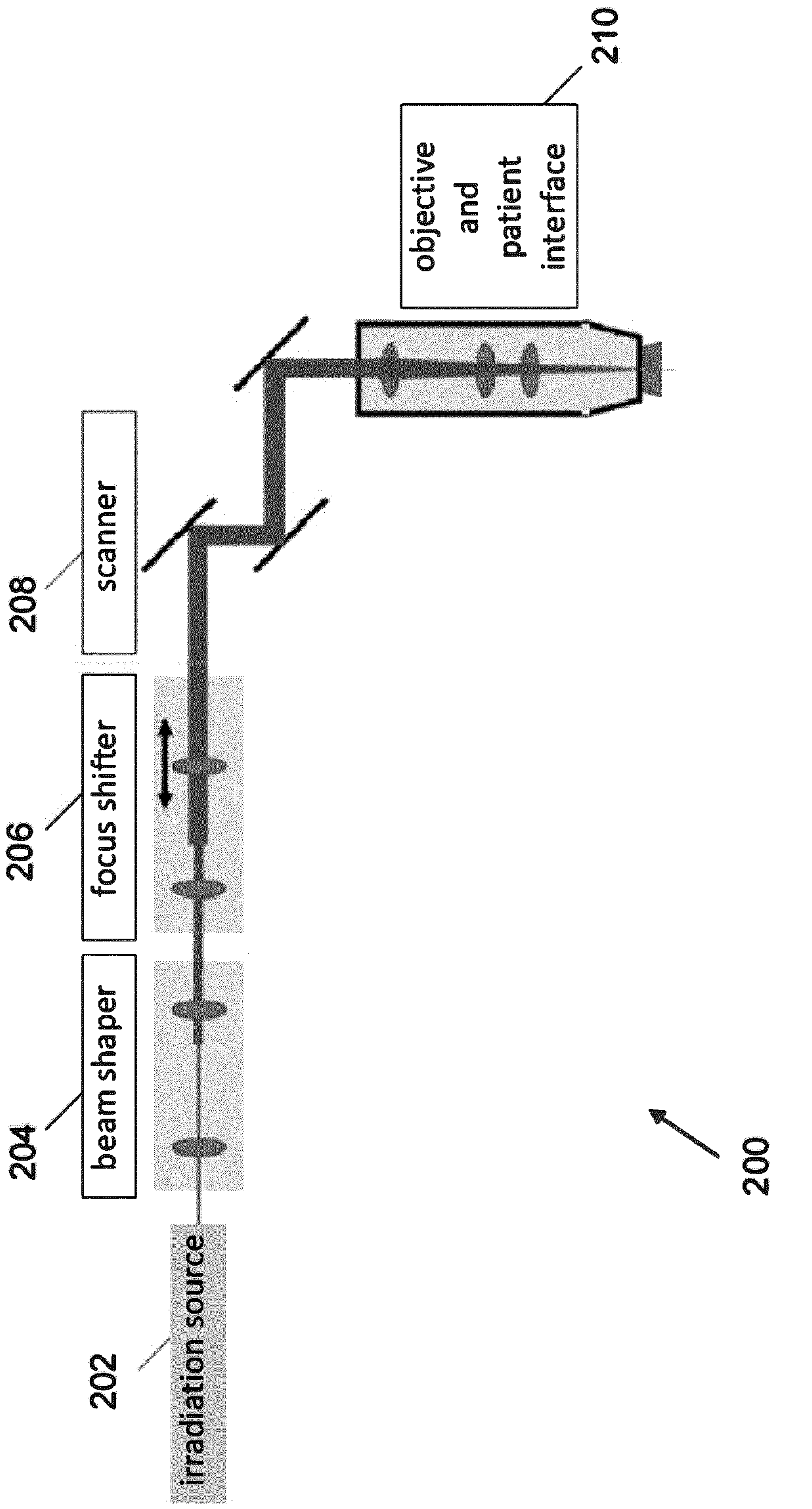
FIG. 6 shows a schematic illustration of components of the system for the irradiation of an intraocular lens arranged within an eye of a patient.
Figure 7:
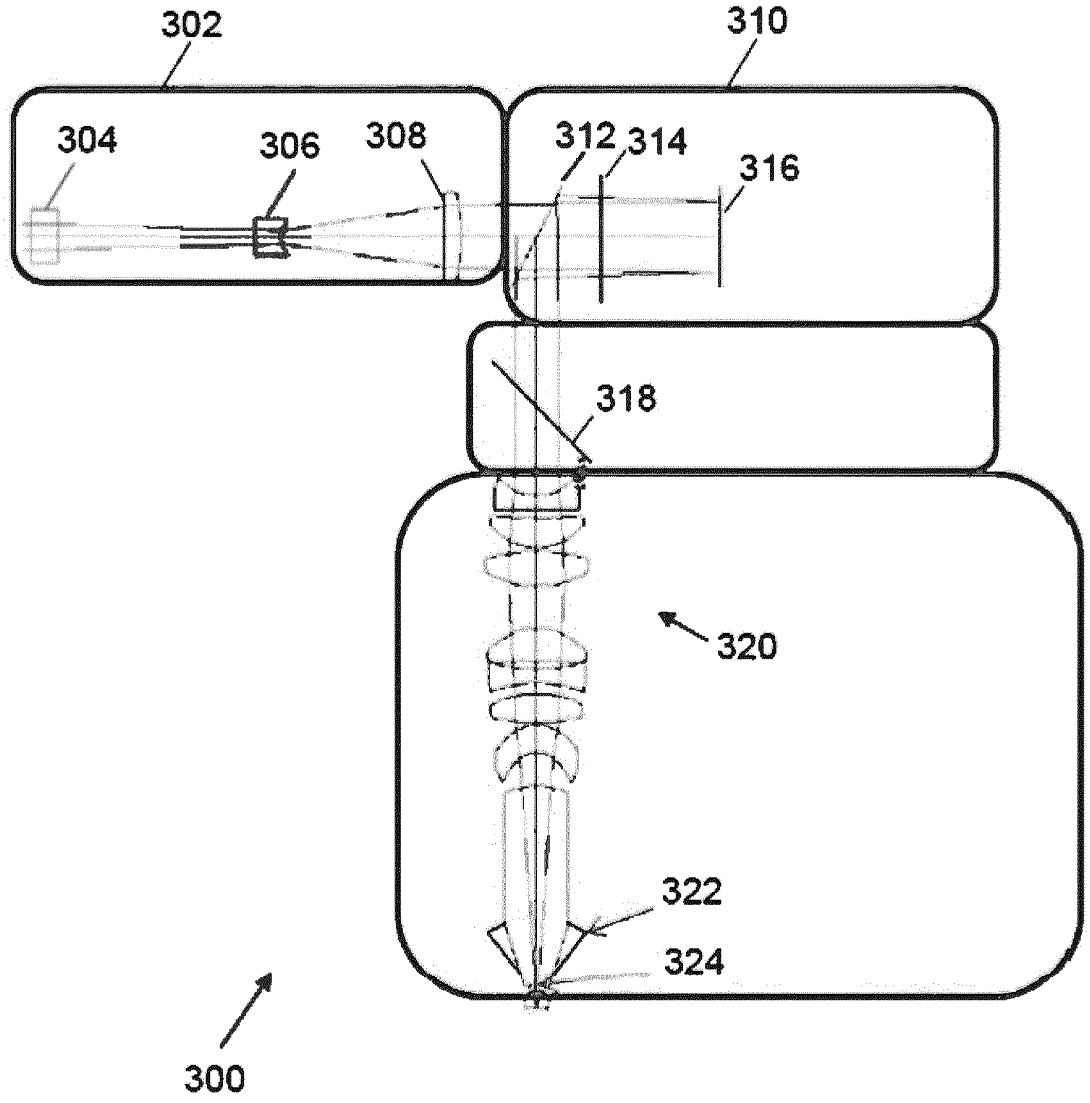
FIG. 7 shows a schematic illustration of components of the system for the irradiation of an intraocular lens arranged within an eye of a patient.
Figure 8:
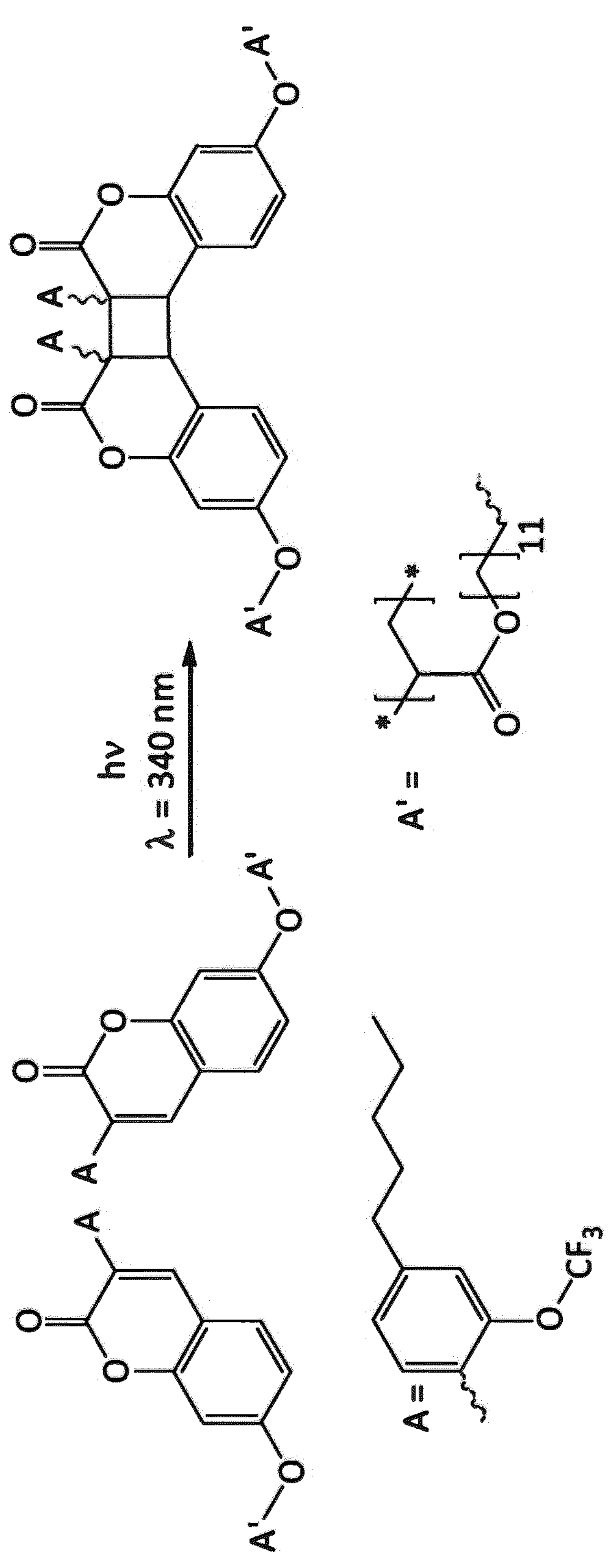
FIG. 8 shows a specific [2π+2π] cycloaddition reaction of poly(M-14).
Figure 9:
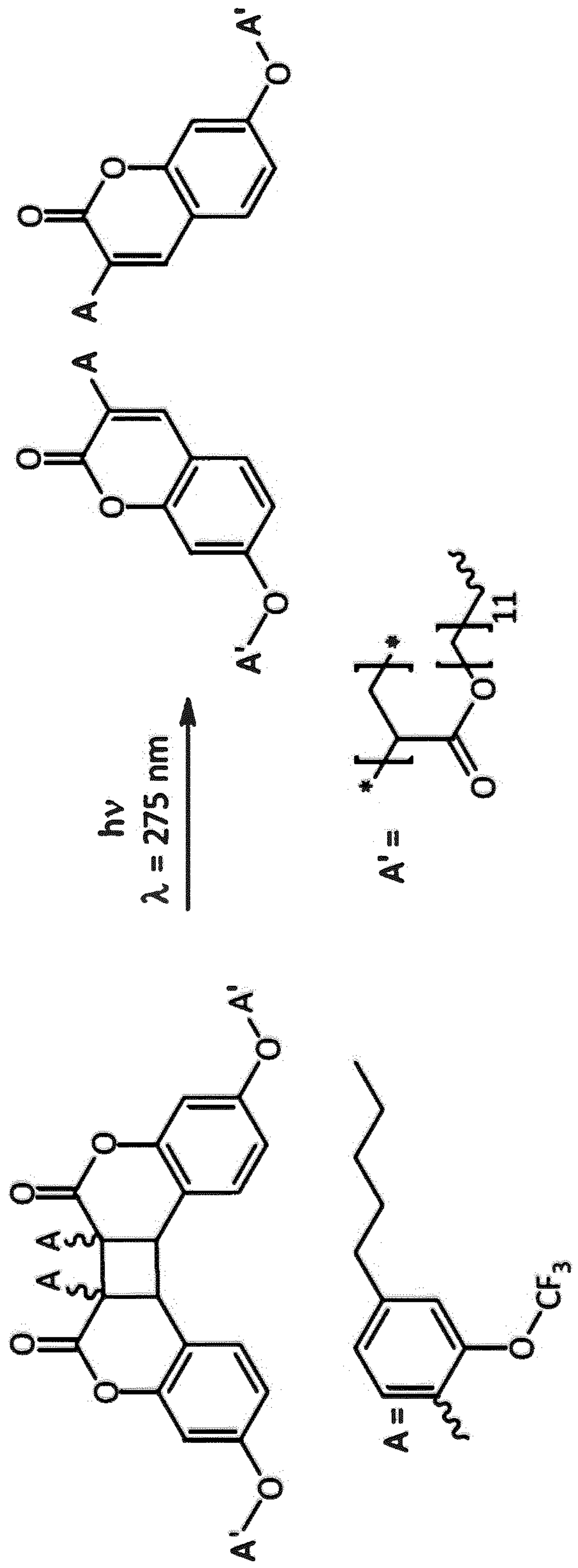
FIG. 9 shows a specific cleavage of poly(M-14)-dimer by cycloreversion.
Figure 10:
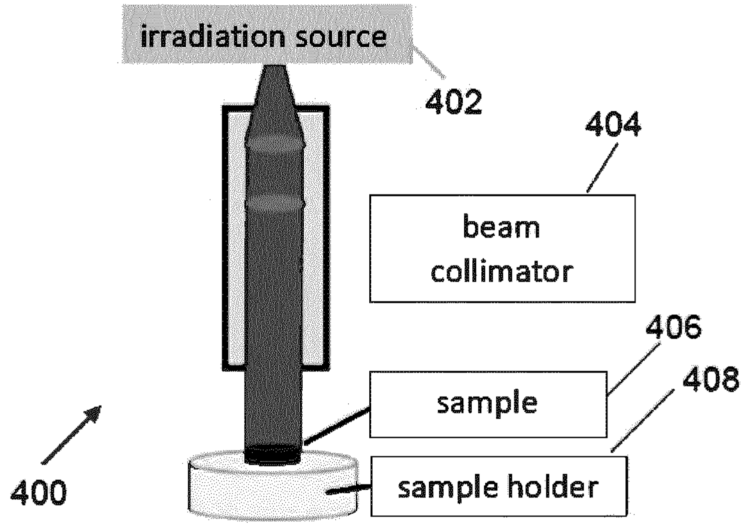
FIG. 10 shows the irradiation setup used in example 5.
Figure 11:
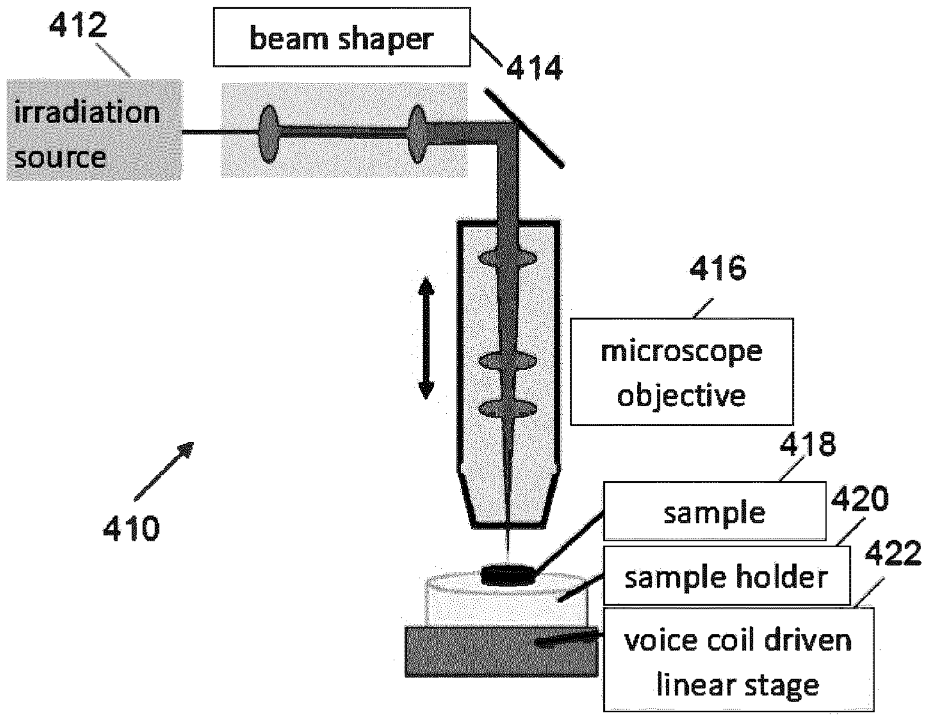
FIG. 11 shows an irradiation setup e.g. for example 14.
Figure 12:
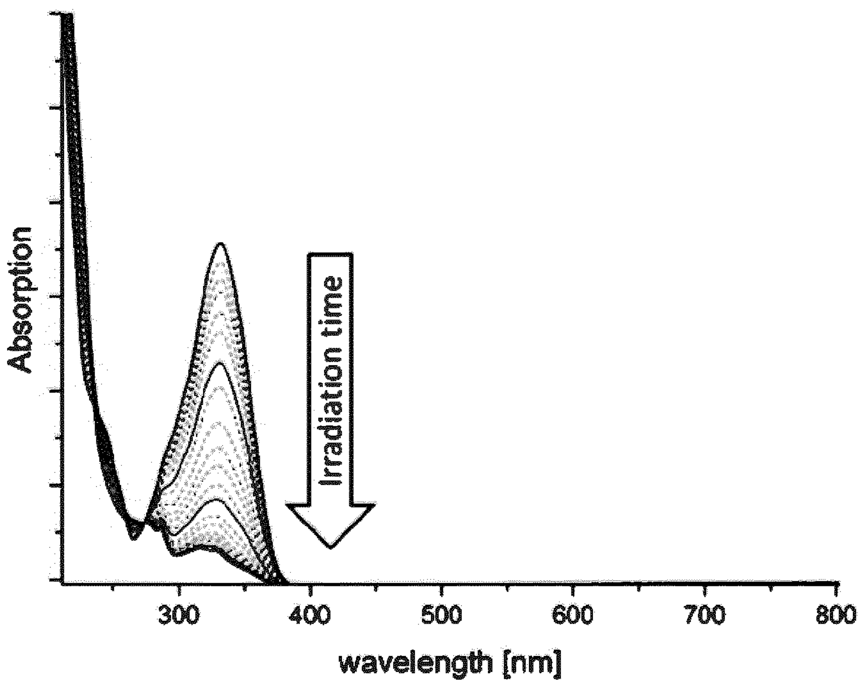
FIG. 12 shows absorption as a function of wavelength for a single-photon process as further described in the experimental section as example 2
Figure 13:
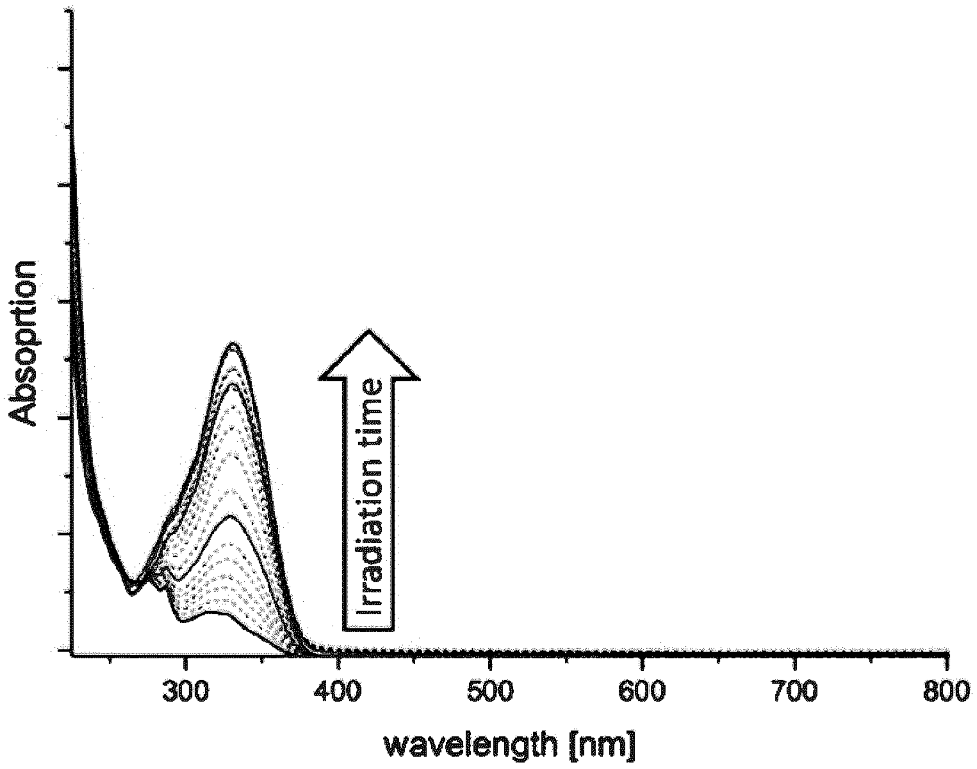
FIG. 13 shows absorption as a function of wavelength for a single-photon process as described in example 3.
Figure 14:
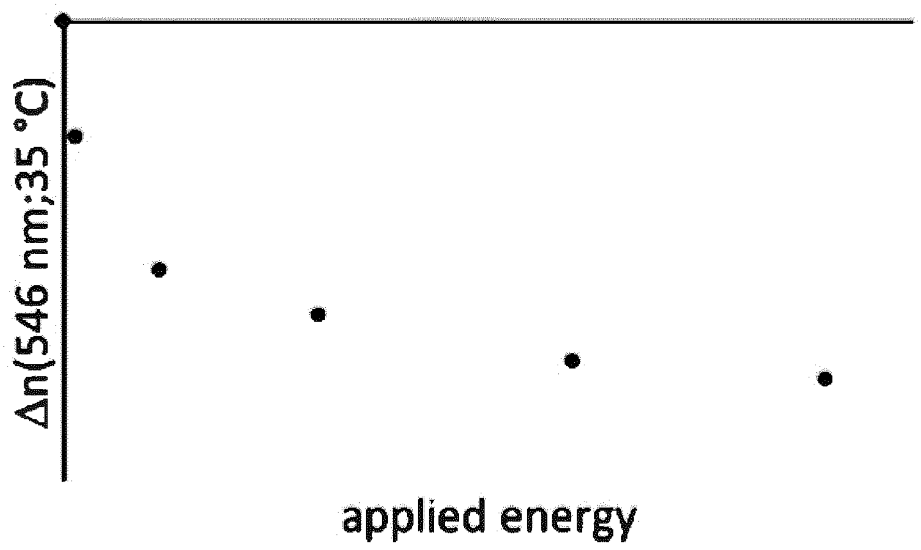
FIG. 14 shows change of refractive index for a single-photon process as a function of applied energy as described in example 5.
Figure 15:
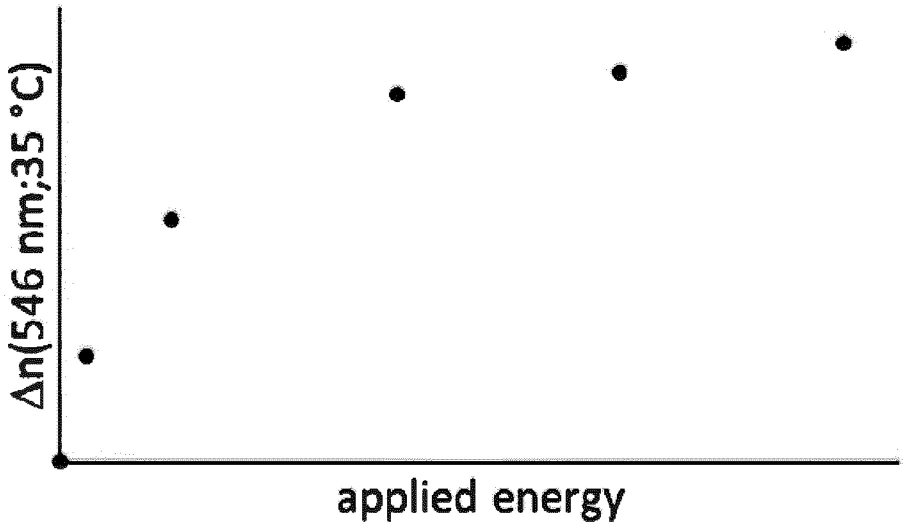
FIG. 15 shows change of refractive index for a single-photon process as a function of applied energy as described in example 5.
Figure 16:
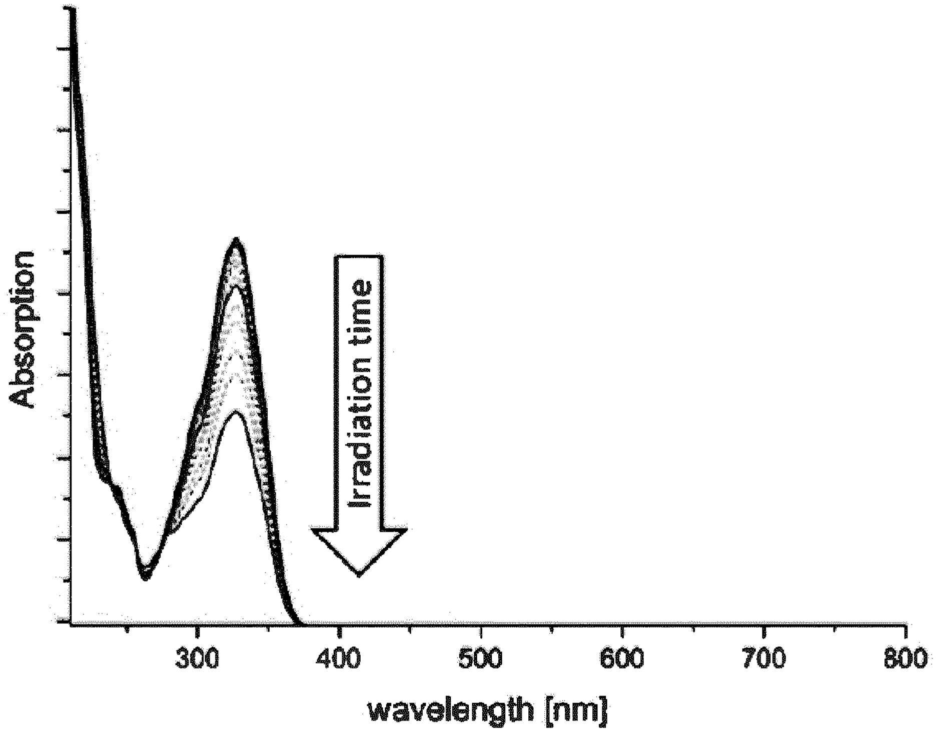
FIG. 16 shows absorption as a function of wavelength for a single-photon process as further described in example 7.
Figure 17:
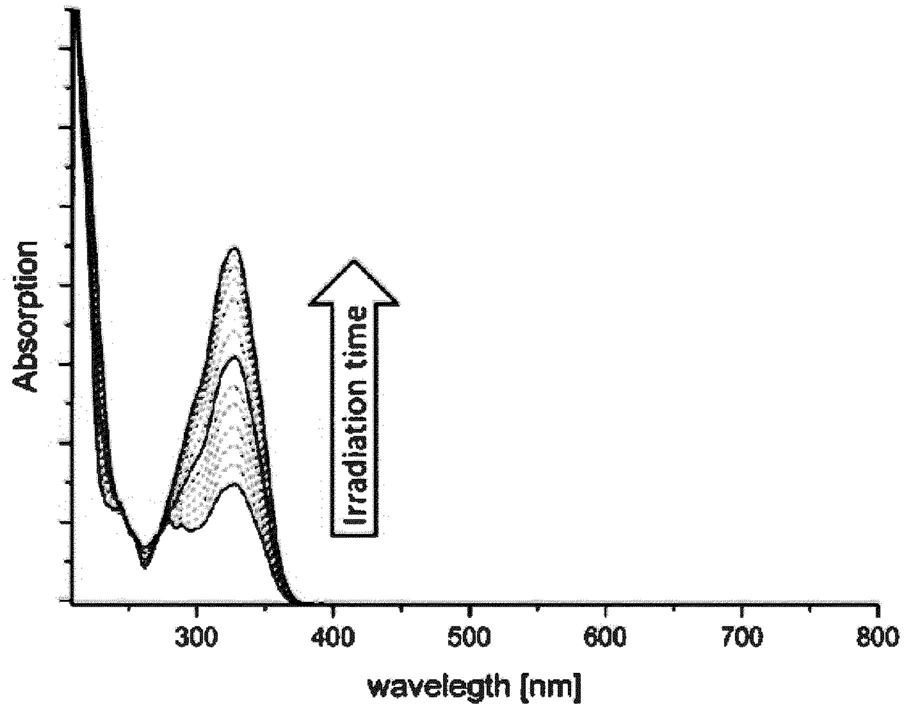
FIG. 17 shows absorption as a function of wavelength for a single-photon process as described in example 8 with a solution of example 7.
Figure 18:
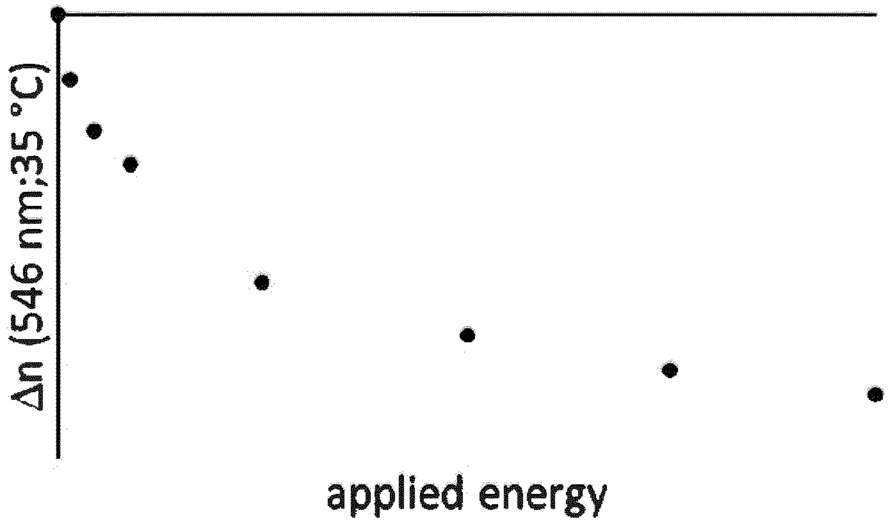
FIG. 18 shows change of refractive index for a single-photon process as a function of applied energy as described in example 10 for the bulk polymer of example 9 comprising polymerized M18.
Figure 19:
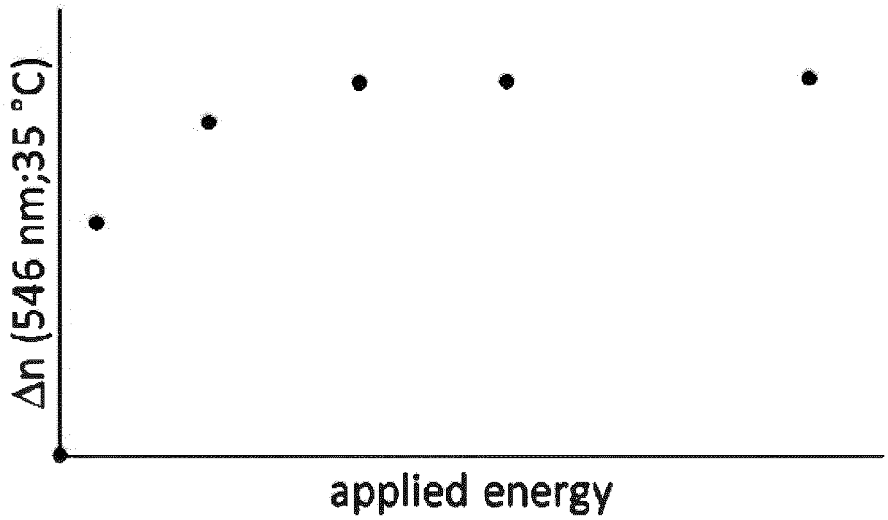
FIG. 19 shows change of refractive index for a single-photon process as a function of applied energy as described in example 10 for the crosslinked dimer of the bulk polymer of example 9 comprising polymerized M18.
Figure 20:
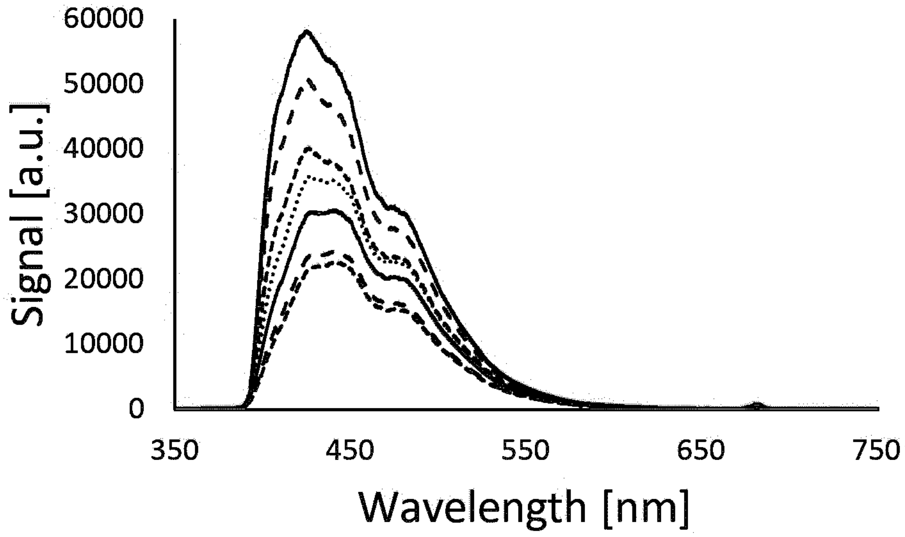
FIG. 20 shows the fluorescence spectra with increasing irradiation time according to example 15.
Figure 21:
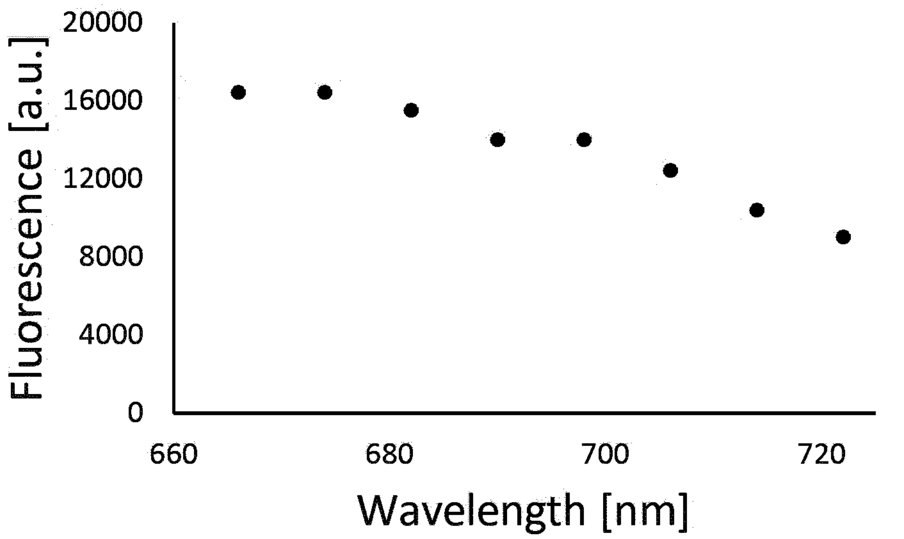
FIG. 21 shows the peak of the fluorescence spectra at 420-430 nm as a function of irradiation wavelength as described in example 17.
Figure 22:
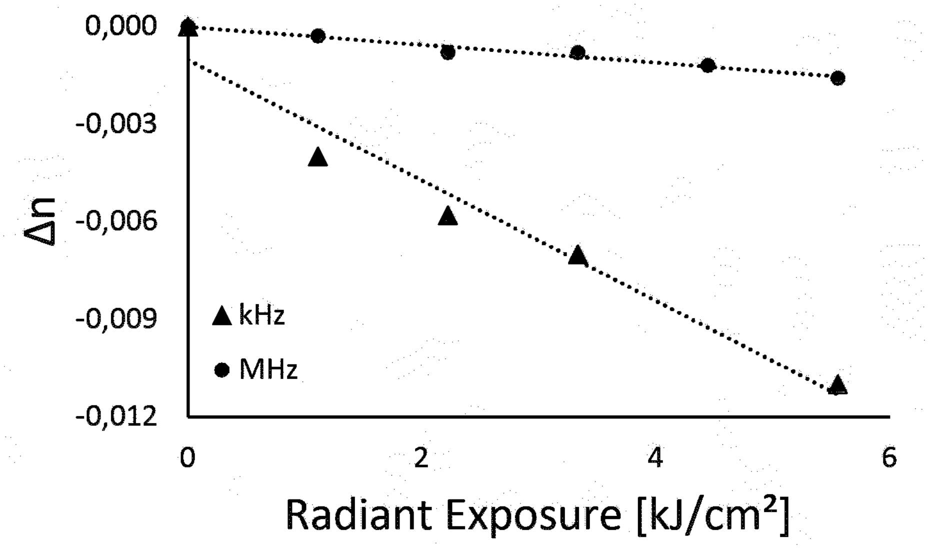
FIG. 22 shows the refractive index change (Δn) as a function of radiant exposure according to example 19.
Figure 23:
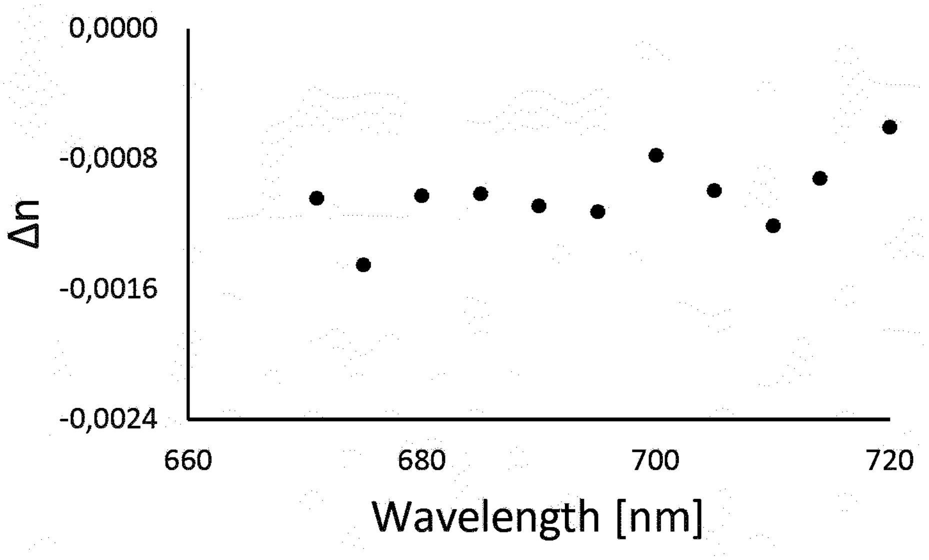
FIG. 23 shows the refractive index change (Δn) as a function of radiant exposure according to example 20.
Figure 24:
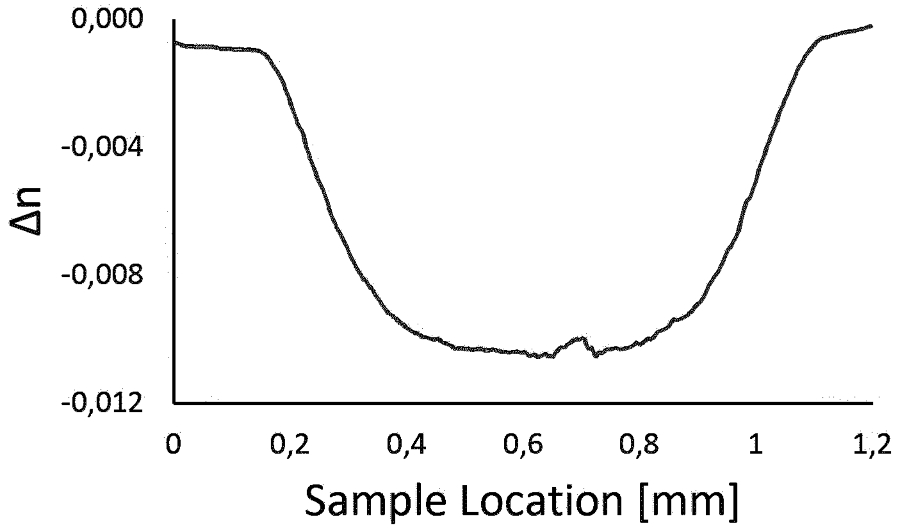
FIG. 24 shows a selected example of a refractive-index profile written into the optical material in the course of the experiment of example 20.

The invention claimed is:

1. An ophthalmic surgical system, the system comprising:
- an artificial lens;
- one or more irradiation sources for two-photon or multi-photon irradiating said artificial lens with an irradiation beam focused with an optic and of a first wavelength and/or a second wavelength different from the first wavelength,
- a scanner coupled to the one or more irradiation sources and configured to scan said irradiation beam across said artificial lens, and
- an input unit coupled to the one or more irradiation sources and the scanner, wherein the input unit is configured to input data for treating said artificial lens by scanning said irradiation beam across said artificial lens based on the input data, and
- wherein the first wavelength is between 600 nm and 800 nm and the artificial lens is configured to absorb the irradiation beam of the first wavelength via a two-photon or multi-photon absorption process and to locally decrease, as a result of said absorption process, a polarizability of irradiated portions of said artificial lens, and
- wherein the second wavelength is between 400 nm and 590 nm and the artificial lens is configured to absorb the irradiation beam of the second wavelength via a two-photon or multi-photon absorption process and to locally increase, as a result of said absorption process, the polarizability of irradiated portions of said artificial lens.

2. The system according to claim 1 wherein the artificial lens is a contact lens or intraocular lens.

3. The system according to claim 1 wherein the artificial lens is arranged within an eye of a patient.

4. The system according to claim 3, further comprising a positioning system for determining a position of a focus of said irradiation beam within said eye of said patient, wherein the positioning system is coupled to the scanner and wherein the scanning, by the scanner, of said irradiation beam across said artificial lens is based on the position of said focus of said irradiation beam within the eye.

5. The system according to claim 3, wherein the system is configured to determine a location and/or orientation of said artificial lens relative to the eye and an outlet of the irradiation beam, and wherein the scanning, by the scanner, of said irradiation beam across said artificial lens is based on the location and/or orientation of said artificial lens relative to the eye.

6. The system according to claim 3, further comprising an eye interface system configured to keep said eye of said patient in a fixed position.

7. The system according to claim 1, wherein the input data comprises lens data of said artificial lens and/or treatment plan data relating to a treatment plan for said treating of said artificial lens.

8. The system according to claim 7, wherein the lens data comprises data relating to a radiation absorption property of said artificial lens, and wherein the system is configured to adjust the first wavelength and/or the second wavelength for said artificial lens to locally change the polarizability based on the two-photon or multi-photon absorption process.

9. The system according to claim 1, further comprising a temperature management unit coupled to one or both of (i) the one or more irradiation sources and (ii) the scanner, wherein the temperature management unit is configured to determine, based on an irradiation beam property of said irradiation beam and an artificial lens property of said artificial lens, a temperature of a part of said artificial lens during said treating of said artificial lens by said scanning, and wherein the system is configured to control, based on said determination of the temperature, one or both of (i) the one or more irradiation sources and (ii) the scanner.

10. The system according to claim 9, wherein the temperature management unit is configured to predict said temperature during said treating of said artificial lens, and wherein said input data comprises the predicted temperature.

11. A process for adjusting a polarizability of an artificial lens comprising a body formed of a polymeric optical material based on a two- or multi-photon absorption process, the process comprising the steps of:

providing said artificial lens; and adjusting the polarizability of said artificial lens through irradiation of said lens by using a system which comprises one or more irradiation sources generating a first and a second focused irradiation beam and a scanner configured to scan the first and second focused irrational beams across said artificial lens, thereupon changing the polymeric optical material with significant differences in a UV/Vis spectrum with respect to non-irradiated polymeric optical material of the artificial lens, the adjusting step including:

irradiating a first portion of the artificial lens with the first irradiation beam having a first wavelength between 600 nm and 800 nm, wherein the artificial lens absorbs the first irradiation beam via the two- or multi-photon absorption process and locally decreases, as a result of the absorption process, a polarizability of the first portion of the artificial lens, and irradiating a second portion of the artificial lens with the second irradiation beam having a second wavelength between 400 nm and 590 nm, wherein the artificial lens absorbs the second irradiation beam via the two- or multi-photon absorption process and locally increases, as a result of the absorption process, a polarizability of the second portion of the artificial lens.

12. The process according to claim 11, wherein said irradiating a first portion of the artificial lens with the first irradiation beam having the first wavelength of between 600 nm and 800 nm changes the polymeric optical material with significant differences of the UV/Vis spectrum namely loss in peak absorption in a range of 300 nm to 400 nm with respect to the non-irradiated polymeric optical material of the artificial lens.

13. The process according to claim 11, wherein said irradiating a second portion of the artificial lens with the second irradiation beam having the second wavelength of between 400 nm and 590 nm changes the polymeric optical material with significant differences of the UV/Vis spectrum namely increase in peak absorption in a range of 300 nm to 400 nm with respect to the non-irradiated polymeric optical material of the artificial lens.

14. The process according to claim 11, wherein said polymeric optical material of the artificial lens comprises a polymeric matrix comprising covalently bound photoactive units comprising a non-aromatic double bond which is able to dimerize by forming a cyclobutane ring by means of a [2π+2π] cycloaddition under the effect of the two-photon or multi-photon absorption process.

15. The process according to claim 11, wherein said optical material of the artificial lens comprises a polymeric matrix comprising covalently bound photoactive units comprising a non-aromatic double bond which is able to dimerize by forming a cyclobutane ring by means of a [2π+2π] cycloaddition under the effect of the two-photon or multi-photon absorption process together with already dimerized photoactive units.

16. The process according to claim 15, wherein the provided artificial lens is irradiated with the irradiation beam of the first wavelength said irradiation causes the dimerization of said photoactive units thereby decreasing the polarizability of said artificial lens and thereby modifying the provided artificial lens in that the modified artificial lens comprises a polymeric matrix comprising more dimerized photoactive units derived from said [2π+2π] cycloaddition, or wherein the provided artificial lens is irradiated with the irradiation beam of the second wavelength, said irradiation causes the separation of said dimerized photoactive units thereby increasing the polarizability of said artificial lens and thereby modifying the provided artificial lens in that the modified artificial lens comprises a polymeric matrix comprising more photoactive units able to dimerize by forming a cyclobutane ring by means of a [2π+2π] cycloaddition.

17. The process according to claim 11, wherein said polymeric optical material of the artificial lens comprises a polymeric matrix comprising covalently bound dimerized photoactive units as sole photoactive units which are able to separate under the effect of the two-photon or generally multi-photon absorption process.

18. The process according to claim 17, wherein the provided artificial lens is irradiated with the irradiation beam of the second wavelength, said irradiation causes the separation of said dimerized photoactive units thereby increasing the polarizability of said artificial lens and thereby modifying the provided artificial lens in that the modified artificial lens comprises a polymeric matrix comprising photoactive units able to dimerize again and optionally irradiating said modified artificial lens with an irradiation beam of the first wavelength for locally decreasing the polarizability of said modified artificial lens by partially dimerizing said photoactive units.

19. The process according to claim 11, wherein the provided artificial lens comprising a polymeric matrix comprises covalently bound photoactive units comprising a non-aromatic double bond which is able to dimerize by forming a cyclobutane ring by means of a [2π+2π] cycloaddition is irradiated with the irradiation beam of the first wavelength, said irradiation causes the dimerization of said photoactive units thereby decreasing the polarizability of said artificial lens and thereby modifying the provided artificial lens in that the modified artificial lens comprises a polymeric matrix comprising partially or fully dimerized photoactive units derived from said [2π+2π] cycloaddition and optionally irradiating said modified artificial lens with an irradiation beam of the second wavelength for locally increasing the polarizability of said modified artificial lens by partially cleaving said dimerized photoactive units.

* * * * *